US006370430B1

(12) United States Patent
Mika et al.

(10) Patent No.: US 6,370,430 B1
(45) Date of Patent: Apr. 9, 2002

(54) APPARATUS AND METHOD FOR CONTROLLING THE DELIVERY OF NON-EXCITATORY CARDIAC CONTRACTILITY MODULATING SIGNALS TO A HEART

(75) Inventors: Yuval Mika, Zichron-Yaacov; Ziv Belsky, Haifa, both of (IL)

(73) Assignee: Impulse Dynamics N.V., Curecao (AN)

( * ) Notice: Subject to any disclaimer, the term of this patent is extended or adjusted under 35 U.S.C. 154(b) by 0 days.

(21) Appl. No.: 09/572,482

(22) Filed: May 16, 2000

Related U.S. Application Data

(63) Continuation-in-part of application No. 09/276,460, filed on Mar. 25, 1999, now Pat. No. 6,263,242.

(51) Int. Cl.[7] .................................................. A61N 1/36
(52) U.S. Cl. ............................................ 607/9; 607/25
(58) Field of Search ............................... 607/9, 11, 25, 607/68; 600/510

(56) References Cited

U.S. PATENT DOCUMENTS

| 4,554,922 A | 11/1985 | Prystowsky et al. |
| 4,559,947 A | 12/1985 | Renger et al. |
| 4,830,006 A | 5/1989 | Haluska et al. |

(List continued on next page.)

FOREIGN PATENT DOCUMENTS

| WO | WO 97/25098 | 7/1997 |
| WO | WO 98/10828 | 3/1998 |
| WO | WO 98/10829 | 3/1998 |
| WO | WO 98/10830 | 3/1998 |
| WO | WO 98/10831 | 3/1998 |
| WO | WO 98/10832 | 3/1998 |
| WO | WO 99/03533 | 1/1999 |
| WO | WO 00/57947 | 10/2000 |
| WO | WO 00/57952 | 10/2000 |

OTHER PUBLICATIONS

Classification of Cardiac Arrhythmias Using Fuzzy ART-MAP by Fredric M. Ham and Soowhan Han; IEEE Transactions on Biomedical Engineering, vol. 43, No. 4, pp. 425–430, Apr. 1996.

Neural Network Based Adaptive Matched Filtering for QRS Detection by Qiuzhen Xue et al., IEEE Transactions on Biomedical Engineering, vol. 39, No. 4, pp.317–329, Apr. 1992.

(List continued on next page.)

Primary Examiner—Jeffrey R. Jastrzab
(74) Attorney, Agent, or Firm—Cowan, Liebowitz & Latman, P.C.; William H. Dippert

(57) ABSTRACT

A method and device for controlling the delivery of cardiac contractility modulating signals to the heart are disclosed. The method includes applying electrodes to a heart, sensing electrical activity in a first cardiac chamber and in at least a second cardiac chamber to detect events within a cardiac beat cycle and applying a cardiac contractility modulating signal to the heart at or about the first cardiac chamber in response to detecting an event within an alert window time interval. The applying of the cardiac contractility modulating signal is inhibited in response to detecting one or more inhibitory events occurring within specific time intervals defined within a current beat cycle. The method also includes the ignoring of events associated with expected electrical artifact signals if they occur within the duration of specified time intervals, to increase the therapy efficacy. The artifact signals may be associated with pacing of a cardiac chamber or with detected far field sensed electrical artifacts due to intrinsic chamber activation. The timing of the various time intervals and of the cardiac contractility signal may be computed on a beat by beat basis by utilizing a plurality of parameter sets stored in the device and the timing of events detected in each beat cycle. A method for determining and setting the parameter sets in a test session is disclosed.

129 Claims, 25 Drawing Sheets

U.S. PATENT DOCUMENTS

| | | |
|---|---|---|
| 4,971,058 A | 11/1990 | Pless et al. |
| 5,083,564 A | 1/1992 | Scherlag |
| 5,154,501 A | 10/1992 | Svenson et al. |
| 5,161,527 A | 11/1992 | Nappholz et al. |
| 5,172,699 A | 12/1992 | Svenson et al. |
| 5,184,620 A | 2/1993 | Cudahy et al. |
| 5,205,284 A | 4/1993 | Freeman |
| 5,281,219 A | 1/1994 | Kallock |
| 5,391,192 A | 2/1995 | Lu et al. |
| 5,443,485 A | 8/1995 | Housworth et al. |
| 5,443,489 A | 8/1995 | Ben-Haim |
| 5,549,646 A | 8/1996 | Katz et al. |
| 5,683,431 A | 11/1997 | Wang |
| 5,749,906 A | 5/1998 | Kieval et al. |
| 5,782,876 A | 7/1998 | Flammang |
| 5,782,881 A | 7/1998 | Lu et al. |
| 5,800,464 A | 9/1998 | Kieval |
| 5,814,079 A | 9/1998 | Kieval |
| 5,871,506 A | 2/1999 | Mower |

OTHER PUBLICATIONS

Identification of Ventricular Tachycardia with use of the Morphology of the Endocardial Eectrogram by Jonathan J. Langberg. et al. Circulation, vol. 77. No. 6, pp. 1363–1369, Jun. 1988.

"Automated Detection of Tachardias by Antitachicardia Devices", A. D. Mercando et al., Chapter 100, pp. 943–948, in Cardiac Electrophysiology from Cell to Bedside, Eds. Douglas P. Zipes and Jose Jalife, publishers W. B. Saunders Company (1990).

Pace, vol.14, Automatic Recognition of Ventricular Arrythmias Using Temporal Electrogram Analysis, Paul, V. E. et al., pp. 1265–1273, (1991).

Polarization Effects of Sinusoidal 50–Cycle Alternating Current on Membrane Potential of Mammalian Cardiac Fibres, H. Antoni et al, Pflügers Arch.314, 274–291 (1970).

APPARATUS AND METHOD FOR CONTROLLING THE DELIVERY OF NON-EXCITATORY CARDIAC CONTRACTILITY MODULATING SIGNALS TO A HEART

RELATED U.S. APPLICATIONS

The present application is a continuation in part application of U.S. patent application to Mika et al., Ser. No. 09/276,460, filed Mar. 25, 1999 now U.S. Pat. No. 6,263,242 titled "APPARATUS AND METHOD FOR TIMING THE DELIVERY OF NON-EXCITATORY ETC SIGNALS TO A HEART", filed Mar. 25, 1999, the entire specification of which is incorporated herein by reference.

FIELD OF THE INVENTION

The present invention relates generally to the field of methods and medical devices for modulating cardiac muscle activity and contractility and for cardiac pacing and more specifically to the field of methods for controlling the delivery of non-excitatory excitable tissue control (ETC) signals to the heart.

BACKGROUND OF THE INVENTION

Excitable tissue control (ETC) devices are devices which modulate the activity of excitable tissues by application of non-excitatory electrical field signals to the excitable tissue through suitable electrodes in contact with the tissue. For example, ETC devices which are also known in the art as cardiac contractility modulation (CCM) devices may be used, inter alia, to increase or decrease the contractility of cardiac muscle in vitro, in vivo and in situ., as disclosed in detail in PCT application PCT/IL97/00012 (International Publication Number WO 97/25098) to Ben-Haim et al., titled "ELECTRICAL MUSCLE CONTROLLER", incorporated herein by reference. Other methods and applications of ETC devices are disclosed in PCT application PCT/IL97/00231 (International Publication Number WO 98/10828) titled "APPARATUS AND METHOD FOR CONTROLLING THE CONTRACTILITY OF MUSCLES" to Ben Haim et al., incorporated herein by reference, PCT application PCT/IL97/00232 (International Publication Number WO 98/10829) titled "DRUG-DEVICE COMBINATION FOR CONTROLLING THE CONTRACTILITY OF MUSCLES" to Ben Haim et al., incorporated herein by reference and PCT application PCT/IL97/00233 (International Publication Number WO 98/10830) titled "FENCING OF CARDIAC MUSCLES" to Ben Haim et al., incorporated herein by reference, PCT application PCT/IL97/00235 (International Publications Number WO 98/10831) to Ben Haim et al., titled "CARDIAC OUTPUT CONTROLLER", incorporated herein by reference.

Co-Pending U.S. patent application to Darvish et al., Ser. No. 09/260,769, titled "CONTRACTILITY ENHANCEMENT USING EXCITABLE TISSUE CONTROL AND MULTI-SITE PACING", filed Mar. 2, 1999 and assigned to the common assignee of the present application, the entire specification of which is incorporated herein by reference, discloses a method for multi-site cardiac pacing combined with ETC signal delivery for cardiac output enhancement.

Further applications of the ETC including devices combining cardiac pacing and cardiac contractility modulation are disclosed in PCT Application, International Publication No. WO 98/10832, titled "CARDIAC OUTPUT ENHANCED PACEMAKER" to Ben Haim et al., co-assigned to the assignee of the present application. Such ETC devices function by applying to selected cardiac segments non-excitatory electrical signals of suitable amplitude and waveform, appropriately timed with respect to the heart's intrinsic electrical activity or with respect to paced cardiac electrical activity. The contraction of the selected segments can be modulated to increase or decrease the stroke volume of the heart. The timing of the ETC signals must be carefully controlled since application of the ETC signal to the myocardium at inappropriate times may be arrhythmogenic. The ETC signal must therefore be applied to the selected cardiac segment within a defined time interval during which the selected cardiac segment will not be stimulated by the ETC signal.

As disclosed in International Publication No. WO 98/10832, the ETC signal may be timed relative to a trigger signal which is also used as a pacing trigger, or may be timed relative to locally sensed depolarizing electrogram signals.

Timing of the delivery of ETC signals relative to the time of detection of locally sensed electrogram signals may present certain practical problems. For example, triggering of the ETC signal by any locally detected depolarizing signals irrespective of the time of detection of the depolarizing signal within the cardiac beat cycle, may increase the probability of spurious detection of noise signals or of ectopic beats such as premature ventricular contractions (PVCs) or the like, which may lead to delivery of improperly timed and potentially arrhythmogenic ETC signals. It is therefore desirable to have a method for determining proper timing of the delivery of ETC signals without unduly increasing the probability of delivering an improperly timed ETC signal caused by spurious noise detection or by detection of ectopic beats.

Co-pending U.S. Patent Application to Mika et al., Ser. No. 09/276,460, titled "APPARATUS AND METHOD FOR TIMING THE DELIVERY OF NON-EXCITATORY ETC SIGNALS TO A HEART", filed Mar. 25, 1999 and assigned to the common assignee of the present application, the entire specification of which is incorporated herein by reference, discloses a method for timing the delivery of non-excitatory ETC signals to a heart using, inter alia, an alert window period for reducing the probability of delivering an improperly timed ETC signal to the heart due to spurious detection of noise or ectopic beats.

Co-pending U.S. patent application Ser. No. 09/338,649 to Mika et al., titled "APPARATUS AND METHOD FOR SETTING THE PARAMETERS OF AN ALERT WINDOW USED FOR TIMING THE DELIVERY OF ETC SIGNALS TO A HEART UNDER VARYING CARDIAC CONDITIONS", filed Jun. 23, 1999, the entire specification of which is incorporated herein by reference, discloses devices and methods for timing of delivery of ETC signals to the heart using, inter alia, a dynamically varying alert window period for event sensing.

Co-pending U.S. patent application Ser. No. 09/328,068 to Mika et al., filed Jun. 8, 1999, titled "APPARATUS AND METHOD FOR COLLECTING DATA USEFUL FOR DETERMINING THE PARAMETERS OF AN ALERT WINDOW FOR TIMING DELIVERY OF ETC SIGNALS TO A HEART UNDER VARYING CARDIAC CONDITIONS", the entire specification of which is incorporated herein by reference, discloses devices and methods for collecting patient data which is usable for the operation of a device for timing of delivery of ETC signals to the heart using, inter alia, a dynamically varying alert window period for event sensing.

SUMMARY OF THE INVENTION

It is noted that, while generally the term ETC signal refers to non-excitatory electrical signals applied to an excitable tissue, the terms ETC signal and CCM signal are interchangeably used throughout the present application to define non-excitatory cardiac contractility modulating electrical signals which are delivered to a heart. Similarly, while generally the term ETC device refers to a device which is capable, inter alia, of delivering non-excitatory contractility modulating electrical signals to an excitable tissue, the terms ETC device and CCM device are interchangeably used throughout the present application, to define a device which is capable, inter alia, of delivering non-excitatory cardiac contractility modulating electrical signals to a heart.

There is therefore provided, in accordance with a preferred embodiment of the present invention a method for controlling the delivery of a non-excitatory cardiac contractility modulating signals to a heart within a cardiac beat cycle. The method includes the step of sensing electrical activity in or about a first cardiac chamber to provide a first electrogram signal. The method also includes the step of detecting electrical events in the first electrogram signal. The method also includes the step of providing a first artifact window within the current beat cycle and detecting events occurring in the first electrogram signal within the duration of the first artifact window. The first artifact window starts at or after a trigger event representing the beginning of the current cardiac beat cycle. The first artifact window has a first artifact window duration. The method also includes the step of providing an alert window period within the current beat cycle. The alert window period has a first duration and is delayed from the trigger event. The method also includes the step of enabling the delivery of a cardiac contractility modulating signal to the first chamber of the heart within the current beat cycle in response to a first event detected in the first electrogram signal within the duration of the alert window period. The delivery of the cardiac contractility modulating signal is delayed from the time of detecting of the first event occurring within the duration of the alert window period by a first delay period. The cardiac contractility modulating signal has a cardiac contractility modulating signal duration. The method also includes the step of providing a refractory period within the current beat cycle, in response to the first event of the step of enabling for preventing the detection of electrical events within the duration of the refractory period. The refractory period has a refractory period duration, a beginning time and an ending time. The beginning time of the refractory period is delayed from the first event of the step of enabling by a second delay period. The ending time of the refractory period occurs at or after the termination of the cardiac contractility modulating signal. The method also includes the steps of applying the cardiac contractility modulating signal to the heart within the current beat cycle, and inhibiting the performing of the step of providing a refractory period and of the step of applying the cardiac contractility modulating signal, in response to detecting at least one inhibiting event within the first electrogram signal.

Furthermore, in accordance with another preferred embodiment of the present invention, the first cardiac chamber is the left ventricle of the heart.

Furthermore, in accordance with another preferred embodiment of the present invention, the first cardiac chamber is the right ventricle of the heart.

Furthermore, in accordance with another preferred embodiment of the present invention, the trigger event is an event associated with electrical activation of the right ventricle of the heart.

Furthermore, in accordance with another preferred embodiment of the present invention, the trigger event is a right ventricular event detected by a sensing electrode electrically coupled to the right ventricle of the heart.

Furthermore, in accordance with another preferred embodiment of the present invention, the trigger event is a right ventricular pacing command or an event synchronized therewith.

Furthermore, in accordance with another preferred embodiment of the present invention, the trigger event is an event associated with electrical activation of the right atrium of the heart.

Furthermore, in accordance with another preferred embodiment of the present invention, the trigger event is a right atrial event detected by a sensing electrode electrically coupled to the right atrium of the heart.

Furthermore, in accordance with another preferred embodiment of the present invention, the trigger event is a right atrial pacing command or an event synchronized therewith.

Furthermore, in accordance with another preferred embodiment of the present invention, the preventing of the step of providing a refractory period includes the step of stopping the sensing of the first electrogram signal within the duration of the refractory period.

Furthermore, in accordance with another preferred embodiment of the present invention, the preventing of the step of providing a refractory period includes the step of stopping the detecting of the electrical events in the first electrogram signal within the duration of the refractory period.

Furthermore, in accordance with another preferred embodiment of the present invention, the step of detecting includes detecting electrical events based on a single threshold crossing criterion of the first electrogram signal.

Furthermore, in accordance with another preferred embodiment of the present invention, the step of detecting includes detecting electrical events using a detection method based on one or more detection criteria selected from, the crossing of at least one threshold by the first electrogram signal, a slope criterion, a criterion based on one or more morphological parameters of the first electrogram signal and any combination thereof.

Furthermore, in accordance with another preferred embodiment of the present invention, the alert window period starts immediately after the first artifact window ends.

Furthermore, in accordance with another preferred embodiment of the present invention, the first delay period is equal to the second delay period.

Furthermore, in accordance with another preferred embodiment of the present invention, the first delay period is larger than the second delay period.

Furthermore, in accordance with another preferred embodiment of the present invention, the at least one inhibitory event includes a single event or any combination of events selected from the group of events consisting of, an event detected in the first electrogram signal within the time interval between the ending time of the first artifact window and the starting time of the alert window period, an event detected in the first electrogram signal within the duration of the alert window period after the time of detection of the first event of the step of enabling, and an event detected within the time interval starting after the end of the alert window and ending at the beginning time of the refractory period.

Furthermore, in accordance with another preferred embodiment of the present invention, the method further includes the step of inhibiting the delivery of a cardiac contractility modulating signal to the heart within the next beat cycle following the current beat cycle, in response to detecting in the first electrogram signal an event within the duration of a sensing time period starting after the end of the refractory period and ending at the end of the current beat cycle.

Furthermore, in accordance with another preferred embodiment of the present invention, the delivery of a cardiac contractility modulating signal to the heart within the current beat cycle was inhibited in the step of inhibiting due to an event detected in the first electrogram signal within the time interval between the ending time of the first artifact window and the starting time of the alert window period, or due to an event detected in the first electrogram signal within the duration of the alert window period after the time of detection of the first event of the step of enabling, and the method further includes the step of inhibiting the delivery of an cardiac contractility modulating signal to the heart within the next beat cycle following the current beat cycle, in response to detecting in the first electrogram signal an event within the duration of a time period starting after the end of the alert window and ending at the end of the first delay period.

Furthermore, in accordance with another preferred embodiment of the present invention, the step of providing a first artifact window includes the steps of: if the trigger event is a sensed event associated with intrinsic activation of a second cardiac chamber, automatically selecting a first artifact window parameter set associated with the first artifact window, if the trigger event is an event associated with pacing of the second cardiac chamber, automatically selecting a second parameter set associated with the first artifact window, and determining the beginning time and the ending time of the first artifact window relative to the trigger event from the automatically selected parameter set.

Furthermore, in accordance with another preferred embodiment of the present invention, the second cardiac chamber is the right atrium of the heart, the first parameter set is determined based on data obtained from cardiac beats of the heart in which the trigger event is a right atrial sensed event associated with intrinsic activation of the right atrium, the second parameter set is determined based on data obtained from cardiac beats of the heart in which the trigger event is an event associated with pacing of the right atrium, and each of the first parameter set and the second parameter set includes a first parameter representing the delay between the trigger event and the beginning time of the first artifact window and a second parameter representing the duration of the first artifact window.

Furthermore, in accordance with another preferred embodiment of the present invention, the second cardiac chamber is the right ventricle of the heart, the first parameter set is determined based on data obtained from cardiac beats of the heart in which the trigger event is a sensed event associated with intrinsic activation of the right ventricle, and the second parameter set is determined based on data obtained from cardiac beats of the heart in which the trigger event is an event associated with pacing of the right ventricle.

Furthermore, in accordance with another preferred embodiment of the present invention, the first parameter set of the first artifact window is identical to the second parameter set of the first artifact window.

Furthermore, in accordance with another preferred embodiment of the present invention, the first parameter set of the first artifact window is different than the second parameter set of the first artifact window.

Furthermore, in accordance with another preferred embodiment of the present invention, the first artifact window starts at the time of detecting of the trigger event, the step of providing a first artifact window further includes the step of determining the duration of the first artifact window within the current beat cycle by automatically selecting a first duration value for the first artifact window if the trigger event is a sensed event associated with intrinsic activation of a second cardiac chamber, and automatically selecting a second duration value for the first artifact window if the trigger event is an event associated with pacing of the second cardiac chamber.

Furthermore, in accordance with another preferred embodiment of the present invention, the second cardiac chamber is the right atrium of the heart. The first duration value of the first artifact window is predetermined based on data obtained from cardiac beats of the heart in which the trigger event is a right atrial sensed event associated with intrinsic activation of the right atrium, and the second duration value of the first artifact window is predetermined based on data obtained from cardiac beats of the heart in which the trigger event is an event associated with pacing of the right atrium.

Furthermore, in accordance with another preferred embodiment of the present invention, the second cardiac chamber is the right ventricle of the heart. The first duration value of the first artifact window is predetermined based on data obtained from cardiac beats of the heart in which the trigger event is a sensed event associated with intrinsic activation of the right ventricle, and the second duration value of the first artifact window is predetermined based on data obtained from cardiac beats of the heart in which the trigger event is an event associated with pacing of the right ventricle.

Furthermore, in accordance with another preferred embodiment of the present invention, the first duration value of the first artifact window is identical to the second duration value of the first artifact window.

Furthermore, in accordance with another preferred embodiment of the present invention, the first duration value of the first artifact window is different than the second duration value of the first artifact window.

Furthermore, in accordance with another preferred embodiment of the present invention, the step of providing an alert window period includes the step of determining the beginning time and the ending time of the alert window within the current beat cycle by automatically selecting a first alert window parameter set associated with the alert window period if the trigger event is a sensed event associated with intrinsic activation of a second cardiac chamber, automatically selecting a second parameter set associated with the alert window period if the trigger event is an event associated with pacing of the second cardiac chamber, and by computing the beginning time and the duration of the first artifact window from the selected parameter set.

Furthermore, in accordance with another preferred embodiment of the present invention, the first cardiac chamber is the left ventricle of the heart, the second cardiac chamber is the right atrium of the heart, the first parameter set is determined based on data obtained from cardiac beats of the heart in which the trigger event is a sensed event associated with intrinsic activation of the right atrium, and the second parameter set is determined based on data obtained from cardiac beats of the heart in which the trigger event is an event associated with pacing of the right atrium.

Furthermore, in accordance with another preferred embodiment of the present invention, the first cardiac chamber is the left ventricle of the heart, the second cardiac chamber is the right ventricle of the heart, the first parameter set is determined based on data obtained from cardiac beats of the heart in which the trigger event is a sensed event associated with intrinsic activation of the right ventricle, and the second parameter set is determined based on data obtained from cardiac beats of the heart in which the trigger event is an event associated with pacing of the right ventricle.

Furthermore, in accordance with another preferred embodiment of the present invention, the method further includes the steps of: initiating an artifact proximity interval, the artifact proximity interval starts at the time of detection of a proximity interval initiating event detected within the duration of the first artifact window and has an artifact proximity interval duration, and inhibiting the performing of the step of providing a refractory period and of the step of applying, in response to detecting in the first electrogram signal an event occurring within the duration of a part of the artifact proximity interval. The part does not overlap the first artifact window.

Furthermore, in accordance with another preferred embodiment of the present invention, the proximity artifact interval partially overlaps the alert window period.

Furthermore, in accordance with another preferred embodiment of the present invention, the second step of inhibiting is performed when the event detected within the duration of the part of the artifact proximity interval occurs within a portion of the alert window period. The portion overlaps the artifact proximity interval.

Furthermore, in accordance with another preferred embodiment of the present invention, the step of initiating an artifact proximity interval further includes the step of determining the duration of the artifact proximity interval by automatically selecting a first duration value for the artifact proximity interval if the trigger event is a sensed event associated with intrinsic activation of a second cardiac chamber, and automatically selecting a second duration value for the artifact proximity interval if the trigger event is an event associated with pacing of the second cardiac chamber.

Furthermore, in accordance with another preferred embodiment of the present invention, the first cardiac chamber is the left ventricle of the heart, the second cardiac chamber is the right ventricle of the heart, the first duration of the artifact proximity interval is determined based on data obtained from cardiac beats of the heart in which the trigger event is a right ventricular sensed event associated with intrinsic activation of the right ventricle, and the second duration of the first artifact window is determined based on data obtained from cardiac beats of the heart in which the trigger event is an event associated with pacing of the right ventricle.

Furthermore, in accordance with another preferred embodiment of the present invention, the proximity interval initiating event is the first event detected within the duration of the first artifact window.

Furthermore, in accordance with another preferred embodiment of the present invention, more than one event is detected within the duration of the first artifact window and the proximity interval initiating event is the last event detected within the duration of the first artifact window.

Furthermore, in accordance with another preferred embodiment of the present invention, a plurality of events is detected within the duration of the first artifact window, and the proximity interval initiating event is a single event selected from the plurality of events.

Furthermore, in accordance with another preferred embodiment of the present invention, the proximity interval initiating event is an event detected within the duration of the first artifact window using a detection method based on an analysis of morphological parameters of the first electrogram signal.

Furthermore, in accordance with another preferred embodiment of the present invention, the method further includes the step of providing a second artifact window period within the current beat cycle in response to a first timing event and ignoring all events detected in the first electrogram signal within the duration of the second artifact window period to avoid inhibiting the delivery of the cardiac contractility modulating signal within the current beat cycle by the detection of an expected electrical artifact signal within the duration of the second artifact window period.

Furthermore, in accordance with another preferred embodiment of the present invention, the first cardiac chamber is the left ventricle of the heart, the trigger event is an event associated with electrical activation of the right atrium of the heart, and the first timing event is an event associated with electrical activation of the right ventricle of the heart.

Furthermore, in accordance with another preferred embodiment of the present invention, the trigger event is a right atrial event detected by a sensing electrode electrically coupled to the right atrium of the heart, and wherein the first timing event is a right ventricular event detected by a sensing electrode electrically coupled to the right ventricle of the heart.

Furthermore, in accordance with another preferred embodiment of the present invention, the trigger event is a right atrial event detected by a sensing electrode electrically coupled to the right atrium of the heart, and the first timing event is a right ventricular pacing command or an event synchronized therewith.

Furthermore, in accordance with another preferred embodiment of the present invention, the trigger event is a right atrial pacing command or an event synchronized therewith, and the first timing event is a right ventricular event detected by a sensing electrode electrically coupled to the right ventricle of the heart.

Furthermore, in accordance with another preferred embodiment of the present invention, the trigger event is a right atrial pacing command or an event synchronized therewith, and the first timing event is a right ventricular pacing command or an event synchronized therewith.

Furthermore, in accordance with another preferred embodiment of the present invention, the step of providing a second artifact window includes the step of computing, within the duration of the current beat cycle, the beginning time and the ending time of the second artifact window period based on the time of occurrence of the first timing event and on the value of a pair of predetermined reconstruction parameters.

Furthermore, in accordance with another preferred embodiment of the present invention, the beginning time of the second artifact window computed in the step of computing precedes the first timing event within the current beat cycle.

Furthermore, in accordance with another preferred embodiment of the present invention, the beginning time of the second artifact window and the first timing event are identical within the current beat cycle.

Furthermore, in accordance with another preferred embodiment of the present invention, the first timing event precedes the ending time of the second artifact window within the current beat cycle.

Furthermore, in accordance with another preferred embodiment of the present invention, the ending time of the second artifact window and the first timing event are identical within the current beat cycle.

Furthermore, in accordance with another preferred embodiment of the present invention, the first chamber is the left ventricle of the heart and the step of providing a second artifact window includes the steps of: if the first timing event is a sensed event associated with intrinsic activation of the right ventricle of the heart, automatically selecting a first parameter set associated with the second artifact window, if the first timing event is an event associated with pacing of the right ventricle of the heart, automatically selecting a second parameter set associated with the second artifact window, and determining the beginning time and the ending time of the second artifact window within the current beat cycle from the time of occurrence of the first timing event and from the automatically selected parameter set.

Furthermore, in accordance with another preferred embodiment of the present invention, the first parameter set is determined based on data obtained from cardiac beats of the heart in which the first timing event is a right ventricular sensed event associated with intrinsic activation of the right ventricle, and the second parameter set is determined based on data obtained from cardiac beats of the heart in which the first timing event is an event associated with pacing of the right ventricle.

Furthermore, in accordance with another preferred embodiment of the present invention, the first parameter set of the second artifact window is identical to the second parameter set of the second artifact window.

Furthermore, in accordance with another preferred embodiment of the present invention, the first parameter set of the second artifact window is different than the second parameter set of the second artifact window.

Furthermore, in accordance with another preferred embodiment of the present invention, the method further includes the step of providing a third artifact window period within the current beat cycle in response to a second timing event and ignoring all events detected in the first electrogram signal within the duration of the third artifact window period to avoid inhibiting the delivery of a cardiac contractility modulating signal within the next beat cycle following the current beat cycle by the detection of an expected electrical artifact signal within the duration of the third artifact window period of the current beat cycle.

Furthermore, in accordance with another preferred embodiment of the present invention, the first cardiac chamber is the left ventricle of the heart, the trigger event is an event associated with electrical activation of the right ventricle of the heart and the second timing event is an event associated with electrical activation of the right atrium of the heart.

Furthermore, in accordance with another preferred embodiment of the present invention, the trigger event is a right ventricular event detected by a sensing electrode electrically coupled to the right ventricle of the heart, and the second timing event is a right atrial event detected by a sensing electrode electrically coupled to the right atrium of the heart.

Furthermore, in accordance with another preferred embodiment of the present invention, the trigger event is a right ventricular event detected by a sensing electrode electrically coupled to the right ventricle of the heart, and the second timing event is a right atrial pacing command or an event synchronized therewith.

Furthermore, in accordance with another preferred embodiment of the present invention, the trigger event is a right ventricular pacing command or an event synchronized therewith, and the second timing event is a right atrial event detected by a sensing electrode electrically coupled to the right atrium of the heart.

Furthermore, in accordance with another preferred embodiment of the present invention, the trigger event is a right ventricular pacing command or an event synchronized therewith, and the second timing event is a right atrial pacing command or an event synchronized therewith.

Furthermore, in accordance with another preferred embodiment of the present invention, the step of providing a third artifact window includes the step of computing, within the duration of the current beat cycle, the beginning time and the ending time of the third artifact window period based on the time of occurrence of the second timing event and on the value of a pair of predetermined reconstruction parameters.

Furthermore, in accordance with another preferred embodiment of the present invention, the beginning time of the third artifact window computed in the step of computing precedes the second timing event within the current beat cycle.

Furthermore, in accordance with another preferred embodiment of the present invention, the beginning time of the third artifact window and the second timing event are identical within the current beat cycle.

Furthermore, in accordance with another preferred embodiment of the present invention, the second timing event precedes the ending time of the third artifact window within the current beat cycle.

Furthermore, in accordance with another preferred embodiment of the present invention, the ending time of the third artifact window and the second timing event are identical within the current beat cycle.

Furthermore, in accordance with another preferred embodiment of the present invention, the first chamber is the left ventricle of the heart, and the trigger event is a trigger event associated with the right ventricle of the heart and wherein the step of providing a third artifact window includes the steps of: if the second timing event is a sensed event associated with intrinsic activation of the right atrium of the heart, automatically selecting a first artifact window parameter set associated with the third artifact window; if the second timing event is an event associated with pacing of the right atrium of the heart, automatically selecting a second parameter set associated with the third artifact window; and determining the beginning time and the ending time of the third artifact window within the current beat cycle from the time of occurrence of the second timing event and from the automatically selected parameter set.

Furthermore, in accordance with another preferred embodiment of the present invention, the first parameter set is determined based on data obtained from cardiac beats of the heart in which the second timing event is a right atrial sensed event associated with intrinsic activation of the right atrium, and the second parameter set is determined based on data obtained from cardiac beats of the heart in which the second timing event is an event associated with pacing of the right atrium.

Furthermore, in accordance with another preferred embodiment of the present invention, the first parameter set associated with the third artifact window is identical to the second parameter set associated with the third artifact window.

Furthermore, in accordance with another preferred embodiment of the present invention, the first parameter set associated with the third artifact window is different than the second parameter set associated with the third artifact window.

Furthermore, in accordance with another preferred embodiment of the present invention, the step of applying the cardiac contractility modulating signal includes the steps of: if the trigger event is a sensed event associated with intrinsic activation of a second cardiac chamber, automatically selecting a first parameter set associated with the cardiac contractility modulating signal; if the trigger event is an event associated with pacing of the second cardiac chamber, automatically selecting a second parameter set associated with the cardiac contractility modulating signal; computing the beginning time and the ending time of the cardiac contractility modulating signal within the current beat cycle from the automatically selected parameter set and from the time of detecting of the first event in the step of enabling; applying within the current beat cycle a cardiac contractility modulating signal having the beginning time and the ending time to the heart.

Furthermore, in accordance with another preferred embodiment of the present invention, each of the first parameter set and the second parameter set includes a value of the first delay period and a value of the cardiac contractility modulating signal duration.

Furthermore, in accordance with another preferred embodiment of the present invention, the first cardiac chamber is the left ventricle of the heart.

Furthermore, in accordance with another preferred embodiment of the present invention, the second cardiac chamber is the right ventricle of the heart.

Furthermore, in accordance with another preferred embodiment of the present invention, the first parameter set is determined based on data obtained from cardiac beats of the heart in which the trigger event is a right ventricular sensed event associated with intrinsic activation of the right ventricle, and the second parameter set is determined based on data obtained from cardiac beats of the heart in which the trigger event is an event associated with pacing of the right ventricle.

Furthermore, in accordance with another preferred embodiment of the present invention, the second cardiac chamber is the right atrium of the heart. Furthermore, in accordance with another preferred embodiment of the present invention, the first parameter set is determined based on data obtained from cardiac beats of the heart in which the trigger event is a right atrial sensed event associated with intrinsic activation of the right atrium, and the second parameter set is determined based on data obtained from cardiac beats of the heart in which the trigger event is an event associated with pacing of the right atrium.

Furthermore, in accordance with another preferred embodiment of the present invention, the step of providing a refractory period includes the steps of: if the trigger event is a sensed event associated with intrinsic activation of a second cardiac chamber, automatically selecting a first parameter set associated with the refractory period; if the trigger event is an event associated with pacing of the second cardiac chamber, automatically selecting a second parameter set associated with the refractory period; and, computing the beginning time and the ending time of the refractory period within the current beat cycle from the automatically selected parameter set and from the time of detecting of the first event in the step of enabling.

Furthermore, in accordance with another preferred embodiment of the present invention, each of the first parameter set and the second parameter set includes a value of the second delay period and a value of the refractory period duration.

Furthermore, in accordance with another preferred embodiment of the present invention, the first cardiac chamber is the left ventricle of the heart.

Furthermore, in accordance with another preferred embodiment of the present invention, the second cardiac chamber is the right ventricle of the heart, the first parameter set is determined based on data obtained from cardiac beats of the heart in which the trigger event is a right ventricular sensed event associated with intrinsic activation of the right ventricle, and the second parameter set is determined based on data obtained from cardiac beats of the heart in which the trigger event is an event associated with pacing of the right ventricle.

Furthermore, in accordance with another preferred embodiment of the present invention, the second cardiac chamber is the right atrium of the heart, the first parameter set is determined based on data obtained from cardiac beats of the heart in which the trigger event is a right atrial sensed event associated with intrinsic activation of the right atrium, and the second parameter set is determined based on data obtained from cardiac beats of the heart in which the trigger event is an event associated with pacing of the right atrium.

There is also provided, in accordance with another preferred embodiment of the present invention, a device for controlling the delivery of a non-excitatory cardiac contractility modulating signals to a heart within a cardiac beat cycle. The device includes sensing means for sensing electrical activity in or about a first cardiac chamber to provide a first electrogram signal, and for sensing electrical activity in or about at least a second cardiac chamber of the heart to provide at least a second electrogram signal; detecting means for detecting electrical events in the first electrogram signal and the at least second electrogram signal; means for providing a first artifact window within the current beat cycle, the first artifact window starts at or after a trigger event representing the beginning of the current cardiac beat cycle, the first artifact window has a first artifact window duration, and for detecting events occurring in the first electrogram signal within the duration of the first artifact window; means for providing an alert window period within the current beat cycle, the alert window period has a first duration and is delayed from the trigger event; means for enabling the delivery of a cardiac contractility modulating signal to the heart within the current beat cycle in response to a first event detected in the first electrogram signal within the duration of the alert window period, the delivery of the cardiac contractility modulating signal is delayed from the time of detecting of the first event occurring within the duration of the alert window period by a first delay period; means for providing a refractory period within the current beat cycle, in response to the first event, the refractory period has a beginning time and an ending time, the beginning time is delayed from the first event of the step of enabling by a second delay period, the ending time occurs at or after the termination of the cardiac contractility modulating signal, for preventing the detection of electrical events within the duration of the refractory period; means for applying the cardiac contractility modulating signal to the heart within the current beat cycle; and means for inhibiting the providing of the refractory period and for inhibiting the applying of the cardiac contractility modulating signal to the heart, in response to detecting at least one inhibiting event within the first electrogram signal.

Furthermore, in accordance with another preferred embodiment of the present invention, the device further includes pacing means for pacing at least one cardiac chamber of the heart.

Furthermore, in accordance with another preferred embodiment of the present invention, the device further includes implantable electrode means operatively connected to the pacing means, for applying pacing pulses to at least one chamber of the heart.

Furthermore, in accordance with another preferred embodiment of the present invention, the device further includes storage means for storing data within the device.

Furthermore, in accordance with another preferred embodiment of the present invention, the device further includes means for communicating data to and from the storage means.

Furthermore, in accordance with another preferred embodiment of the present invention, the device further includes implantable electrode means operatively connected to the sensing means and to the means for applying, to perform the sensing in the heart and to apply the cardiac contractility modulating signals to the heart.

Furthermore, in accordance with another preferred embodiment of the present invention, the device further includes means for inhibiting the delivery of a cardiac contractility modulating signal to the heart within the next cardiac beat cycle following the current beat cycle, in response to detecting in the first electrogram signal an event within the duration of a sensing time period. The sensing time period starts after the end of the refractory period of a beat cycle in which a cardiac contractility modulating signal is delivered to the heart and ends at the end of the current beat cycle in which a cardiac contractility modulating signal is delivered to the heart.

Furthermore, in accordance with another preferred embodiment of the present invention, the device further includes means for inhibiting the delivery of a cardiac contractility modulating signal to the heart within the next cardiac beat cycle following the current beat cycle, in response to detecting in the first electrogram signal an event within the duration of a sensing time period starting after the end of the alert window and ending at the end of the first delay period, wherein the delivery of a cardiac contractility modulating signal to the heart within the current beat cycle was inhibited in the current beat cycle.

Furthermore, in accordance with another preferred embodiment of the present invention, the at least one inhibitory event includes a single event or any combination of events selected from the group of events consisting of: an event detected in the first electrogram signal within the time interval between the ending time of the first artifact window and the starting time of the alert window period; an event detected in the first electrogram signal within the duration of the alert window period after the time of detection of the first event of the step of enabling; and an event detected within the time interval starting after the end of the alert window and ending at the beginning time of the refractory period.

Furthermore, in accordance with another preferred embodiment of the present invention, the device further includes: means for providing an artifact proximity interval, the artifact proximity interval starts at the time of detection of a proximity interval initiating event detected within the first artifact window and has an artifact proximity interval duration, and means for inhibiting the providing of the refractory period and for inhibiting the applying of the cardiac contractility modulating signal, in response to detecting in the first electrogram signal an event occurring within a part of the artifact proximity interval. The part does not overlap the first artifact window.

Furthermore, in accordance with another preferred embodiment of the present invention, the proximity artifact interval partially overlaps the alert window period.

Furthermore, in accordance with another preferred embodiment of the present invention, the proximity interval initiating event is the first event detected within the duration of the first artifact window.

Furthermore, in accordance with another preferred embodiment of the present invention, more than one event is detected within the duration of the first artifact window, and the proximity interval initiating event is the last event detected within the duration of the first artifact window.

Furthermore, in accordance with another preferred embodiment of the present invention, a plurality of events is detected within the duration of the first artifact window, and the proximity interval initiating event is a single event selected from the plurality of events.

Furthermore, in accordance with another preferred embodiment of the present invention, the proximity interval initiating event is an event detected within the duration of the first artifact window using a detection method based on an analysis of morphological parameters of the first electrogram signal.

Furthermore, in accordance with another preferred embodiment of the present invention, the device further includes storage means for storing a plurality of parameter sets associated with at least one of the first artifact window, the alert window, the refractory period, and the cardiac contractility modulating signal.

Furthermore, in accordance with another preferred embodiment of the present invention, the device further includes means for automatically selecting a parameter set associated with at least one of the first artifact window, the alert window, the refractory period, and the cardiac contractility modulating signal. The selecting is based on events selected from: events associated with pacing of the at least second cardiac chamber, events associated with intrinsic activation of the at least second cardiac chamber, and any combination thereof. There is further provided, in accordance with another preferred embodiment of the present invention, a device for controlling the delivery of a nonexcitatory cardiac contractility modulating signals to a heart within a cardiac beat cycle. The device includes at least one sensing unit for sensing electrical activity in or about a first cardiac chamber to provide a first electrogram signal, and for sensing electrical activity in at least a second cardiac chamber to provide at least a second electrogram signal, at least one detecting unit adapted to detect electrical events in the first electrogram signal and in the at least second electrogram signal, a cardiac contractility modulating unit for delivering cardiac contractility modulating signals to the heart, and at least one controller unit operatively connected to the sensing unit, the detecting unit, and to the cardiac contractility modulating unit. The controller unit is adapted to provide a first artifact window within the current beat cycle. The first artifact window starts at or after a trigger event representing the beginning of the current cardiac beat cycle. The first artifact window has a first artifact window duration. The controller unit is adapted to detect events occurring in the first electrogram signal within the duration of the first artifact window. The controller unit is adapted to provide an alert window period within the current beat cycle for enabling the delivery of a cardiac contractility modulating signal to the heart by the cardiac contractility modulating unit within the current beat cycle in response to an enabling event detected in the first electrogram signal within the duration of the alert window period. The alert window period has a first duration and is delayed from the trigger event. The delivery of the cardiac contractility modulating signal is delayed from the time of detecting of the enabling event occurring within the duration of the alert window period by a first delay period. The controller unit is adapted to provide a refractory period within the current beat cycle in response to the enabling event, to prevent the detection of electrical events within the duration of the refractory period. The refractory period has a beginning time and an ending time. The beginning time of the refractory period is delayed from the enabling event by a second delay period. The ending time of the refractory period occurs at or after the termination of the cardiac contractility modulating signal. The controller unit is adapted to control the applying by the cardiac contractility modulating unit of the cardiac contractility modulating signal to the heart within the current beat cycle. The controller unit is adapted to inhibit the providing of the refractory period and the delivery of the cardiac contractility modulating signal within the current beat cycle, in response to detecting an inhibiting event within the first electrogram signal.

Furthermore, in accordance with another preferred embodiment of the present invention, the device includes a memory unit operatively connected to the controller unit for storing data within the device.

Furthermore, in accordance with another preferred embodiment of the present invention, the device includes a communication unit operatively connected to the controller unit for communicating data to and from the memory unit.

Furthermore, in accordance with another preferred embodiment of the present invention, the device includes an implantable electrode operatively connected to the sensing unit for performing sensing in the first cardiac chamber. The device also includes at least one electrode operatively connected to the sensing unit for performing sensing in at least the second cardiac chamber. The device further includes at least one electrode operatively connected to the cardiac contractility modulating unit for applying the cardiac contractility modulating signals to the heart.

Furthermore, in accordance with another preferred embodiment of the present invention, the device includes a pacing unit operatively connected to the controller unit, for pacing at least one cardiac chamber of the heart.

Furthermore, in accordance with another preferred embodiment of the present invention, the device further includes at least one implantable electrode operatively connected to the pacing unit for pacing at least one cardiac chamber of the heart.

Furthermore, in accordance with another preferred embodiment of the present invention, the detecting unit is included within the controller unit.

Furthermore, in accordance with another preferred embodiment of the present invention, the controller unit is adapted for inhibiting the delivery of a cardiac contractility modulating signal to the heart within the next cardiac beat cycle following the current beat cycle, in response to detecting in the first electrogram signal an event within the duration of a sensing time period starting after the end of the refractory period of a beat cycle in which a cardiac contractility modulating signal is delivered to the heart and ending at the end of the current beat cycle in which the cardiac contractility modulating signal is delivered to the heart.

Furthermore, in accordance with another preferred embodiment of the present invention, the controller unit is adapted for inhibiting the delivery of a cardiac contractility modulating signal to the heart within the next cardiac beat cycle following the current beat cycle, in response to detecting by the detecting unit in the first electrogram signal an event within the duration of a sensing time period starting after the end of the alert window and ending at the end of the first delay period, wherein the delivery of a cardiac contractility modulating signal to the heart within the current beat cycle was inhibited in the current beat cycle.

Furthermore, in accordance with another preferred embodiment of the present invention, the at least one inhibitory event includes a single event or any combination of events selected from the group of events consisting of: an event detected by the detecting unit in the first electrogram signal within the time interval between the ending time of the first artifact window and the starting time of the alert window period; an event detected by the detecting unit in the first electrogram signal within the duration of the alert window period after the time of detection of the first event of the step of enabling; and an event detected by the detecting unit within the time interval starting after the end of the alert window period and ending at the beginning time of the refractory period.

Furthermore, in accordance with another preferred embodiment of the present invention, the controller unit is adapted for providing an artifact proximity interval. The artifact proximity interval starts at the time of detection of a proximity interval initiating event detected within the first artifact window and has an artifact proximity interval duration. The controller unit is further adapted to inhibit the providing of the refractory period and to inhibit the applying of the cardiac contractility modulating signal, in response to the detecting, by the detecting unit, in the first electrogram signal an event occurring within a part of the artifact proximity interval. The part of the artifact proximity interval does not overlap the first artifact window.

Furthermore, in accordance with another preferred embodiment of the present invention, the proximity artifact interval partially overlaps the alert window period.

Furthermore, in accordance with another preferred embodiment of the present invention, the proximity interval initiating event is the first event detected within the duration of the first artifact window.

Furthermore, in accordance with another preferred embodiment of the present invention, more than one event is detected within the duration of the first artifact window, and the proximity interval initiating event is the last event detected within the duration of the first artifact window.

Furthermore, in accordance with another preferred embodiment of the present invention, a plurality of events is detected within the duration of the first artifact window, and the proximity interval initiating event is a single event selected from the plurality of events.

Furthermore, in accordance with another preferred embodiment of the present invention, the proximity interval initiating event is an event detected within the duration of the first artifact window using a detection method based on an analysis of morphological parameters of the first electrogram signal.

Furthermore, in accordance with another preferred embodiment of the present invention, the controller unit is adapted to provide a second artifact window period within the current beat cycle in response to a first timing event and to ignore all events detected in the first electrogram signal within the duration of the second artifact window period in order to avoid inhibiting the delivery of the cardiac contractility modulating signal within the current beat cycle by the detection of an expected electrical artifact signal within the duration of the second artifact window period.

Furthermore, in accordance with another preferred embodiment of the present invention, the first timing event detected by the detecting unit is an event detected by the detecting unit in the second electrogram signal. The first timing event is associated with electrical activation of the at least second cardiac chamber.

Furthermore, in accordance with another preferred embodiment of the present invention, the first timing event detected by the detecting unit is an event associated with pacing of the at least second cardiac chamber.

Furthermore, in accordance with another preferred embodiment of the present invention, the first timing event detected by the detecting unit is a pacing command signal associated with pacing of the at least second cardiac chamber.

Furthermore, in accordance with another preferred embodiment of the present invention, the second artifact window period provided by the controller unit partially overlaps the alert window period.

Furthermore, in accordance with another preferred embodiment of the present invention, the controller unit is adapted to provide a third artifact window period within the current beat cycle in response to a second timing event, and to ignore all events detected in the first electrogram signal within the duration of the third artifact window period in order to avoid inhibiting the delivery of a cardiac contractility modulating signal within the next beat cycle following the current beat cycle by the detection of an expected electrical artifact signal within the duration of the second artifact window period.

Furthermore, in accordance with another preferred embodiment of the present invention, the second timing event is an event detected by the detecting unit in the second electrogram signal, the second timing event is associated with electrical activation of the second cardiac chamber.

Furthermore, in accordance with another preferred embodiment of the present invention, the second timing event detected by the device is an event associated with pacing of the at least second cardiac chamber.

Furthermore, in accordance with another preferred embodiment of the present invention, the second timing event detected by the device is a pacing command signal associated with pacing of the second cardiac chamber.

Furthermore, in accordance with another preferred embodiment of the present invention, the device further includes a memory unit operatively connected to the controller unit for storing a plurality of parameter sets associated with at least one of the first artifact window, the alert window, the refractory period, and the cardiac contractility modulating signal.

Finally, in accordance with another preferred embodiment of the present invention, the controller unit is adapted for automatically selecting from the plurality of parameter sets at least one parameter set associated with the at least one of the first artifact window, the alert window, the refractory period, and the cardiac contractility modulating signal. The selecting is based on at least one event selected from events associated with pacing of the at least second cardiac chamber, events associated with intrinsic activation of the at least second cardiac chamber, and any combination thereof.

BRIEF DESCRIPTION OF THE DRAWINGS

The invention is herein described, by way of example only, with reference to the accompanying drawings, in which like components are designated by like reference numerals, wherein.

DETAILED DESCRIPTION OF THE INVENTION

Notation Used Throughout

The following notation is used throughout this document.

| Term | Definition |
| --- | --- |
| CCM | Cardiac Contractility Modulation |
| CHF | Congestive Heart Failure |
| CS | Coronary Sinus |
| ETC | Excitable Tissue Control |
| GCV | Great Cardiac Vein |
| IEGM | Intra-cardiac Electrogram |
| LV | Left ventricle |
| PAC | Premature Atrial Contraction |
| PE | Paced Event |
| PVC | Premature Ventricular Contraction |
| RA | Right atrium |
| RV | Right ventricle |
| SE | Sensed Event |
| SVC | Superior Vena Cava |

Typically, ETC signal delivery is timed relative to a sensed signal representing the depolarization wave locally sensed at or near the site of the electrodes used for ETC signal delivery. This signal may be a biphasic or polyphasic intra-cardiac electrogram (IEGM) signal sensed by a lead or catheter including one or more electrodes capable of sensing an IEGM signal and of delivering pacing pulses. The depolarization wave represented by the IEGM is an electrical event caused by spreading myocardial electrical excitation evoked by the natural pacemaker of the heart (normally the Sino-atrial node) in which case the event is referred to as a sensed event (SE), or by a pacing pulse delivered to the myocardium by, in which case the event is referred to as a paced event (PE). The IEGM signal may also include electrical depolarizations caused by ectopic myocardial activation such as premature atrial contractions (PAC) or premature ventricular contraction (PVC). Furthermore, the IEGM signal may include artifacts caused by electrical noise.

Figure 1:
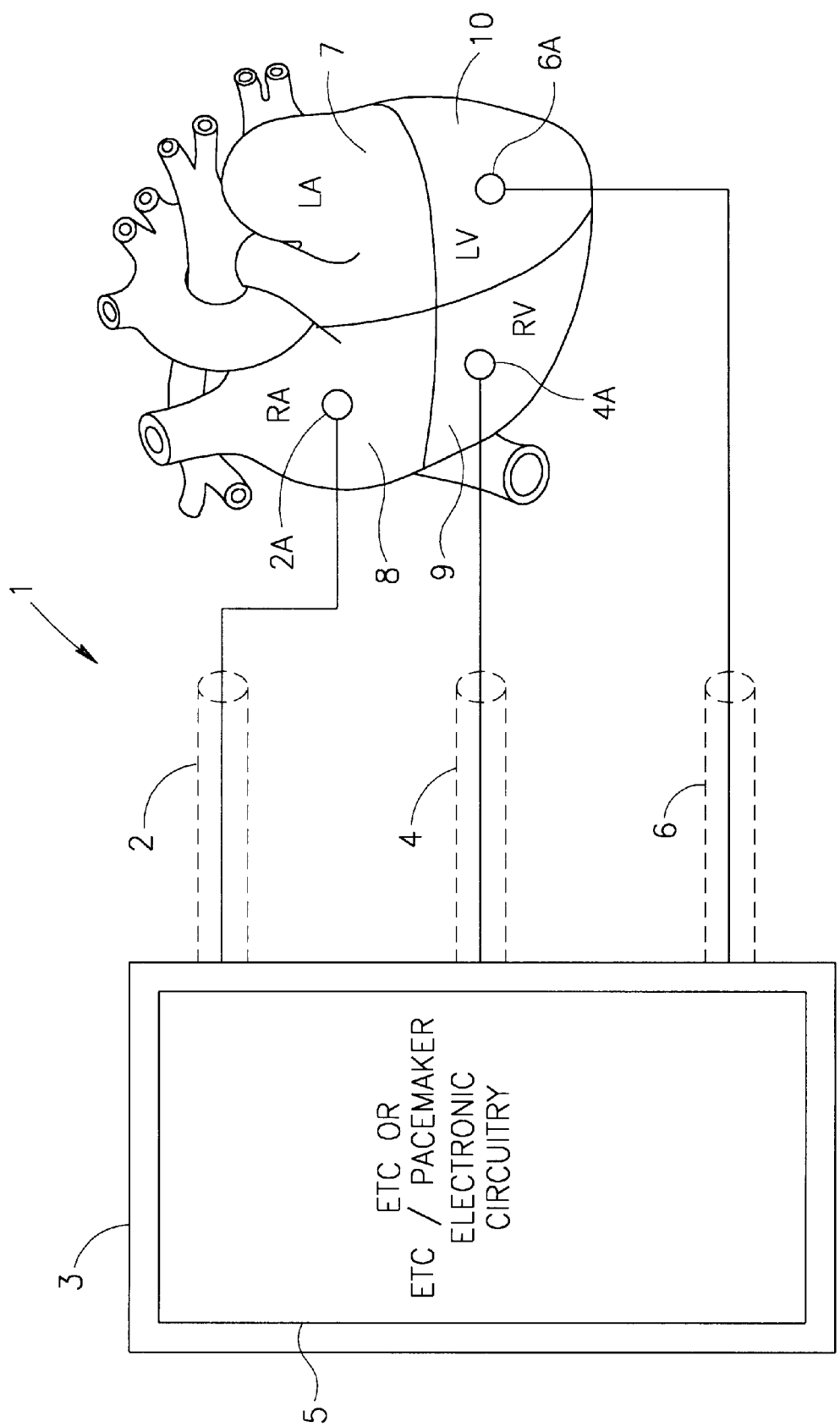
FIG. 1 is a schematic diagram representing a typical lead placement configuration of an ETC device for delivering ETC non-excitatory signals to the heart, in accordance with a preferred embodiment of the present invention.

Reference is now made to FIG. 1 which is a schematic diagram representing a typical lead placement configuration of an ETC device for delivering ETC non-excitatory signals to the heart, in accordance with a preferred embodiment of the present invention. The device 1 may be an ETC device capable of delivering non-excitatory ETC signals to the heart, or an ETC/pacemaker device capable of delivering non-excitatory ETC signals to the heart and of pacing the heart if necessary. The device 1 includes an implantable housing or case 3 for housing the electronic circuitry 5 of the ETC or ETC/pacemaker device (not shown in detail in FIG. 1) of the device 1 which is illustrated in detail hereinafter. A pacing/sensing lead 2 is suitably connected to the case 3 and operatively connected to the circuitry 5.

The lead 2 includes an electrode 2A applied to the right atrium (RA) 8. The electrode 2A is used for sensing SEs and for delivering pacing pulses if necessary. The left atrium 7 (LA) is also shown in FIG. 1. The pacing lead 2 may be inserted into the RA 8 through the sub-clavian vein and the superior vena cava (SVC), but other methods of insertion are also possible. Another pacing/sensing lead 4 is connected to the case 3 and operatively connected to the circuitry 5. The lead 4 includes an electrode 4A which is applied the right ventricle (RV) 9 and is used for sensing right ventricular SEs and PEs and for delivering pacing pulses if necessary. The lead 4 may be inserted into the RV through the subclavian vein and the superior vena cava (SVC), but other methods of insertion are also possible. A third lead 6 is also suitably connected to the case 3 and operatively connected to the circuitry 5. The lead 6 includes an electrode 6A which is applied to the wall of a lateral vein of the great cardiac vein (GCV) and is used for local sensing of SEs and PEs in the left ventricle (LV) 10 and for delivering non-excitatory ETC signals to the LV 10 if required.

The lead 6 may be inserted through the sub-clavian vein, passing through the SVC, the right atrium, the coronary sinus (CS) and the GCV and reaching a lateral vein of the GCV, but other methods of insertion of the leads 6 into or about the left ventricle (LV) are also possible. The implantable case 3 is typically implanted in a thoracic subcutaneous pocket (not shown), but other implantation positions are also possible. It is noted that the above disclosed lead placements and insertion paths and the case placement are given by way of example only and that other electrode placements and lead insertion paths and case placements are also possible.

It is noted that while each of the single electrodes 2A, 4A and 6A of the device 1 of FIG. 1 may be used for sensing with respect to a common reference point such as the case 3 of the device 1, other preferred embodiments of the present invention may use pairs of locally applied electrodes (not shown) which may be used for local differential sensing. For example, The lead 2 may include a pair of electrodes (not shown) which are applied to the RA 8 for local sensing, the lead 4 may include a pair of electrodes (not shown) which are applied to the RV 9 for local sensing and the lead 6 may include a pair of electrodes (not shown) which are applied to the LV 10 for local sensing.

It is further noted that while the electrode 2A of the lead 2 is used for both sensing and pacing the RA 8, in other preferred embodiments of the present invention the lead 2 may include additional electrodes or electrode pairs (not shown) such that one or more electrode or electrode pair is used for sensing in the RA 8 while other separate electrode (s) or electrode pairs are used for pacing the RA 8. Similarly, in accordance with a preferred embodiment of the present invention, The lead 4 may include more than one electrode or pair of electrodes (not shown) which may be separately used for sensing and for pacing the right ventricle 9. Yet similarly, The lead 6 may include more than one electrode or electrode pairs (not shown) of which one or more electrode or electrode pair is used for sensing in the left ventricle 10 and one or more additional electrodes or electrode pairs are used for delivering non-excitatory ETC signals to the left ventricle 10.

It will therefore be appreciated by those skilled in the art, that the number and arrangement of the electrodes within the leads 2,4 and 6 may be varied in many ways and many combinations all being within the scope and spirit of the present invention.

Various types of electrodes and electrode positioning methods known in the art may be used for sensing and pacing and for delivering ETC signals to the heart. One or more of the electrodes or electrode pairs 2A, 4A and 6A may be implanted within a cardiac chamber and placed in contact with the endocardium as disclosed hereinabove. One or more of the electrodes or electrode pairs 2A, 4A and 6A may also be disposed within a cardiac blood vessel, such as a lateral vein of the GCV or another suitable cardiac blood vessel, and used for sensing and/or pacing and/or delivering ETC signals to the myocardial tissue adjacent to or in contact with the blood vessel wall. One or more of the electrodes or electrode pairs 2A, 4A and 6A may also be epicardial electrodes which may be epicardially applied to the heart as is well known in the art.

Typically, ETC signals are delivered to the left ventricle via the electrode(s) 6A of lead 6. The timing of the ETC signal is triggered by locally sensing in the LV the depolarization wave of the PE or the SE, using the sensing/pacing electrode(s) 6A of the lead 6. The sensing/pacing electrode (s) 6A of the lead 6 is also used as the ETC delivery electrode.

To facilitate correct timing of the ETC delivery, measures need to be taken so that ETC signal delivery is not triggered by local LV sensing of noise, premature ventricular contractions (PVCs), premature atrial contractions (PACs) or by delayed sensing of remote events such as a right ventricular depolarization. One possible approach is the restricting of the local sense triggering for ETC delivery to a predefined time window.

The use of a predefined time window for other different purposes such as to detect activation for capture verification in pacemakers is known in the art. U.S. Pat. No. 5,443,485 to Housworth et al. discloses the use of a timing window to detect a paced stimulation pulse for achieving capture verification to ensure that the pacing pulse energy is high enough.

U.S. Pat. No. 5,683,431 to Wang discloses a method for performing pacemaker capture verification using electrodes different than the pacing electrodes to sense the activation evoked by the pacing pulse.

U.S. Pat. No. 5,391,192 to Lu et al. discloses a method for externally determining the minimum energy of a pacing pulse for capture verification using window based detection of activation.

Figure 2:
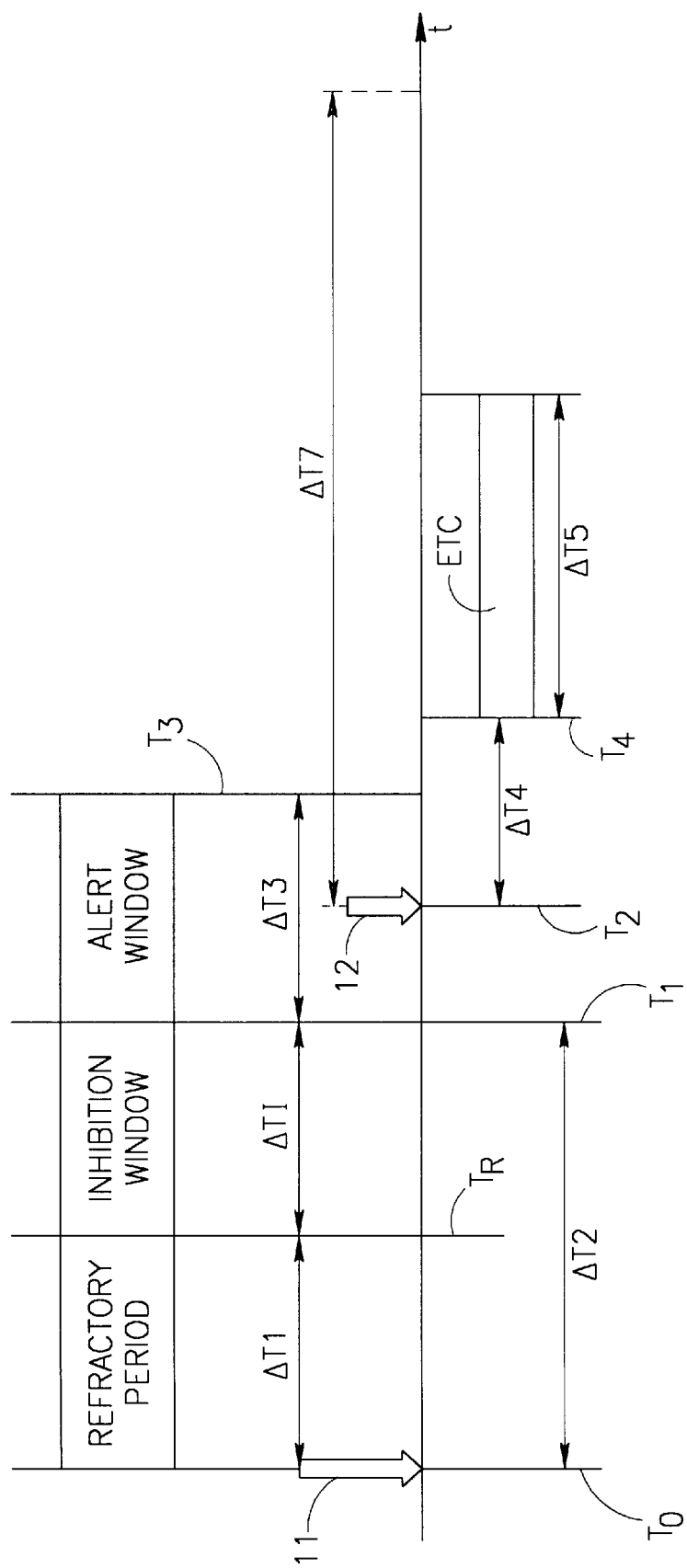
FIG. 2 is a schematic diagram useful in understanding the method of using an alert window for timing the delivery of ETC signals useful in operating the device of FIG. 1, in accordance with a preferred embodiment of the present invention.

Reference is now made to FIG. 2 which is a schematic diagram useful in understanding a method using an alert window for timing the delivery of ETC signals useful in operating the device of FIG. 1 (or of the devices of FIGS. 3–6), in accordance with a preferred embodiment of the present invention. The detection time window is referred to as the "alert window" throughout the present application.

The horizontal axis of FIG. 2 represents time. The arrow labeled 11 schematically represents the timing of a depolarization event 11 locally sensed in the RV by one or more electrodes (not shown) of the lead 4 of FIG. 1. The time $T_0$ represents the time of detection of the RV event. Typically, the time $T_0$ represents the time point at which a threshold crossing occurs. However, $T_0$ may also represent the time of event detection obtained by other methods known in the art for cardiac event detection such as detection methods based on the shape of the signal (also known as signal morphology based detection methods) or other suitable detection methods known in the art. The RV event 11 may represent a locally sensed RV depolarization initiated by a naturally occurring SA node evoked atrial event (not shown) or initiated by artificial atrial pacing. The RV event 11 may also represent a locally sensed RV depolarization initiated by a pacing pulse delivered to the RV through an electrode (not shown) included in the lead 4 of FIG. 1. After the time $T_0$, a local sense "refractory" period labeled $\Delta T1$ begins. The refractory period $\Delta T1$ ends at time $T_R$. During the refractory period $\Delta T1$ no sensing is performed. This refractory period is used to avoid the electrical pacing artifact due to electrode polarization and/or electrode cross-talk. The refractory period may also be useful in avoiding electrical artifacts due to far field sensing as is well known in the art.

Typically, the duration of the refractory period $\Delta T1$ is approximately 10–15 milliseconds but other values may be used depending, inter alia, on the specific application, electrode type, and detection method used. It is noted that, in accordance with one preferred embodiment of the present invention, the value of the refractory period duration may be set to $\Delta T1=0$. In such an embodiment no refractory period $\Delta T1$ is implemented.

A local sense alert window having a duration $\Delta T3$ starts at time $T_1$ and ends at time $T_3$. The time interval between time points $T_0$ and $T_1$ is defined as the alert window delay interval $\Delta T2$ which is the delay between time of detection of the depolarization event 11 and the beginning of the alert window $\Delta T3$.

The arrow labeled 12 of FIG. 2 schematically represents the occurrence of a depolarization event locally sensed in the LV. For example, the locally sensed event 12 may be sensed by a sensing electrode (not shown) or by an ETC signal delivery electrode (not shown) included within the lead 6 of FIG. 1. The time $T_2$ represents the time of detection of the LV depolarization event 12. Typically, the time $T_2$ represents the time point at which a threshold crossing occurs as is disclosed hereinbelow. However, $T_2$ may also represent the time of event detection obtained by other methods known in the art for cardiac event detection.

An article titled "NEURAL NETWORK BASED ADAPTIVE MATCHED FILTERING FOR QRS DETECTION" by Xue et al., published in IEEE Transactions on Biomedical engineering, Vol. 39, No. 4 pp. 317–329 (1992) and incorporated herein by reference, discloses an adaptive matched filtering algorithm based on an artificial neural network for QRS detection.

An article titled "IDENTIFICATION OF VENTRICULAR TACHYCARDIA WITH USE OF THE MORPHOLOGY OF THE ENDOCARDIAL ELECTROGRAM" by Langberg et al., published in Circulation, Vol. 77, No. 6 pp. 1363–1369 (1988) and incorporated herein by reference, discloses the application of a template to derive morphological parameters of unipolar and bipolar electrogram signals for detecting tachycardia.

An article titled "CLASSIFICATION OF CARDIAC ARRHYTHMIAS USING FUZZY ARTMAP" by F. M. Ham and S. Han, published in IEEE Transactions on Biomedical engineering, Vol. 43, No. 4 pp. 425–430 (1996) and incorporated herein by reference, discloses the use of a fuzzy adaptive resonance theory mapping (ARTMAP) neural net classifier for classifying QRS complexes under normal and abnormal conditions.

U.S. Pat. No. 5,782,876 to Flammang titled "METHOD AND APPARATUS USING WINDOWS AND AN INDEX VALUE FOR IDENTIFYING CARDIAC ARRHYTHMIAS", incorporated herein by reference, discloses the use of the sensed electrogram slope (derivative of ECG) for morphological electrogram detection in a device for identifying cardiac arrhythmias.

The above referenced morphological signal detection methods, as well as other signal morphology based detection methods known in the art, may be adapted for detection of the depolarization events within the IEGM signals of the present invention.

The detection of the LV sensed event 12 at time $T_2$ triggers the delivery of an ETC signal represented by the cross hatched area labeled ETC. The ETC signal starts at a time point $T_4$ separated from $T_2$ by a delay interval $\Delta T4$. The ETC signal has a duration $\Delta T5$.

Preferably, the value of the duration of the ETC signal $\Delta T5$ is a variable duration and may vary from one beat cycle to another in accordance with the required modification of myocardial contractility. Typically, the duration and or other parameters of the ETC signal may be modified based on the current value of the heart rate. The methods for determining the required ETC signal duration $\Delta T5$ are not the subject matter of the present invention and will not be disclosed in detail hereinafter.

It is noted that, in accordance with other preferred embodiments of the present invention, the duration of the ETC signal $\Delta T5$ may be a constant value which does not vary from one beat cycle to another beat cycle.

The ETC signals may have various waveforms, durations and intensities as disclosed in detail by Ben Haim et al. in the above referenced International Publications No. WO 97/25098, WO 98/10828, WO 98/10829, WO 98/10830, WO 98/10831 and WO 98/10832. The characteristics of the delivered ETC signals are not the subject of the present invention and will not be further discussed hereinafter.

Only a locally sensed depolarization event detection occurring within the duration of the alert window $\Delta T3$ is used to trigger an ETC signal. The detection of an electrical depolarization event happening outside the alert window will not result in triggering of an ETC signal. This has the advantage of reducing the probability of delivering an improperly timed ETC signal due to electrical noise occurring outside the preset duration of the alert window $\Delta T3$. However, if a depolarization event (not shown) due to an ectopic beat is detected between the time $T_0$ and the time $T_1$ in a case where the refractory period $\Delta T1$ is not used, or between the time $T_R$ and the time $T_1$ in a case where the refractory period $\Delta T1$ is used, and then a later depolarization event (not shown) is detected within the duration of the alert window $\Delta T3$, the triggering of an ETC signal by the later occurring depolarization event may result in an improperly timed ETC signal. Therefore, In order to prevent such improper timing, the timing method may further include an inhibitory window $\Delta TI$. Any depolarization event which is detected within the duration of the inhibition window $\Delta TI$ will result in the inhibiting of ETC signal delivery within the current beat cycle as disclosed in detail hereinbelow.

In accordance with one preferred embodiment of the present invention, $\Delta TI=\Delta T2-\Delta T1$, in such a preferred embodiment the inhibition window $\Delta TI$ starts at the end of the refractory period $\Delta TI$ and ends at the beginning of the alert window $\Delta T3$. If no refractory period is used ($\Delta T1=0$), the inhibition window spans the entire alert window delay interval $\Delta T2$. However, in accordance with other preferred embodiments of the timing method of present invention, the end of the inhibition period $\Delta TI$ may be separated from the beginning of the alert window $\Delta T3$ by an intermediate time interval (not shown in FIG. 2 for the sake of clarity of illustration). The detection of a depolarization event within the duration of such an intermediate time interval will not result in the inhibition of triggering of an ETC signal by a later depolarization event detected within the duration of the alert window $\Delta T3$.

If a depolarization event was detected in the IEGM signal which is locally sensed in the left ventricle 10 within the duration of the inhibition window $\Delta TI$, ETC signal delivery is inhibited such that later occurrence of a depolarization event within a preset "inhibition refractory period" (not shown in FIG. 2 for the sake of clarity of illustration) of the current beat cycle will not result in a delivery of an ETC signal. This feature has the advantage that it reduces the probability of erroneous detection of spurious noise or of ectopic beats such as PVCs or PACs and the subsequent triggering of the delivery of an incorrectly timed ETC signal. The details of the implementation of the inhibition refractory period are disclosed in detail hereinafter (with reference to FIG. 7)

Typically, the local sensing sensitivity is adjusted such that, only events of a certain amplitude will be detected. This is achieved by setting a detection threshold. Threshold crossing detection methods for electrical signals are well known in the art and are not the subject matter of the present invention. Such threshold crossing detection methods are commonly used in pacemakers for sensed event detection.

Briefly, any acceptable detection method based on threshold crossing of one or more threshold levels may be used with the present invention. For example, the sensed electrogram may be biphasic, and two threshold levels may be used including a positive threshold level and a negative threshold level. Alternatively, full wave rectification of the electrogram may be used to obtain a signal which is positive only, such that a single positive threshold level may be used. Additionally, other methods of detection may be used which are based on signal morphology as disclosed in detail hereinabove.

Since multiple threshold crossings may occur during the same depolarization event or during noise signals, ambiguity may arise as to which threshold crossing should be used as the trigger. This may be solved by triggering by the first threshold crossing in the window and by implementing an "alert refractory period" $\Delta T7$ following the first threshold crossing of the LV sensed event 12 at time $T_2$ to prevent multiple triggering by multiple threshold crossings occurring within a single depolarization wave representing a single event. The alert refractory period $\Delta T7$ starts at the time $T_2$ and has a fixed duration represented by the double headed arrow labeled $\Delta T7$. During the alert refractory period $\Delta T7$ no sensing is performed so that additional triggering cannot happen during the period $\Delta T7$.

It is noted that, since the first threshold crossing due to an LV sensed event 12 may happen at any time during the alert window $\Delta T3$, and since the duration of the ETC signal $\Delta T5$ may be varied from one beat cycle to another (for varying the effects of the ETC signal on myocardial contraction), the duration of the alert refractory period $\Delta T7$ is set such that it is larger than the sum of the durations of the alert window $\Delta T3$, the delay interval $\Delta T4$ and the maximal allowable duration $\Delta T5_{MAX}$ of the ETC signal. The maximal allowable duration $\Delta T5_{MAX}$ is a preset value.

Thus, $\Delta T7>\Delta T3+\Delta T4+\Delta T5_{MAX}$. This ensures that no further threshold crossings will be sensed and detected after the first threshold crossing detection until the ETC signal has ended, irrespective of the time of occurrence of the first threshold crossing detection $T_2$ within the alert window duration $\Delta T3$ and of the specific duration $\Delta T5$ of the ETC signal delivered within the current beat cycle.

Typically, the duration $\Delta T3$ of the alert window is approximately 30 milliseconds, the duration of the delay interval $\Delta T4$ is approximately in the range of 30–60 milliseconds and the maximal allowable duration $\Delta T5_{MAX}$ of the ETC signal is approximately 20–30 milliseconds. However, other values of $\Delta T3$, $\Delta T4$ and $\Delta T5_{MAX}$ may be used.

A typical value of the duration of the alert refractory period $\Delta T7$ is therefore in the range of approximately 120–200 milliseconds. However, other values of the duration of the alert refractory period $\Delta T7$ may be used depending, inter alia, on the particular values of $\Delta T3$, $\Delta T4$ and $\Delta T5_{MAX}$ used. The duration of the alert refractory period $\Delta T7$ is a preset value and does not change from one beat cycle to another. However, The duration of the alert refractory period $\Delta T7$ may be changed if necessary by appropriately reprogramming the software embedded within the device 1 telemetrically or non-telemetrically (depending on the specific hardware implementation of the device 1).

For the sake of simplicity, the method of the present invention will be disclosed as using a single positive threshold level. A certain positive threshold voltage level is set for the pacemaker/ETC device. A crossing of this threshold level by the IEGM signal occurring within the time interval between $T_R$ and $T_3$ will be detected as an event. For example, the detection threshold may be set as +3.0 millivolts but other suitable threshold levels may be used for detection.

Figure 3:
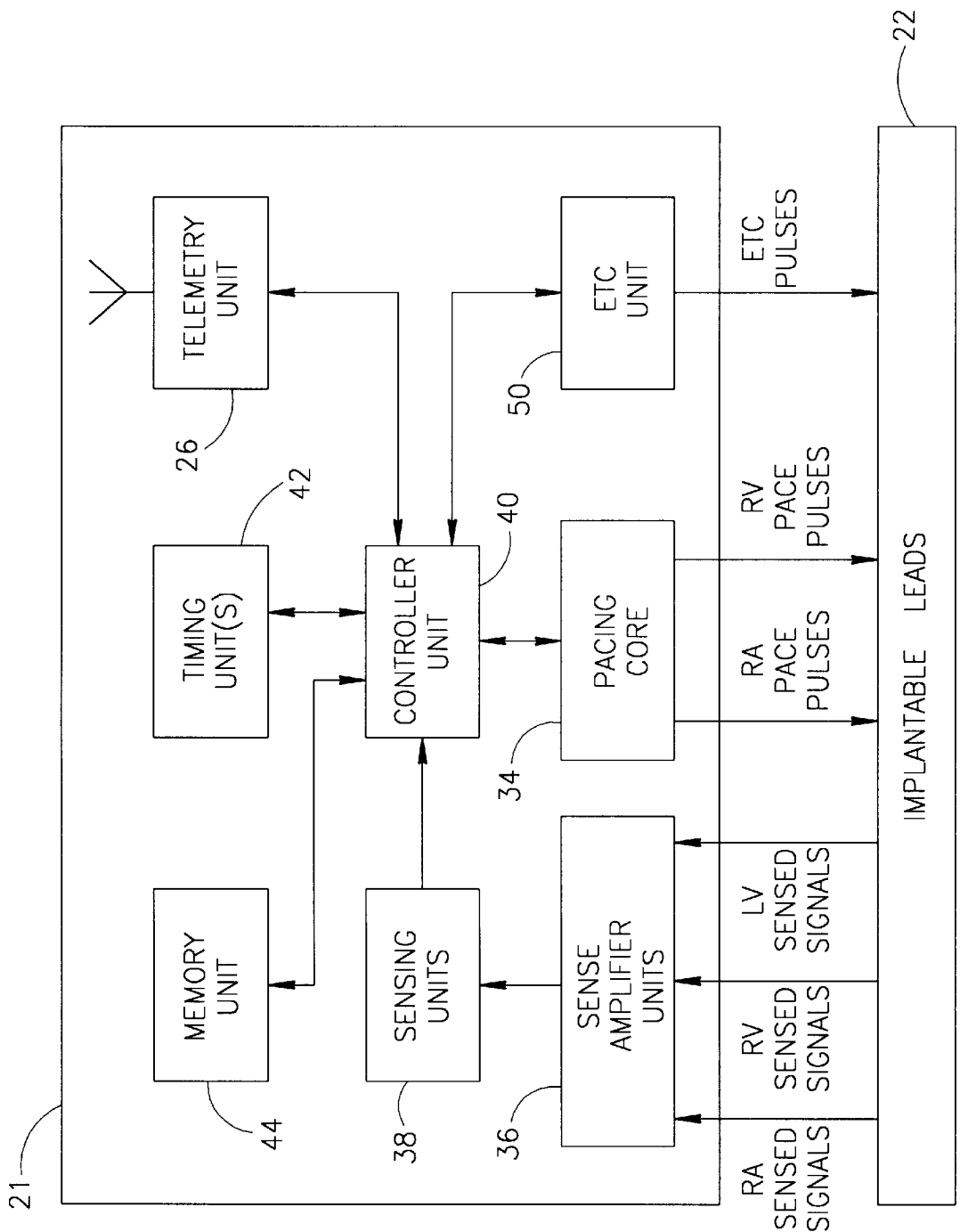
FIG. 3 is a schematic functional block diagram illustrating an implantable device for pacing the heart and for delivering ETC signals to the heart using the method of timing of the non excitatory signal, in accordance with a preferred embodiment of the present invention.

Reference is now made to FIG. 3 which is schematic functional block diagram illustrating an implantable device 21 for pacing the heart and for delivering ETC signals to the heart using the method of timing of the non excitatory signal, in accordance with a preferred embodiment of the present invention. The implanted pacemaker/ETC device 21 includes a pacing core 34 for providing pacing pulses to the RA and RV pacing electrodes (not shown) of the implantable leads 22. The pacemaker/ETC device 21 further includes sense amplifier units 36 for amplifying the RA, RV and LV signals locally sensed by the sensing electrodes (not shown) of the implantable leads 22. For example, when the pacemaker/ETC device 21 represents the pacemaker/ETC device 1 of FIG. 1, one of the sense amplifier units 36 receives the signal locally sensed in the RA 8 from lead 2 of FIG. 1, another of the sense amplifier units 36 receives the signal locally sensed in the RV 9 from lead 4 of FIG. 1 and a third one of the sense amplifier units 36 receives the signal locally sensed in the LV 10 from the lead 6 of FIG. 1.

The pacemaker/ETC device 21 further includes sensing units 38 suitably connected to a controller unit 40. The sensing units 38 receive the amplified locally sensed signals from the amplifier units 36 and provide trigger signals to the controller unit 40 for activating the pacing core as is known in the art. The pacemaker/ETC device 21 further includes timing units 42, connected to the controller unit 40 for providing the controller unit 40 with clock signals, and a memory unit 44 suitably connected to the controller unit 40. The controller 40 can store data in the memory unit 44 and can access the data stored in the memory unit 44 for processing the accessed data and/or for sending data to a telemetry unit 26 for telemetrically communicating the data to a receiving station (not shown) placed outside of the patient. The memory unit 44 may include random access memory (RAM) units (not shown), read only memory (ROM) units (not shown), other suitable type of memory units known in the art, or any suitable combination of memory unit types.

It is noted that the pacemaker/ETC device 21 when connected to implantable leads having the configuration of leads 2, 4, and 6 of FIG. 1, may function, inter alia, as a pacemaker in a DDD mode, including, inter alia, the ability to detect PVCs as is known in the art.

The telemetry unit 26 is used for wirelessly transmitting data stored in memory unit 44 under the control of the controller unit 40. The pacemaker/ETC device 21 further includes an excitable tissue controller (ETC) unit 50. The ETC unit 50 is suitably connected to the controller unit 40 and to one or more ETC electrodes (not shown) within the leads 22. For example, when the pacemaker/ETC device 21 represents the pacemaker/ETC device 1 of FIG. 1, the ETC unit 50 is connected to the ETC signal delivering electrode 6A of the lead 6 of FIG. 1. However in other preferred embodiments of the present invention, the ETC unit 50 may be connected to one or more ETC electrodes or ETC electrode pairs (not shown) which are used for delivering ETC signals. The controller unit 40 controls the delivery of ETC signals to the myocardium by timing the delivery of suitable control signals to the ETC unit 50.

Figure 4:
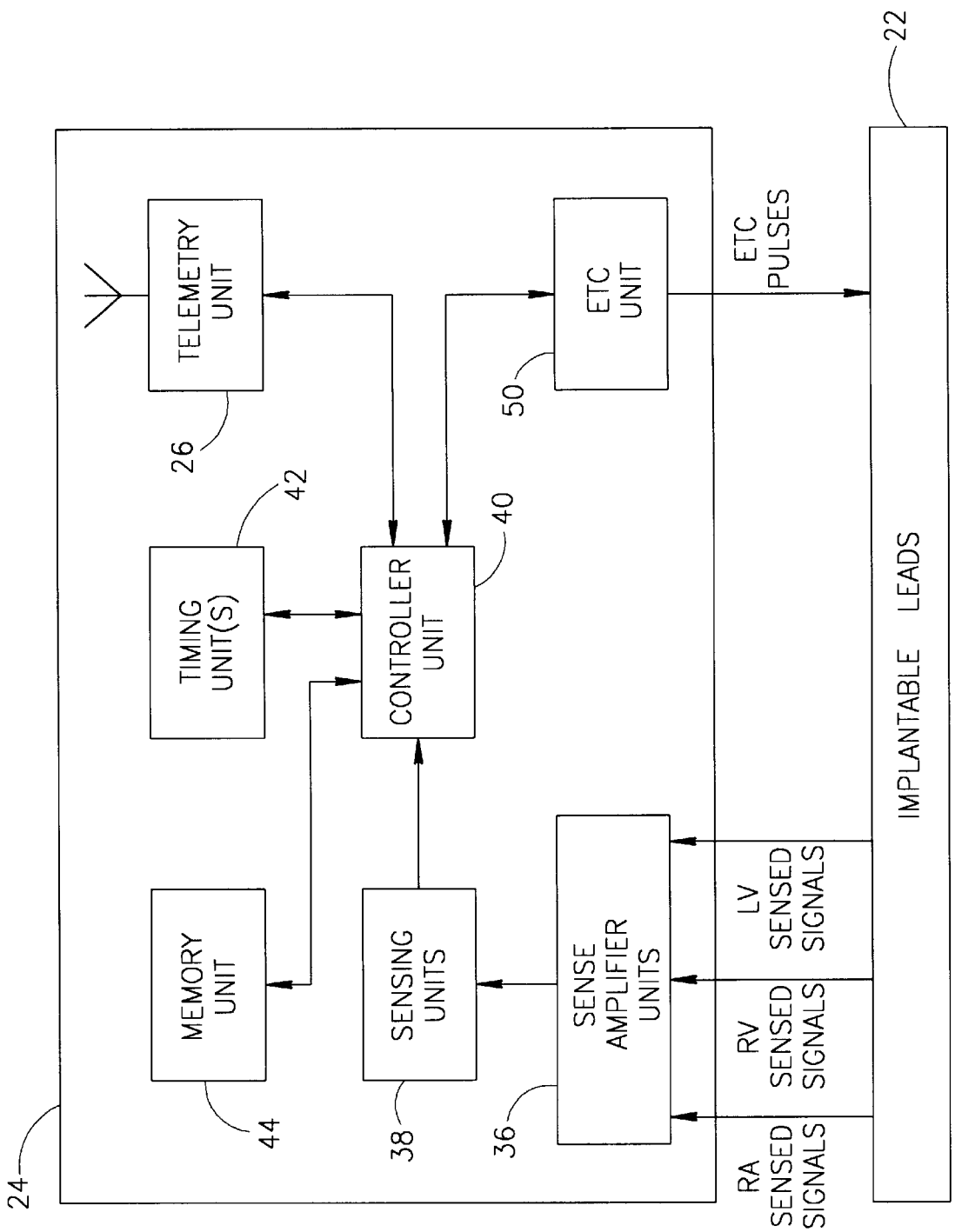
FIG. 4 is a schematic functional block diagram illustrating an implantable device for delivering ETC signals to the heart using the method of timing of the non excitatory signal, in accordance with a preferred embodiment of the present invention.

Reference is now made to FIG. 4 which is schematic functional block diagram illustrating an implantable device for delivering ETC signals to the heart using the method of timing of the non excitatory signal, in accordance with a preferred embodiment of the present invention. The device 24 is similar to the device 21 of FIG. 3 except that it does not include the pacing core 34 of the device 22 of FIG. 3.

The device 24 may be used in patients where ETC signals need to be delivered to the heart but pacing of the heart is not required, such as but not limited to congestive heart failure (CHF) patients. CHF patients may have an unimpaired cardiac conduction system and may exhibit no chronotropic incompetence and no conduction abnormalities or blocks. In the cases where the device 24 is used for delivering ETC signals to the heart, the electrodes (not shown) in the implantable leads 22 are used for sensing and for delivering ETC signals and are not used for pacing the heart.

Figure 5:
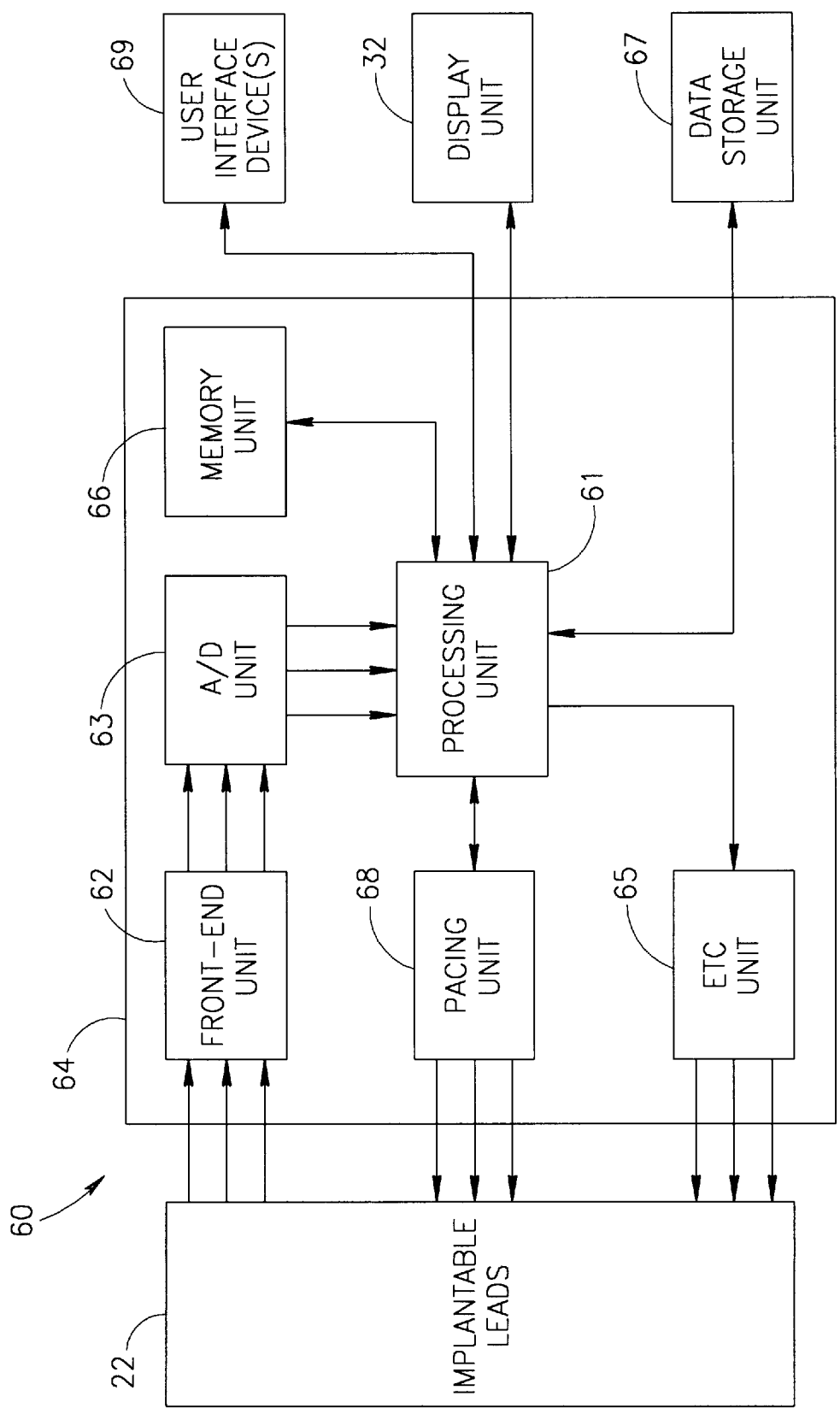
FIG. 5 is a schematic functional block diagram illustrating a system including a non-implanted device and implantable electrodes for pacing the heart and for delivering ETC signals to the heart using the method of timing of the non excitatory signal, in accordance with a preferred embodiment of the present invention.

Reference is now made to FIG. 5 which is schematic functional block diagram illustrating a system including a non-implanted device and implantable electrodes for pacing the heart and for delivering ETC signals to the heart using the method of timing of the non excitatory signal, in accordance with a preferred embodiment of the present invention. The system 60 includes a plurality of implantable leads 22 implanted within a patient (the patient is not shown) and an external ETC device 64. The plurality of implantable leads 22 may include, for example, the leads 2, 4 and 6 of FIG. 1. However, the plurality of leads 22 may include any other suitable combinations of leads including a plurality of sensing, pacing and ETC electrodes (not shown in detail) positioned in two or more chambers of the heart as disclosed for the devices 1, 21 and 24 hereinabove. The plurality of leads 22 are implanted in the patient's heart and are then suitably connected to the ETC device 64 which includes the necessary electronic circuitry for sensing electrical activity in the heart, for pacing the heart if necessary and for delivering ETC non-excitatory signals to the heart using the method of timing the delivery of ETC signals to the heart in accordance with the method of the present invention as disclosed in detail hereinabove and illustrated if FIG. 2 .

The ETC device 64 includes a processing unit 61, a front-end unit 62, an analog to digital converting unit (AID) 63, a pacing unit 68 and an ETC unit 65. The front end unit 62 is suitably connected to one or more of the sensing electrodes of the leads 22 and to the processing unit 61 for pre-conditioning one or more IEGM signals sensed by these one or more sensing electrode. The front-end unit 62 may include suitable circuitry such as one or more amplifier circuits (not shown) for amplifying the IEGM signals sensed by the one or more sensing electrodes. The front-end unit 62 may also include filter circuits (not shown) for filtering the amplified signals prior to digitizing them by the A/D unit 63. The front-end unit 62 is suitably connected to the A/D unit 63 and provides amplified or amplified and filtered IEGM signals thereto for digitizing.

The AND unit 63 may include one or more separate A/D converters (not shown) each A/D converter being dedicated to a single sensing electrode of the one or more sensing electrodes included within one or more of the leads 22. Alternatively, the A/D unit 63 may include a single A/D converter (not shown) suitably connected to a plurality of sensing electrodes of the leads 22 through a multiplexer unit (not shown). The digitized IEGM signals are provided to the processing unit 61 by the A/D unit 63 for further processing. The processing unit 61 digitally performs the detection of events based on the digitized IEGM data provided by the A/D unit 63. The ETC device 64 further includes a memory unit 66 suitably connected to the processing unit 61 for storing data.

The pacing unit 68 is suitably connected to the processing unit 61 and to one or more pacing electrodes of the leads 22. The pacing unit 68 receives control signals from the processing unit 61 for controlling the delivery of pacing pulses to one or more locations in the heart (not shown). The pacing unit 68 includes all the necessary circuitry for delivering pacing pulses to one or more pacing electrodes. Such circuitry is well known in the art and is not shown in detail hereinafter.

It is noted that the ETC device 64 when connected to the implantable leads 22 is capable of performing all the functions of an implanted pacemaker. For example, when the leads 22 have the configuration of leads 2, 4, and 6 of FIG. 1, the ETC device 64 is capable of performing, inter alia, all the functions of an implanted pacemaker in a DDD mode. These functions include, inter alia, the ability of detection of PVCs as is well known in the art.

The ETC unit 65 is suitably connected to the processing unit 61 and to one or more ETC signal delivery electrodes of the implantable leads 22. The ETC unit 65 receives control signals from the processing unit 61 for controlling the delivery of ETC signals to the heart through the one or more ETC delivery electrodes of the implantable leads 22. The ETC unit 65 may be any suitable unit for delivering ETC signals to the myocardium as disclosed by Ben Haim et al. in the above referenced International Publications No. WO 97/25098, WO 98/10828, WO 98/10829, WO 98/10830, WO 98/10831 and WO 98/10832.

The system 60 further includes a display unit 32 suitably connected to the processing unit 61 for displaying graphic symbolic and numerical data processed by the processing unit 61. The data may be presented to the physician or user operating the system 60. The system 60 may further include a data storage unit 67 for storing data. The data storage unit 67 may be any suitable data storage device for storing data on a storage medium such as a magnetic storage medium, an opto-magnetic storage medium, an optical storage medium, a holographic storage medium or any other type of fixed or removable storage medium. Some non-limiting examples of the storage device are, a magnetic hard disk drive, a magnetic floppy disk drive, an opto-magnetic disk drive, an optical disc drive. The data stored on the data storage device may include, inter afia, patient clinical data, patient demographic data, various IEGM data, data including the alert window parameters and any other relevant or desired data. The data storage device may be used for storing data for a plurality of different patients.

The system 60 further includes one or more user interface devices 69 suitably connected to the processing unit 61 through a suitable communication interface (not shown) for enabling the user of the system 60 to input data and commands for controlling the sensing, pacing and ETC signal delivery operation of the ETC device 64. The user interface device(s) 69 may be a keyboard, a pointing device such as a mouse, a light pen in combination with a suitable touch sensitive screen or tablet, or the like or any other suitable device for inputting data or commands to the ETC device 64, or any suitable combination thereof.

In operation after the leads 22 are implanted in the heart of the patients and are connected to the ETC device 64, the ETC device 64 is operative to pace the heart if necessary, and to perform the sensing of IEGM signals and the delivery of ETC signals to the heart using the method for determining the timing of delivery of ETC signals using an alert window and/or inhibition window disclosed in detail hereinabove and illustrated in FIG. 2 . It is noted that the ETC device 64 is capable of performing all the activities of an implanted pacemaker/ETC device such as the pacemaker/ETC device 21 of FIG. 3 except for the telemetry functions. The ETC device 64 may perform cardiac pacing at one or more cardiac locations and may controllably deliver ETC signals to one or more cardiac locations. The performance of the functions of a pacemaker/ETC device by the ETC device 64 may be achieved by using different methods and/or different hardware implementation than the methods and hardware of an implantable pacemaker/ETC device, such as the pacemaker/ETC device 21 of FIG. 3. For example, while in the pacemaker/ETC device 21 the event detection is performed by sensing units 38 which are analog circuits, the event detection in the ETC device 64 is performed by digitally processing the digitized IEGM data provided by the A/D unit 63. Additionally, the pacing unit 68 and the ETC unit 65 may have hardware and software implementations different than those of the pacing core 34 and the ETC unit 50, respectively, of the pacemaker/ETC device 21 because of the physical size and current consumption limitations imposed on the design of the pacing core 34 and the ETC unit 50 of the pacemaker/ETC device 21 due to the dimensional limitations imposed in an implanted device. These limitations are not relevant in the non-implanted ETC device 64. However, functionally, the sensing, pacing and ETC delivery of the ETC device 64 are similar to and may be regarded as simulating the same functions of an implanted of the pacemaker/ETC device, such as, for example, the functions of the pacemaker/ETC device 21 of FIG. 3.

Figure 6:
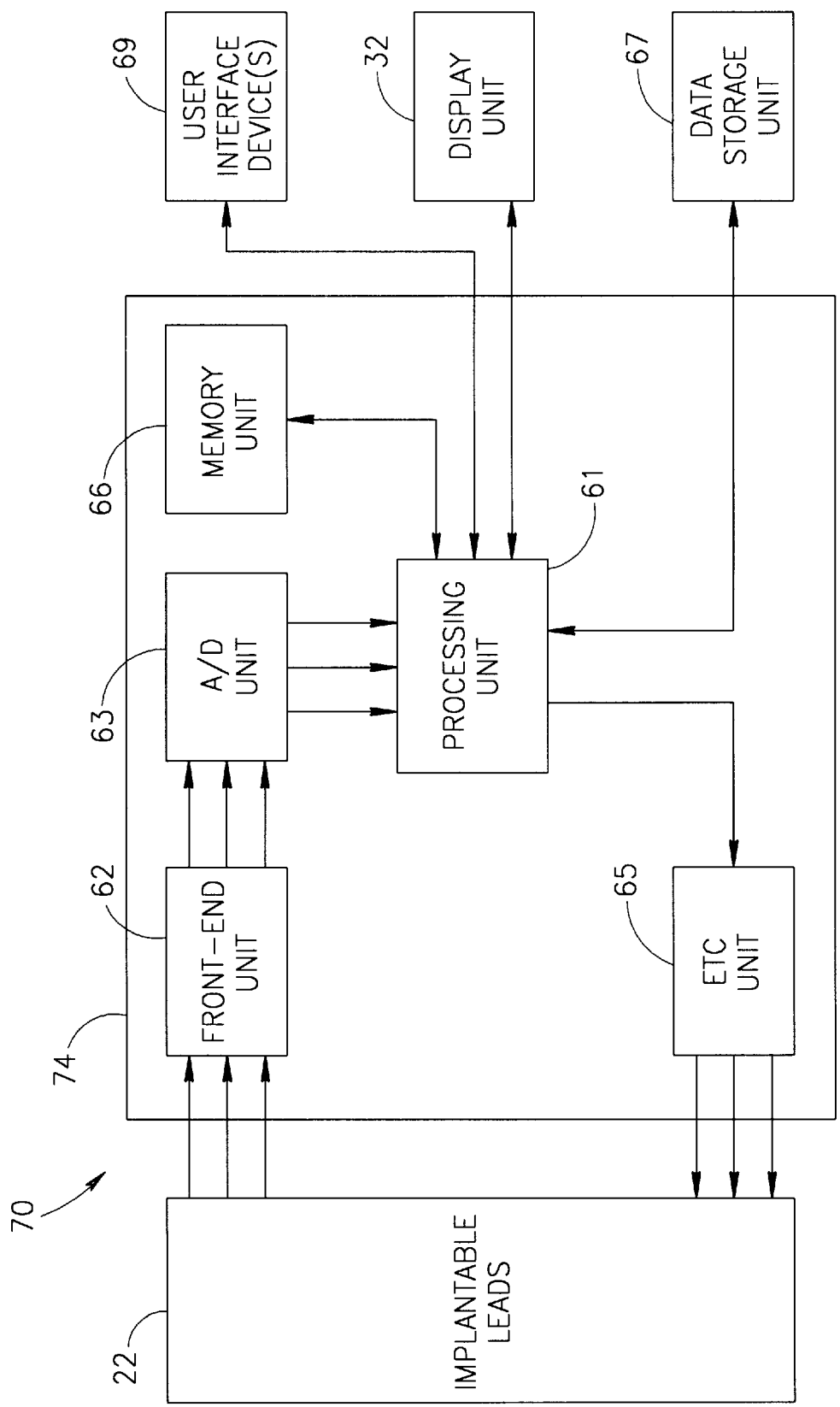
FIG. 6 is a schematic functional block diagram illustrating a system including a non-implanted device having implantable electrodes for delivering ETC signals to the heart using the method of timing of the non excitatory signal, in accordance with a preferred embodiment of the present invention.

Reference is now made to FIG. 6 which is a schematic functional block diagram illustrating a system 70 including a non-implanted device having implantable electrodes for delivering ETC signals to the heart using the method of timing of the non excitatory signal, in accordance with a preferred embodiment of the present invention.

The system 70 includes an ETC device 74 suitably connected to a plurality of implantable leads 22. The ETC device 74 is similar to the ETC device 64 of FIG. 5, except that it does not include the pacing unit 68. The ETC device 74 operates similarly to the ETC device 64, except that it does not have the pacing capacity of the ETC device 64 and is therefore not capable of pacing of the heart.

It is noted that, while the devices 1, 21 and 24 of FIGS. 1, 3 and 4 respectively, and the systems 60 and 70 of FIGS.

5 and 6 respectively, may use the single threshold crossing detection method disclosed in detail hereinabove, all of these devices and systems may use other detection methods. The detection methods for detecting depolarization events in the electrical signals sensed by one or more of the electrodes included in one or more of the implantable leads such as the leads 2, 4, and 6 of the device 1 and the plurality of implantable leads 22 of the devices 21 and 24 and the systems 60 and 70, may include detection methods known in the art for detection of locally sensed cardiac depolarization events based on signal morphology and/or methods based on multiple threshold crossings and/ or signal slope as disclosed hereinabove.

Thus, various detection methods may be used for detecting the first event occurring within the alert window time interval ΔT3 (FIG. 2) as disclosed hereinabove.

Figure 7:
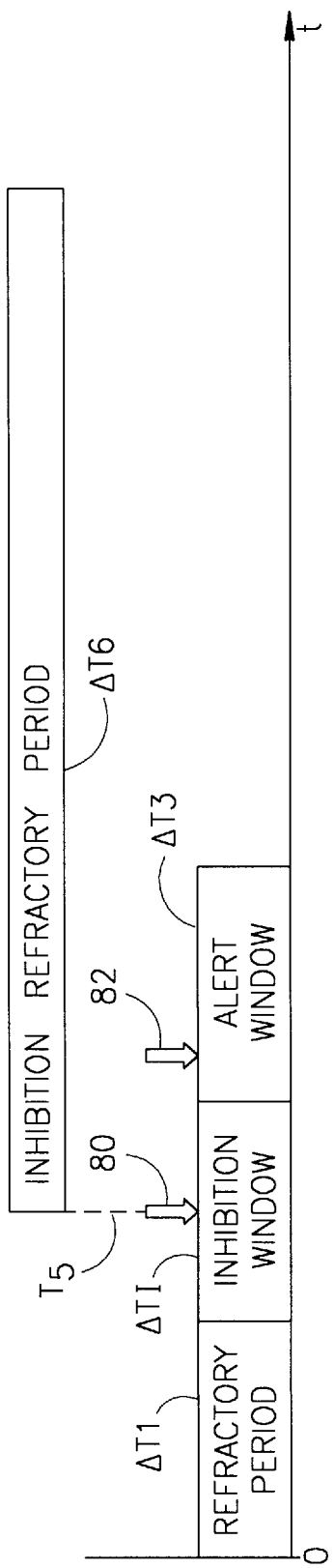
FIGS. 7–8 are schematic diagrams useful in understanding the method of timing of delivery of ETC signals of the present invention.
Figure 8:
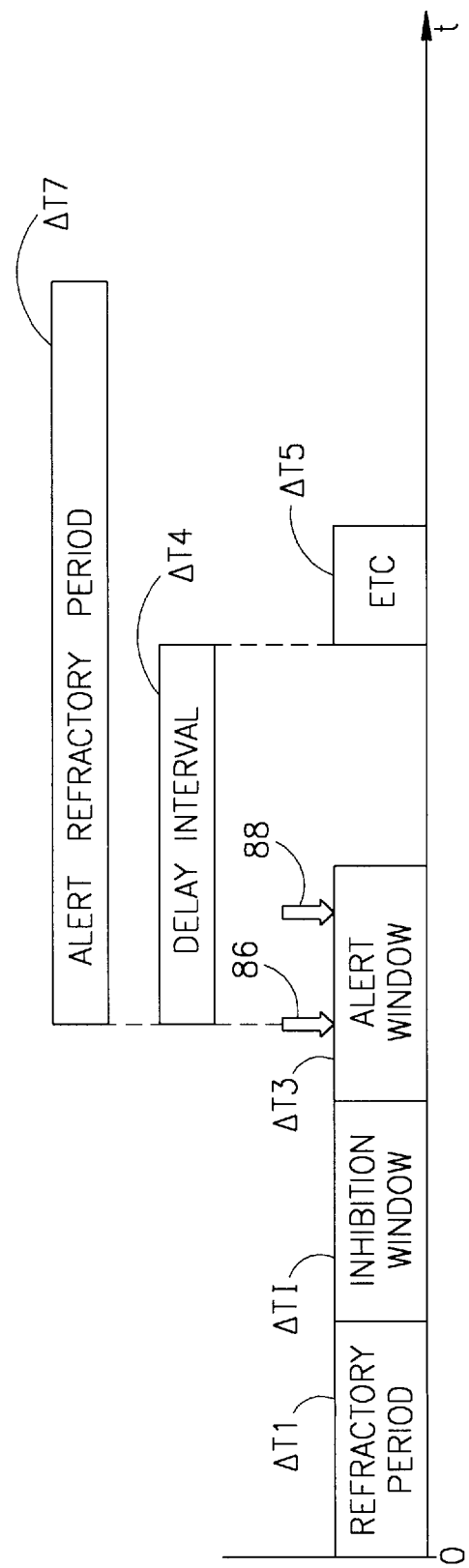

Reference is now made to FIGS. 7 and 8 which are schematic diagrams useful in understanding the method of timing of delivery of ETC signals of the present invention.

In each of FIGS. 7–8, The horizontal axis represents time and the zero time point of the horizontal axis represents the time of detection of a depolarization event locally sensed in the right ventricle 9 (FIG. 1) and is equivalent to the depolarization event 11 of FIG. 2. The refractory period ΔT1, the inhibition window ΔTI, the alert window ΔT3, the delay interval ΔT4, the ETC signal duration ΔT5, and the alert refractory period ΔT7 of FIGS. 7–8 are as disclosed in detail hereinabove, and illustrated in FIG. 2.

In FIG. 7, the arrow labeled 80 represents a depolarization event 80 locally sensed in the left ventricle 10 and detected at the time point represented by the dashed line labeled $T_5$. The arrow labeled 82 represents the time of occurrence of another depolarization 82 occurring in the left ventricle 10 at a time point which falls within the duration of the alert window ΔT3. The time of detection of the depolarization event 80 falls within the duration of the inhibition window ΔTI. Therefore, the delivery of an ETC pulse in response to the depolarization event 82 is inhibited. Preferably, the inhibition is implemented by triggering an "inhibition refractory period" ΔT6 starting at the time of detection of the depolarization event 80 and having a duration ΔT6. During the inhibition refractory period ΔT6, local sensing in the left ventricle 10 is disabled so that no detection of threshold crossings is possible, effectively inhibiting the triggering of the delivery of an ETC signal within the duration of the inhibition refractory period ΔT6.

Preferably, the duration of the inhibition refractory period ΔT6 is calculated each time a local depolarization event is detected within the inhibition window ΔTI of the current beat cycle, by using the value of $T_5$ and the known values of ΔT2, ΔT3, ΔT4 and $ΔT5_{MAX}$. For example, the value of $T_5$ may be obtained by the software embedded within the device 1 of FIG. 1 (or embedded within other devices such as the devices 21 24, 64 and 74 of FIGS. 3, 4, 5, and 6, respectively) by starting a timer (not shown) at time zero and recording the value of $T_5$ upon detection of a depolarization event, such as the depolarization event 80, within the duration of the inhibition window ΔTI. The method of determining the time of a detected depolarization is well known in the art and will not be further discussed hereinafter.

Preferably, The inhibition refractory period ΔT6 satisfies the inequality defined in equation 1.

$$ΔT6 > (ΔT2 - T_5) + ΔT3 + ΔT4 + ΔT5_{MAX} \qquad (1)$$

After detecting the depolarization event 80, the duration ΔT6 is determined by calculating its value using equation 2.

$$ΔT6 = (ΔT2 - T_5) + ΔT3 + ΔT4 + ΔT5_{MAX} + ΔTX \qquad (2)$$

wherein ΔTX is a predetermined constant time interval which ensures that the inequality of equation 1 is satisfied, Typically the value of ΔTX may be in the range 1–100 milliseconds. However, other values of ΔTX may be used depending, inter alia, on the specific implementation of the method.

Typically, the duration of the inhibition refractory period ΔT6 is in the range of approximately 150–200 milliseconds, depending, inter alia, on the value of $T_5$ and on the preset value of ΔTX. However, other suitable values of the duration of the inhibition refractory period ΔT6 may also be used. Preferably, the total duration of ΔT6 should not be excessively long since using an excessively long duration of the inhibition refractory period ΔT6 may result in undesirable extending of the period of disabling the sensing in the left ventricle 10 which may prevent the detection of relevant depolarization events such as, for example, depolarization events due to ectopic beats.

It is noted that, the method disclosed hereinabove for determining the value of $T_5$ is given by way of example only, and that other different methods for determining the time of detection of a depolarization event within the duration of the inhibition window ΔTI may be used.

It is noted that, in accordance with another preferred embodiment of the present invention, the value of the inhibition refractory period ΔT6 may a preset value which is used irrespective of the actual value of $T_5$. In this preferred embodiment, the preset value of ΔT6 used is preferably set such that it is equal to or larger than the sum of the inhibition window duration ΔTI, the alert window duration ΔT3, the delay interval ΔT4 and the maximal allowable duration $ΔT5_{MAX}$ of the ETC signal (ΔT6 ≧ ΔTI + ΔT3 + ΔT4 + $ΔT5_{MAX}$).

In FIG. 8, the arrow labeled 86 represents the time of detection of a depolarization event 86 locally sensed in the left ventricle 10. The depolarization event 86 is locally sensed in the left ventricle 10 at a time point which falls within the duration of the alert window ΔT3. Since no depolarization is detected within the inhibition window ΔTI, the depolarization event 86 which is the earliest depolarization event detected within the alert window ΔT3 triggers the delivery of an ETC signal ΔT5. The ETC signal ΔT5 is delivered to the left ventricle 10 after a delay interval ΔT4.

The detection of the earliest depolarization event 86 within the alert window ΔT3 also triggers the initiation of the alert refractory period ΔT7 as disclosed in detail hereinabove and illustrated in FIG. 2, disabling the local sensing of electrical events at the left ventricle 10 for the duration of the alert refractory period ΔT7, and preventing any subsequent depolarization occurring within the duration of the alert refractory period ΔT7 from triggering additional ETC signals within the current beat cycle. For example, the arrow labeled 88 represents the time of occurrence of a depolarization 88 in the left ventricle 10. The depolarization event 88 occurs at a time later than the detection time of the depolarization event 86 and falls within the duration of the alert refractory period ΔT7. Since the sensing in the left ventricle 10 is disabled during the duration of the alert refractory period ΔT7, the depolarization 88 would not be sensed and would therefore not be detected. The disabling of the local sensing of electrical signals in the left ventricle 10 after the initiation of the alert refractory period thus prevents the delivering of an additional ETC signal within the same beat cycle by a potentially threshold-crossing depolarization event due to an ectopic beat, electrical noise and the like and therefore reduces the probability of delivering improperly timed ETC signals which may be arrhythmogenic.

After the alert refractory period ΔT7 terminates, the local sensing of depolarization signals in the left ventricle 10 is re-enabled.

It is noted that, many other suitable methods of event detection using IEGM single or multiple threshold crossing, IEGM signal slope criteria and signal morphology detection methods as disclosed hereinabove or various combinations thereof may be used in the ETC signal timing method of the present invention.

It will be appreciated by those skilled in the art that, while in the schematic diagrams of FIGS. 7 and 8 the zero time point axis on the horizontal axis represents the local detection of a depolarization event at or about the right ventricle 9 and the events such as the events 80, and 86, represent depolarization events locally detected at or about the left ventricle 10 and the depolarizations 82 and 88 represent depolarizations occurring in or about the left ventricle 10, other preferred embodiments are possible in which the time axis zero point represents the local detection of a depolarization event at or about the right atrium 8, the detected events such as the events 80, and 86 represent depolarization events locally detected at or about the left ventricle 10, and the depolarizations 82 and 88 represent depolarizations occurring in or about the left ventricle 10. Such preferred embodiments may have various different electrode and lead configurations (not shown). For example, in one exemplary preferred embodiment, the device 1 may include the lead 2 and electrode(s) 2A for local sensing in or about the right atrium 8, and the lead 6 and electrode(s) 6A for local sensing in or about the left ventricle 10 and for delivering ETC signals to the left ventricle 101 while the lead 4 and the electrode(s) 4A are omitted. In such a case, pacing may be performed, if required, in the right atrium 8 by using the electrode(s) 2A and in the left ventricle 10 by using the electrode(s) 6A, but not in the right ventricle 9.

In another exemplary preferred embodiment of the invention, the device 1 may include the lead 4 and electrode(s) 4A for local sensing in or about the right ventricle 9, and the lead 6 and electrode(s) 6A for local sensing in or about the left ventricle 10 and for delivering ETC signals to the left ventricle 10, while the lead 2 and the electrode(s) 2A are omitted. In such an embodiment, pacing may be performed, if required, in the right ventricle by the electrode(s) 4A and in the left ventricle 10 by the electrode(s) 6A.

It is noted that, in the preferred embodiments in which the device 1 includes a pacing unit, the electrode(s) 6A may be used for delivering a pacing pulse (not shown) to the left ventricle 10 within a cardiac beat cycle and for delivering an ETC signal (not shown) to the left ventricle 10 within the same beat cycle. However, the electrode(s) 6A may also be used for sensing in beat cycles where no pacing or ETC signal is required, or for sensing and pacing in beat cycles where pacing is required but no ETC signal delivery is required.

Similarly, other preferred embodiments of the present inventions are possible in which the leads 2,4 and 6 or the leads 22 include one or more electrodes (not shown) having different functions. For example, the lead 2 of the device 1 of FIG. 1 may include two separate electrodes (not shown) or two separate electrode pairs (not shown) one of these electrodes or electrode pairs is used for local sensing in or about the right atrium 8 and the other of these electrodes or electrode pairs is used for pacing the right atrium 8. This electrode arrangement may be implemented in cases where the same electrode(s) are not capable of being used for sensing and for ETC signal delivery within the same beat cycle due to electrode polarization problems. In another embodiment, the lead 4 of the device 1 of FIG. 1 may include two separate electrodes (not shown) or electrode pairs (not shown) one of these electrodes or electrode pairs is used for local sensing in or about the right ventricle 9 and the other of these electrodes or electrode pairs is used for pacing the right ventricle 9. In yet another preferred embodiment of the present invention, the lead 6 of the device 1 of FIG. 1 may include two separate electrodes (not shown) or electrode pairs one of these electrodes or electrode pairs is used for local sensing in or about the left ventricle 10 and the other of these electrodes is used for delivering ETC signals to the left ventricle 10.

Additionally, other preferred embodiments of the present invention are possible which have different combinations of lead and/or electrode arrangements disclosed hereinabove. For example, in accordance with one preferred embodiment of the present invention, the lead 2 includes a single sensing/pacing electrode 2A, the lead 4 includes a single sensing/pacing electrode 4A and the lead 6 includes one electrode (not shown) for sensing and another electrode (not shown) for delivering ETC signals. Many other permutations and combinations of electrodes and leads are therefor possible in other preferred embodiments of the present invention. For example, various electrode pairs or electrode arrays may be used in place of the single electrodes 2A, 4A and 6A of FIG. 1 or within the implantable leads 22 of FIGS. 3–6 for sensing and/or pacing and/or delivering of ETC signals to appropriate sites within the heart.

It is noted that while the above disclosed method of using an alert window for timing the delivery of ETC signals illustrated in FIGS. 2, 7 and 8, may be adequate for certain patients with certain configurations of implanted electrodes, other different methods of using an alert window for timing the delivery of ETC signals may also be used for improving the safety and efficacy of delivering ETC signals to the heart. For example, in order to avoid spurious detection of pacing artifacts, the use of the refractory period ΔT1 of FIG. 1 does not allow the sensing of any electrical signals within the refractory period ΔT1 or alternatively ignores any of the signals sensed within the refractory period. This method does not take into account the information which may be obtained from the timing of electrical signals occurring during the refractory period ΔT1. However, in some cases, it may be desirable to sense electrical events happening within the refractory period ΔT1, including pacing artifacts and other electrical events such as ectopic events, and/or electrical artifact signals representing LV sensed far field electrical signals associated with myocardial activation in cardiac chambers other than the LV. For example, in patients in which ETC signal delivery utilizes LV sense triggering by RV events as disclosed hereinabove, if the pacing electrode (or electrodes) of the right ventricular lead 4 (FIG. 1) is disposed close to the LV sensing electrode (or electrodes) of the left ventricular lead 6 (FIG. 1), or if the electrical signal conduction in the cardiac tissue interposed between the right ventricular pacing electrode(s) and the left ventricular sensing electrode(s) is fast, a situation may arise in which there is a relatively small temporal separation between the electrical pacing artifact and the LV signal associated with LV activation event which are locally sensed by the left ventricular sensing electrode or electrodes. In such a case the LV sensed depolarization event may be masked by the refractory period ΔT1 and may consequently not be detected. In another non-limiting example, the LV sensing electrode may sense one or more far field electrical signals (also referred to as "far field artifacts" hereinafter) which are associated with electrical activation of the RA or of the RV or of both the RA and the RV. Such electrical pacing artifacts and far field artifacts contain information which may be used to further increase the safety of ETC signal delivery to the heart.

Furthermore, while the use of the alert refractory period ΔT7 of FIG. 8 may be advantageous in preventing the delivery of multiple ETC signals to the heart within a single cardiac beat cycle, as disclosed hereinabove, it ignores any depolarization events which occur within the alert refractory period ΔT7 and treats only the first detected depolarization event which occurs within the duration of the alert window ΔT3 as a valid detected event. However, the method illustrated in FIG. 8 does not take into account the fact that more than one threshold crossing events (i.e. the events 86 and 88 of FIG. 8) did occur within the duration of the alert window ΔT3. This may lead to improper timing of the ETC signal because it is possible that the earlier signal 86 is due to an electrical noise or an ectopic beat and the later signal 88 is the "true" signal representing the locally sensed LV activation. Additionally, if one of the events 86 and 88 of FIG. 8 is an ectopic beat, an ETC signal may still be delivered to the heart at a vulnerable time which may be arrhythmogenic.

In such cases as well as in other cases R may be advantageous to sense all the electrical events occurring after the time $T_0$ (FIG. 2) and to use a suitable classification method or classification criteria to distinguish between a pacing electrical artifact or far field artifacts and a true locally sensed depolarization event. This classification method may include the occurrence of the detected events relative to one or more defined time windows, as is disclosed in detail hereinafter.

Figure 9A:
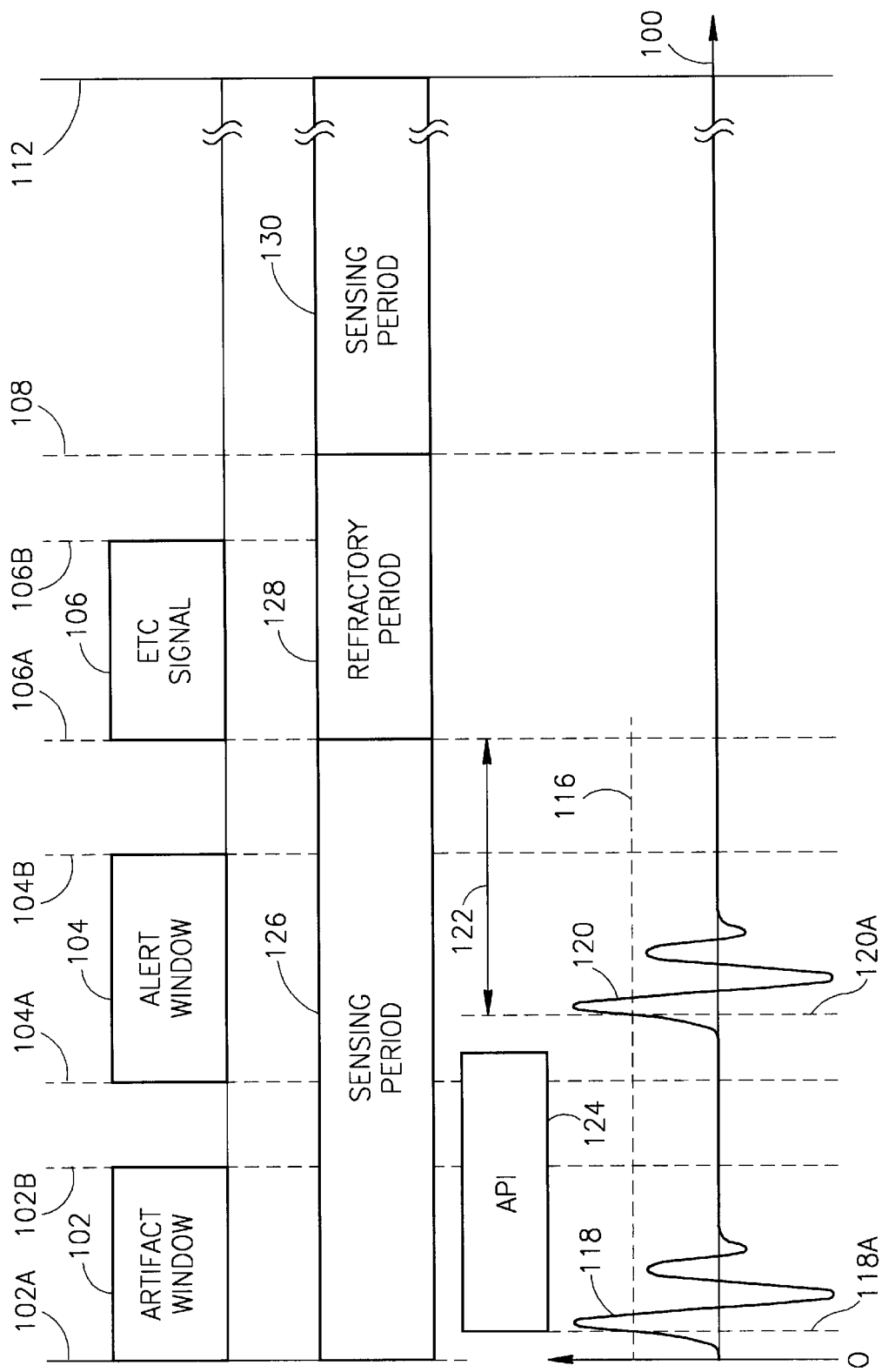
FIGS. 9A and 9B are schematic diagrams useful in understanding two different variations of a method of using an alert window for timing the delivery of ETC signals useful in operating the device of FIG. 1, in accordance with other preferred embodiments of the present invention.
Figure 9B:
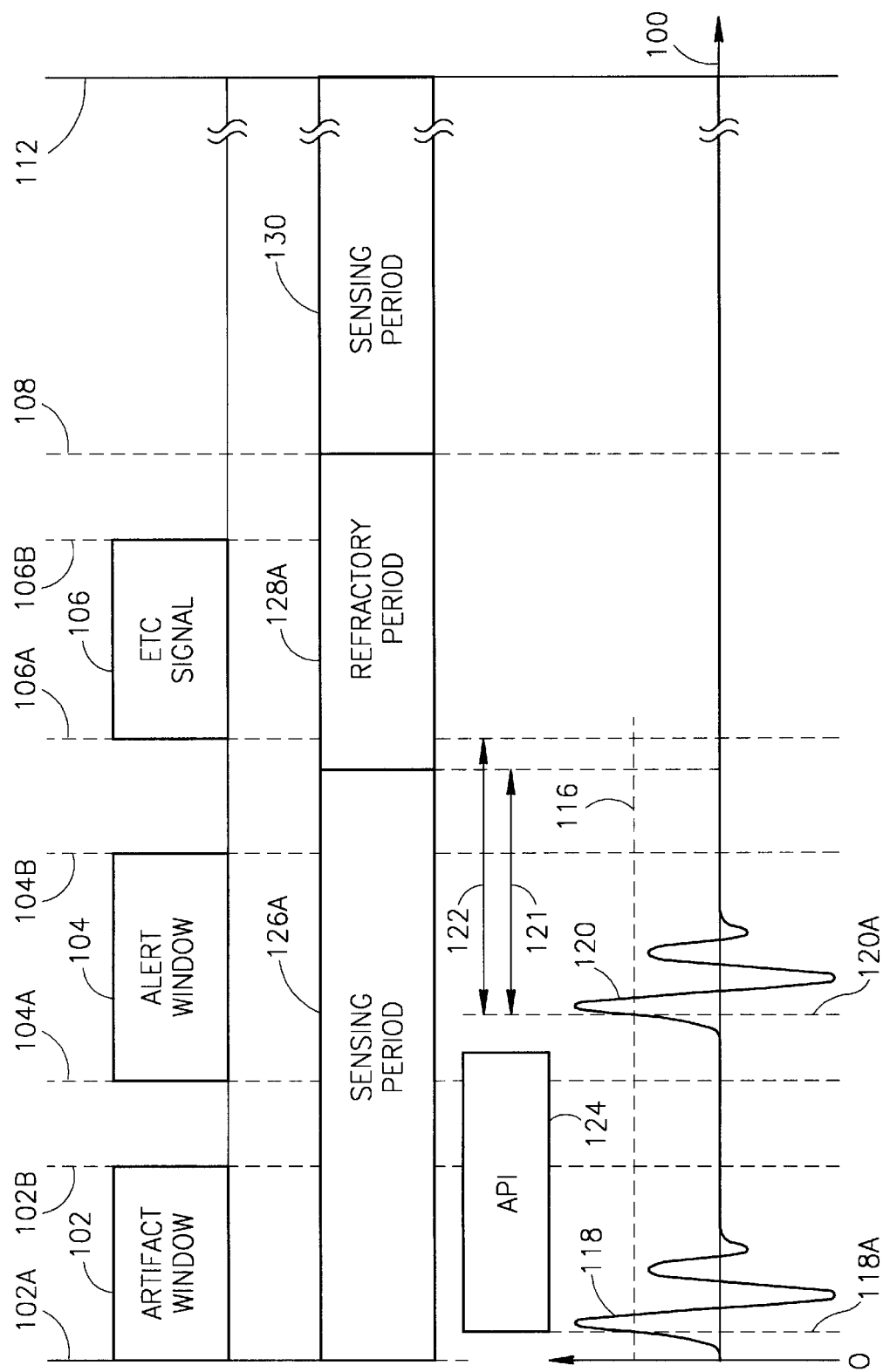

Reference is now made to FIGS. 9A and 9B which are schematic diagrams useful in understanding two different variations of a method of using an alert window for timing the delivery of ETC signals useful in operating the device of FIG. 1, in accordance with other preferred embodiments of the present invention.

It is noted that the schematic diagrams of FIGS. 9A and 9B refer by way of example to a device configuration in which sensing and pacing is performed in the RV and the RV detected event or RV pace or RV pacing command is used as the trigger event. However, other preferred embodiments of the method may also be used in which sensing may be performed in the RA, with or without RA pacing and in which the RA detected event or the RA pacing or an RA pacing command are used as the trigger event as is disclosed in detail hereinafter.

The horizontal axis 100 represents time (in arbitrary units) and the vertical axis schematically represents the amplitude of the electrical signal sensed by a sensing electrode disposed at or about the LV. The vertical line 1 02A coincides with the zero time point on the axis 100 which represents the time of occurrence of a trigger event (the trigger event itself is not shown herein for the sake of clarity of illustration). The trigger event may be any suitable signal which is indicative of or associate with RV activation, either by pacing or due to the intrinsic cardiac rhythm. The trigger event may be implemented in many different ways. For example, the trigger event may be a logical pulse or any other suitable type of electrical signal indicative of a detected right ventricular activation event (RV sense) or a right ventricular pacing event (RV pace). Such a logical pulse may be provided by any suitable detecting circuitry or sensing/detecting unit such as, but not limited to the sensing units 38 of FIGS. 3–4. The trigger event may also be a logical signal or any other suitable type of signal provided by a microprocessor or a controller unit which controls the ETC device, such as but not limited to the controller unit 40 of FIGS. 3–4 and the processing unit 61 of FIGS. 5–6. For example, in the case of the preferred embodiment illustrated in FIGS. 5–6 in which the detection process is performed by the processing unit 61, the processing unit 61 may internally generate a detection signal which is used as the trigger event 102A. Additionally, when RV pacing is performed, the command signal which is generated by the processing unit 61 to activate the pacing unit 68 may be used as the trigger event. However, any other types of suitable signals known in the art which are indicative of RV activation, or otherwise suitably temporally linked to the RV activation may be used as the trigger event.

The vertical dashed line 102A also represents the starting time of an artifact window 102 and the vertical dashed line 102B represents the ending time of the artifact window 102 (schematically represented by the horizontal bar delimited by the lines 102A and 102B). The vertical dashed line 104A represents the starting time of an alert window time period 104 and the vertical dashed line 104B represents the ending time of the alert window 104 (the alert window period 104 is represented by the horizontal bar delimited by the lines 104A and 104B). The vertical dashed line 106A represents the starting time of the ETC signal delivery period 106 and the vertical dashed line 106B represents the ending time of the ETC signal delivery period 106. The duration of the ETC signal delivery period 106 is represented by the horizontal bar delimited by the lines 106A and 106B. An LV sensed event 120 crosses a threshold level 116 at a time represented by the crossing of the time axis 100 with the vertical dashed line 120A. The time of detection of the crossing of the threshold level 116 by the LV sensed event 120 is represented by the intersection point of the vertical dashed line 120A with the time axis 100.

When the time of threshold crossing of the event 120 occurs within the duration of the alert window 104, the delivery of an ETC signal to the LV is enabled and the ETC signal is delivered to the heart after an ETC delay time 122. The ETC delay time 122 is schematically represented by the horizontal double headed arrow labeled 122. It is noted that the ETC delay time 122 may also be referred to as the "first delay period" hereinafter.

The actual shape and parameters of the ETC signal are not the subject matter of the present application and are therefore not shown in detail herein. However, generally, any of the ETC signal shapes or waveforms suitable for cardiac contractility modulation which are known in the art and disclosed in any of the International Patent Applications to Ben Haim et al. referenced hereinabove may be used. The vertical line 112 represents the time of occurrence of the next trigger event which follows the trigger event who's time of occurrence is represented by the vertical line 102A. The time interval delimited on the time axis 100 between the vertical lines 102A and 112 represents a single cardiac beat cycle.

The particular exemplary beat cycle illustrated in FIG. 9A comprises a sensing period 126, a refractory period 128 and a sensing period 130. The sensing period 126 starts at the trigger event represented by the line 102A and ends at the time of starting of delivery of the ETC signal represented by the line 106A. During the sensing period 126, local sensing is performed using the LV sensing electrode or electrodes. The refractory period 128 starts at the time of starting of delivery of the ETC signal represented by the line 106A and ends at the time represented by the vertical dashed line 108.

The duration of the refractory period 128 is preferably greater than the ETC signal delivery period 106. The purpose of the refractory period 128 is to ensure that no electrical artifacts associated with the delivery of the ETC signal to the heart are erroneously detected as valid events. This may be accomplished in different ways. In accordance with one preferred embodiment of the present invention, during the refractory period 128 electrical event sensing is performed but detection is not performed, effectively ignoring any electrical signals sensed in the LV within the duration of the refractory period 128. Alternatively, in accordance with another preferred embodiment of the present invention, sensing or sensing and detecting may be stopped for the duration of the refractory period 128. The first alternative may be useful in implementations in which amplifier saturation is not a concern, such as when no amplification is performed prior to digitizing of the sensed signal. The second alternative may be preferred when the method is implemented using saturation sensitive amplification circuitry (not shown). However, it will be appreciated that other alternative methods known in the art for implementing the refractory period 128 may be used as long as care is taken to ensure that the ETC signal associated electrical artifacts do not degrade or adversely affect the performance of the sensing and/or the detecting circuitry (not shown).

The sensing period 130 starts after the ending of the refractory period 128 represented by the vertical line 108 and ends at the trigger signal (schematically represented by the line 112) of the next beat cycle. During the sensing period 130, LV local sensing is performed. Detected events which occur within the duration of the sensing period 130 are used for inhibiting the delivery of an ETC signal in the next beat cycle (not shown) following the current beat cycle, as is disclosed in detail hereinafter.

Typically, in the method of ETC signal delivery illustrated in FIGS. 9A and 9B, ETC signal delivery is initially disabled at the beginning of the current beat cycle. If a valid event is detected within the duration of the alert window 104, ETC signal delivery is conditionally enabled as is disclosed in detail hereinafter. The term "conditionally enabled" is used herein to denote that other electrical events detected after the enabling of ETC signal delivery but before the actual delivery of the ETC signal may disable or inhibit the delivery of the ETC signal, as is disclosed in detail hereinafter.

When an RV sense or RV pace event is used as the trigger event, The artifact window 102 defines a time period during which electrical artifacts are expected to be sensed by the left ventricular local sensing electrode. Such electrical artifacts may include electrical pacing artifacts due to RV pacing (if sensed by the LV sensing electrode), but may also include electrical far-field artifacts due to sensing of the activation of the RV. The sensing of these artifact types may depend, inter alia, on the position of the various sensing and pacing electrodes in or about the different cardiac chambers, on the quality of the leads containing the sensing and/or pacing electrodes, on the patient's cardiac condition and on other conditions. While such pacing artifacts and far field sensing artifacts may be expected to appear more or less regularly within the artifact window 102, other electrical signals associated with ectopic cardiac activation or other external electrical noise types may or may not be sensed within the duration of the artifact window 102. Thus, for example, when the detection criterion which is used is a crossing of the threshold level 116, the electrical artifact signal 118 schematically represents the LV sensed electrical artifact due to RV pacing or due to far field sensing of electrical activation of the RV due to the natural cardiac rhythm. The electrical artifact signal 118 crosses the detection threshold level 116 at the time represented by the point of intersection of the time axis 100 with the vertical dashed line 118A.

Any event detected within the duration of the artifact window 102, such as the detected artifact signal 118 is interpreted by the method of the present invention, as an event due to an expected LV artifact signal due to RV pacing or to a far field sensed artifact signal. Thus, the method does not treat any event which is detected within the duration of the first artifact window 102 as a valid detected event representing true LV activation. Any event (not shown) which is detected in the time interval between the end of the first artifact window 102 and the beginning of the alert window 104 (this time interval is schematically illustrated as the time interval between the vertical dashed lines 102B and 104A of FIG. 9A), is a suspected event since it may be an event due to an ectopic beat. Therefore, if an event (not shown in FIG. 9A) is detected in the time interval between the end of the first artifact window 102 and the beginning of the alert window 104, the method inhibits the delivery of an ETC signal to the heart even if a valid event such as the detection of the threshold crossing by the LV sensed event 120 is later detected within the duration of the alert window period 104.

It is noted that, more than one threshold crossing event may occur within the duration of the first alert window 102. For example, the LV sensed electrical pacing artifact signal or the far field sensed artifact signal may be a multi-phasic signal having more than one threshold crossing peak (not shown) due to amplifier ringing, filtration artifacts or other reasons. Thus, any events which are detected within the duration of the first artifact window 102 are interpreted as being due to an expected electrical artifact and will not cause inhibition of ETC signal delivery.

If an event (not shown) is detected in the time interval between the end of the first artifact window 102 and the beginning of the alert window 104 this detected event may represent an ectopic beat in which case it is desired to inhibit ETC signal delivery within the current beat cycle to avoid possible arrhythmogenic effects. However, such a detected event occurring in the time interval between the end of the first artifact window 102 and the beginning of the alert window 104 may also represent a pacing artifact related detected event due to the detection of an additional threshold crossing peak (not shown) of an expected multi-peaked electrical artifact signal, or due to other external electrical noise types which are not related to cardiac electrical activity, in which case it is desired to ignore the detected event and to enable ETC signal delivery if an ETC signal is required.

However, since the use of a simple single threshold level criterion may not always allow to differentiate between an ectopic beat, a pacing artifact related detected event and other electrical noise types, such further classification of detected events following the first (expected) detected event is not attempted. The method thus inhibits the delivery of an ETC signal to the heart within the current beat cycle if a threshold crossing event is detected in the time interval between the end of the first artifact window 102 and the beginning of the alert window 104. The term "inhibits" is used herein to indicate that an ETC signal will not be delivered to the heart even if a valid detection occurs later within the duration of the alert window 104 of the current beat cycle. This inhibition is advantageous since it decreases the probability of delivery of a wrongly timed and therefore potentially arrhythmogenic ETC signal and therefore increases the safety of the ETC therapy.

In some patients the detected electrical artifact signal 118 and the LV sensed event 120 representing the LV activation may be temporally close to each other. This may occur, inter alia, due to the electrical recording conditions such as, but not limited to, electrode positioning, lead structure, and due to other cardiac related factors. In such patients, the starting time 104A of the alert window 104 may be positioned close to the ending time 102B of the artifact window 102. However, since the exact time of the threshold crossing 118A of the electrical artifact signal 118 within the artifact window 102 may vary due to, inter alia, jitter, heart rate changes, cardiac tissue conductivity changes and the like, it may happen that the LV sensed event 120 representing the LV activation may be detected temporally close to the electrical artifact signal 118. Such a detection of a threshold crossing LV sensed event 120 which is temporally close to the detection of the electrical artifact signal 118 may be suspected as being caused by an additional threshold crossing peak (not shown) of the pacing electrical artifact 118 itself due to ringing or other pacing artifact variability. It is therefore desirable to put a lower limit on the minimal allowable temporal separation of the detection times 118A and 120A. The methods illustrated in FIGS. 9A and 9B may therefore include an additional safety mechanism for dealing with the detection of additional threshold crossing events which may be sensed after the time of the first threshold crossing of the artifact signal 118 represented by the line 118A. This safety mechanism involves the use of an artifact proximity interval (API). The artifact proximity interval starts from the time of occurrence of a specified event detected within the duration of the first artifact window 102. This specified event which is used for determining the starting time of the artifact proximity interval is generally referred to as the "proximity interval initiating event" hereinafter.

For example, the artifact proximity interval 124 of FIGS. 9A and 9B is a time interval starting at the time of detection of the first threshold crossing event occurring within the artifact window 102. In the particular cases illustrated in FIGS. 9A and 9B, there is only one threshold crossing event in which the signal 118 crosses the threshold 116 at the time represented by the vertical dashed line 118A. Thus, the vertical dashed line 118A also represents the proximity interval initiating event associated with the API 124. However, more than one threshold crossing event may be detected within the duration of the artifact window 102. For example, the artifact signal which is sensed within the duration of the first artifact window 102 may include multiple threshold crossing peaks (not shown).

It will be appreciated by those skilled in the art, that when the artifact signal which is sensed within the first artifact window 102 has a plurality of threshold crossing peaks (not shown), the proximity interval initiating event used to provide the starting time of the API may be set as the time of detection of any of the threshold crossing peaks (not shown) of the artifact signal sensed within the duration of the first artifact window 102, assuming that the general shape and characteristics of the artifact signal detected within the duration of the first artifact window 102 do not exhibit unacceptably large changes for different cardiac beats (For example, when using the threshold crossing detection method disclosed hereinabove, one assumes that the number of threshold crossing peaks within the artifact signal does not change from beat to beat).

In a non-limiting example, if the artifact signal observed by the cardiologist has three threshold crossing peaks (not shown), the first threshold crossing peak (not shown) may be selected by the cardiologist as the proximity interval initiating event used to determine the starting time of the API, or alternatively, the second threshold crossing peak (not shown) may be selected as the proximity interval initiating event used to determine the starting time of the API, or alternatively, the third threshold crossing peak (not shown) may be selected by the cardiologist as the proximity interval initiating event used to determine the starting time of the API. It is noted that the values which are set by the cardiologist for the API duration in each of these three different cases may be different from each other.

The API 124 has a preset duration which is manually set by the cardiologist in a test session as disclosed in detail hereinafter. The duration of the API 124 is schematically represented by the horizontal bar labeled 124 of FIGS. 9A and 9B. Threshold crossing signals which occur within the duration of the first artifact window 102 are considered by the method to be due to an expected artifact signal (such as, for example, a pacing related electrical artifact signal or a far field sensed electrical artifact associated with intrinsic activation of a cardiac chamber). However, Any threshold crossing signal which is detected within the part of the API 124 which does not overlap the first artifact window 102, is considered to be a "suspected" signal since the method cannot distinguish between a threshold crossing which is due to an additional peak of a multi-phasic artifact signal (such as a pacing artifact with multiple peaks due to ringing), a potentially arrhythmogenic ectopic beat, and a threshold crossing due to a valid signal caused by local activation of the LV. Therefore, if a threshold crossing signal is detected within the part of the API 124 which does not overlap the first artifact window 102, the delivery of an ETC signal to the heart within the current beat cycle is inhibited. However, any threshold crossing event which is detected within the duration of the first artifact window 102 is always assumed to be an artifact associated event and will therefore not inhibit the delivery of an ETC signal to the heart even though it may also occur within the duration of the API 124. This inhibition of ETC signal delivery is implemented such that following this inhibition, even if a threshold crossing signal is later detected within the alert window 104 of the current beat cycle, ETC signal delivery will not occur within the current beat cycle. The disclosed use of the API 124 to inhibit the delivery of an ETC signal to the heart upon detection of a threshold crossing event within the part of the API which does not overlap the first artifact window 102 is advantageous since by preventing ETC delivery in cases of detection of suspected signals one reduces the probability of delivering of wrongly timed and therefore potentially arrhythmogenic ETC signals due to a spurious detection of a pacing related electrical artifact peak within the duration of the alert window, thereby increasing the safety of ETC signal delivery.

It is noted that while the refractory period 128 of FIG. 9A starts at the time of beginning of the ETC signal 106, this is not mandatory. For example, in accordance with another preferred embodiment of the present invention such as the embodiment illustrated in FIG. 9B, the refractory period 128A is timed to start before the beginning time of the ETC signal 106. This is implemented by starting the refractory period 128A after a second delay period 121 (which is schematically represented by the double headed arrow labeled 121) starting at the time of detection 120A of the LV sensed event 120. The second delay period 121 is shorter in duration than the ETC delay period 122, such that the resulting refractory period 128A of FIG. 9B starts earlier than the beginning time of the ETC signal 106. The refractory period 128A ends at the time represented by the vertical dashed line labeled 108. It is noted that the sensing period 126A of FIG. 9B is shorter than the sensing period 126 of FIG. 9A.

Preferably, the beginning of the refractory period 128A should not precede the beginning of the ETC signal 106 by a large time interval since this will reduce the duration of the sensing period 126A which is available for detecting possible ectopic beats relative to the duration of the sensing period 126 of FIG. 9A with the result of an increased chance of overlooking a possible ectopic beat which may occur prior to the delivery of the ETC signal 106. Thus, preferably, the time interval defined between the end of the second delay period 121 of FIG. 9B and the end of the ETC delay interval 122 should be minimized.

Figure 10A:
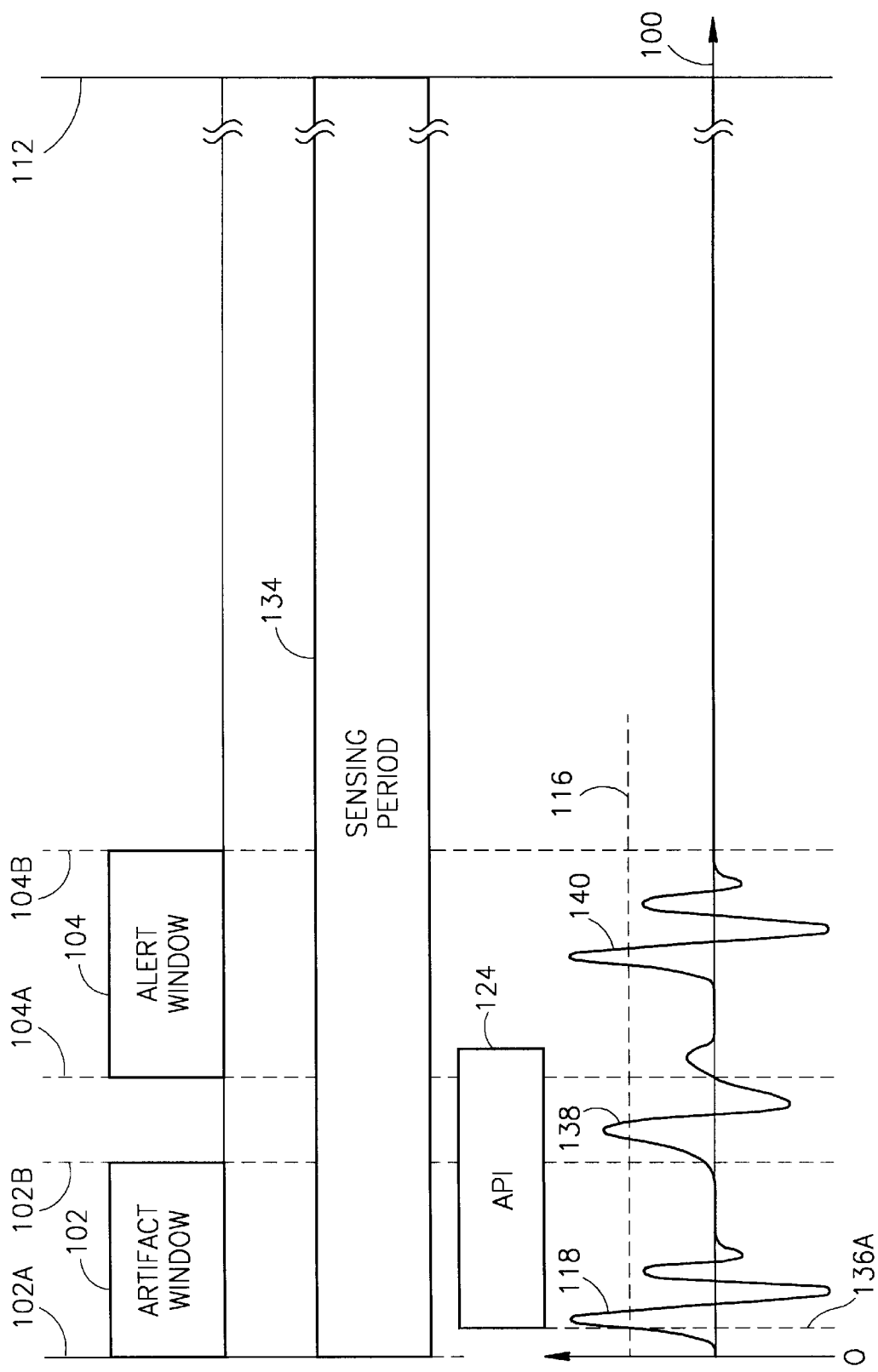
FIGS. 10A–10C are a schematic diagrams useful in understanding the use of an artifact proximity interval method, in accordance with a preferred embodiment of the present invention.
Figure 10B:
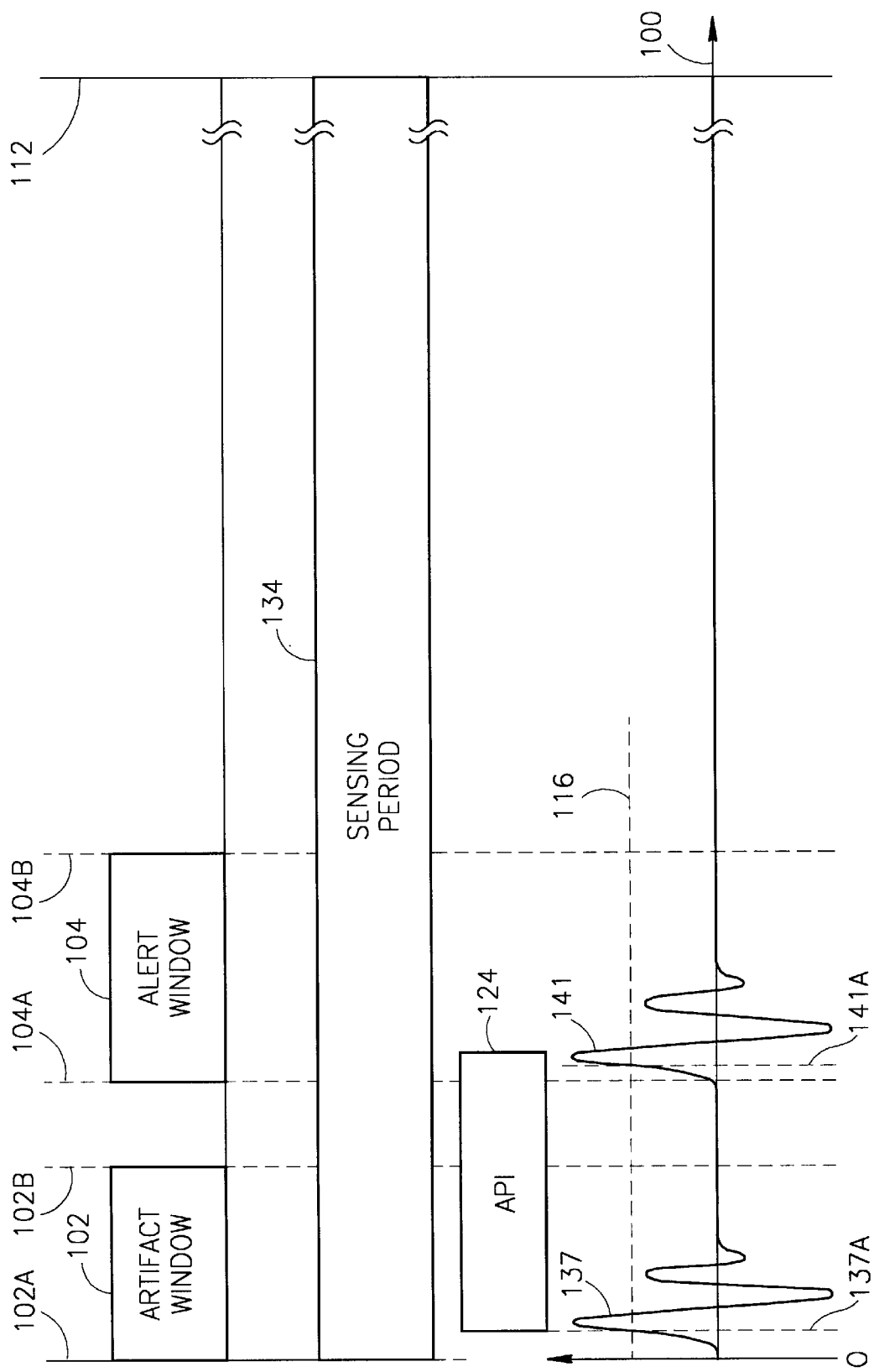
Figure 10C:
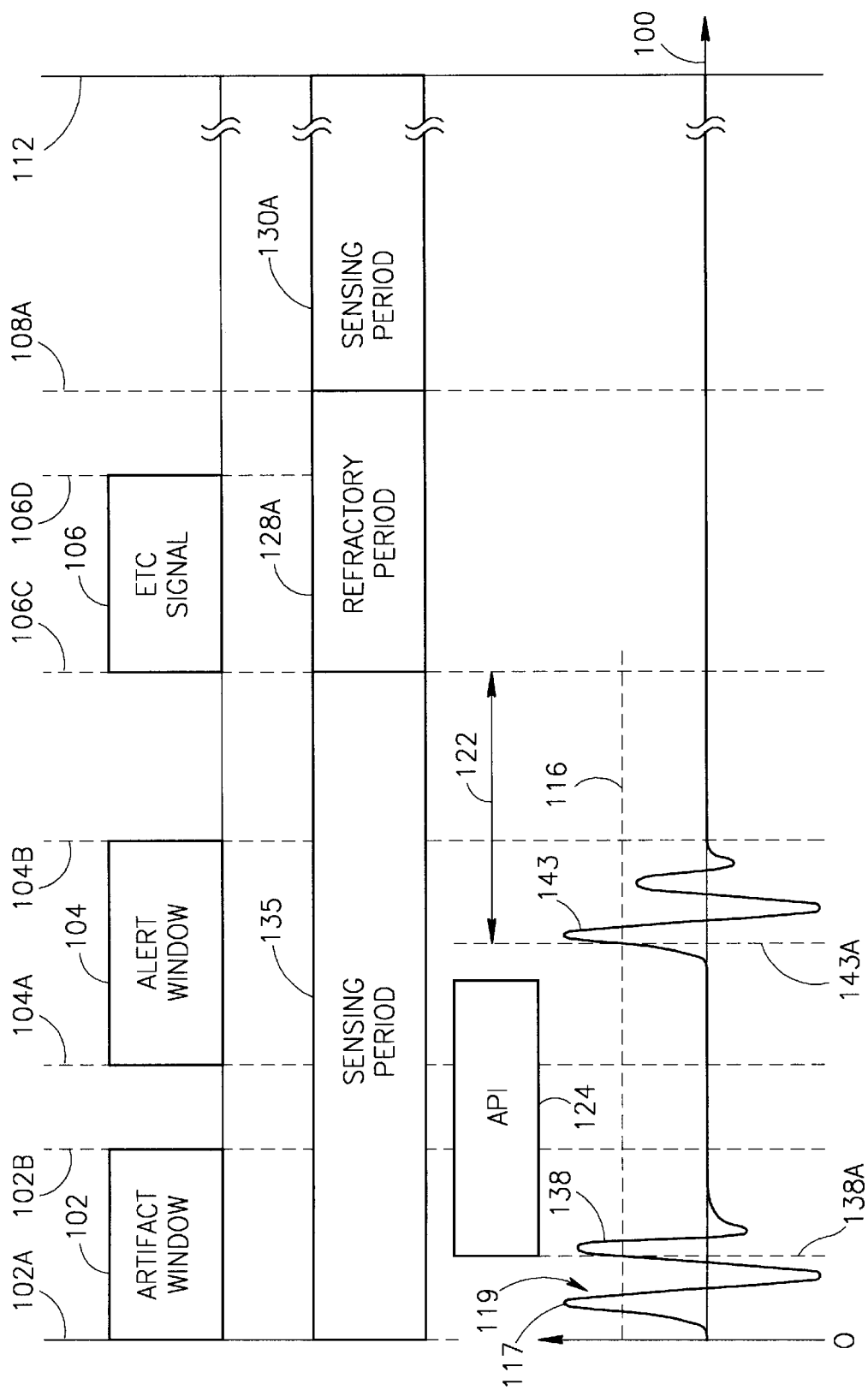

Reference is now made to FIGS. 10A–10C, which are schematic diagrams useful in understanding the use of an artifact proximity interval method, in accordance with a preferred embodiment of the present invention. In FIGS. 10A–10C and 10B, the artifact window 102 and the alert window 104 are identical to the artifact window 102 and the alert window 104 of FIGS. 9A–9B.

In FIG. 10A, a pacing artifact signal 118 crosses the threshold 116 within the duration of the artifact window 102, at the time schematically represented by the intersecting point of the time axis 100 with the vertical dashed line 136A. The API 124 starts at the time of crossing of the threshold 116 by the artifact signal 118. Thus, the event of crossing of the threshold 116 by the artifact signal 118 represented by the vertical dashed line 136A also represents the proximity interval initiating event for FIG. 10A. A second crossing of the threshold 116 by a signal 138 occurs within the duration at the API 124. The second threshold crossing by the signal 138 occurs outside of the duration of the first artifact window 102. The second threshold crossing signal 138 may be a pacing artifact related signal, a far field sensed artifact signal, an ectopic beat related signal, an external electrical noise associated signal or a signal representing true LV activation. The threshold crossing by the second threshold crossing signal 138 occurs within the duration of the time interval between the end of the first artifact window 102 and the beginning of the alert window 104. Therefore, the ETC device such as, for example the ETC device 1, of FIG. 1 (or the devices illustrated in FIGS. 3–6) inhibits the delivery of an ETC signal to the LV within the duration of the current beat cycle (which is represented by the time interval between the vertical lines 102A and 112). This inhibition of the delivery of an ETC signal would have occurred even in a case in which no API is used (such as, for example, in a case in which the duration of the API 124 is set to zero by the cardiologist), since the detection of an event within the duration of the time interval between the end of the first artifact window 102 and the beginning of the alert window 104 is an inhibitory event which inhibits the delivery of an ETC signal within the current beat cycle as disclosed in detail hereinabove. Incidentally, the threshold crossing by the second threshold crossing signal 138 occurs within the part of the API 124 which does not overlap with the first artifact window 102.

Therefore, in FIG. 10A, although a threshold crossing signal 140 is later detected within the duration of the alert window 104 of the current beat cycle, ETC signal delivery is inhibited for the current beat cycle and no ETC signal is delivered to the LV. Thus, an uninterrupted sensing period 134 (represented by the horizontal bar labeled 134) lasts for the entire duration of the current beat cycle since no refractory period is implemented because no ETC signal is delivered.

Another example of the use of the API 124 is illustrated in FIG. 10B. In FIG. 10B, the duration and timing of the artifact window 102, the alert window 104, the API 124 and the sensing period 134 are as disclosed in FIG. 10A. A pacing artifact signal 137 crosses the threshold 116 at the time represented by the intersecting point of the time axis 100 with the vertical dashed line 137A. The API 124 starts at the time of the first threshold crossing of the artifact signal 137. The proximity interval initiating event of FIG. 10B is selected as the first threshold crossing occurring within the duration of the artifact window 102 and is thus represented by the vertical dashed line labeled 137A. A second threshold crossing signal 141 occurs within the duration at the API 124 at a time schematically represented by the vertical dashed line labeled 141A. The second threshold crossing signal 141 may be a pacing artifact related signal, a far field sensed artifact signal, an ectopic beat related signal, an external electrical noise associated signal or a signal representing true LV activation. However, since the threshold crossing by the second threshold crossing signal 141 occurs at the time represented by the vertical dashed line 141A which is within the duration of the API 124, the ETC device such as, for example the ETC device 1 of FIG. 1, inhibits the delivery of an ETC signal to the LV within the duration of the current beat cycle (which is represented by the time interval between the vertical lines 102A and 112. This inhibition occurs, even though the second threshold crossing by the signal 141 occurred within the duration of the alert window 104 since in the particular case illustrated in FIG. 10B, the API 124 temporally overlaps the alert window 104 and since the detection of a threshold crossing within the duration of the API always inhibits the delivery of an ETC signal within the current beat cycle due to an event which is detected within the alert window 104 (in the particular case illustrated in FIG. 10B the threshold crossing event 141 is the same event that is detected within the duration of the API 124 and within the duration of the alert window 104).

In the example illustrated in FIG. 10C, the proximity interval initiating event is selected as the last (latest) threshold crossing event which is detected within the duration of the first artifact window 102. A first peak 117 of a pacing artifact signal 119 crosses the threshold 116 within the duration of the artifact window 102, a second peak 138 of the pacing artifact 119 crosses the threshold 116 at the time represented by the intersecting point of the time axis 100 with the vertical dashed line 138A. The second peak 138 crosses the threshold 116 within the duration of the artifact window 102. Since the API 124 is initiated by the last threshold crossing occurring within the duration of the first artifact window 102, the API 124 of FIG. 10C starts at the proximity interval initiating event which is schematically represented by the time of the second crossing of the threshold 116 by the peak 138 of the artifact signal 119. A third crossing of the threshold 116 by a signal 143 occurs at a time schematically represented by the vertical dashed line labeled 143A. The third crossing of the threshold 116 by the signal 143 occurs within the duration of the alert window 104 and outside the duration of the API 124. Therefore, an ETC signal with a duration represented by the horizontal bar labeled 106 is delivered to the heart. A refractory period 128A is also implemented as disclosed hereinabove. it is noted that since the time of detection of the signal 143 of FIG. 10C occurs at a different (later) time than the time of detection of the signal 120 of FIG. 9A, and since the duration of the ETC delay period 122 is identical in FIGS. 9A and 10C, the beginning time 106C and the ending time 106D of the ETC signal 106 of FIG. 10C are shifted relative to the beginning time 106A and the ending time 106B of the ETC signal 106 Of FIG. 9A, respectively. Similarly, the refractory period 128A of FIG. 10C is shifted (with respect to the trigger event 102A) in comparison to the refractory period 128 of FIG. 9A. Additionally, the sensing period 135 of FIG. 10C is longer in duration than the sensing period 126 of FIG. 9A, and the sensing period 130A of FIG. 10C may be shorter than the sensing period 130 of FIG. 9A. However, it will be appreciated that the precise duration of the sensing periods 130 (FIG. 9A) and 130A (FIG. 10C), is determined by the duration of the specific beat cycle which may vary from beat to beat. Therefore, a comparison of the duration of the sensing periods 130 and 130A is not meaningful using the schematic illustrations of FIGS. 9A and 10C (as schematically illustrated by the break mark on the axis 100 of FIGS. 9A and 10C).

It is noted that, the inhibition of ETC signal delivery induced by the sensing of a threshold crossing signal such as but not limited to the threshold crossing signal 138 detected within the part of the API 124 which does not overlap the first artifact window 102 may be implemented in implantable ETC devices such as, but not limited to, the pacemaker/ETC device 21 of FIG. 3, and in non-implanted ETC devices such as but not limited to the system 60 of FIG.5.

Additionally, such inhibition of ETC signal delivery induced by the detection of a threshold crossing within the API 124 may be implemented in implantable ETC devices lacking pacing capabilities, such as but not limited to the ETC device 24 illustrated in of FIG. 4, and in non-implanted ETC devices lacking pacing capabilities such as but not limited to the system 70 of FIG. 6. In these systems, a first and a second threshold crossing signals (signals not shown) which are not associated with electrical pacing artifacts may be detected within the duration of the API 124. For example, such first and second threshold crossing signals may be parts of a multi-peaked or multi-phasic far field sensed RV activation signal. Such multi-peaked or multi-phasic signals may arise due to amplifier ringing, filtration artifacts, or other reasons.

The duration of the API 124 is determined by a cardiologist or physician and may be based on data recorded in a test recording period or test session occurring after the implantation of the electrodes in the patient, as disclosed in detail hereinabove. In the test session, the cardiologist or physician examines the variability in the signal parameters (such as but not limited to signal duration and signal amplitude) of the pacing associated electrical artifact signals such as the signal 118 (FIGS. 9A–9B), the artifact signal 119 (FIG. 10C) and the like, and of the LV sensed signals associated with local LV activation, such as the LV sensed event 120 (FIG. 9). The test session may be performed using a system such as the system 60 and the ETC device 64 of FIG. 5 or other similar suitable systems for recording displaying and analysis of cardiac IEGM as disclosed hereinabove. The cardiologist may record and examine the sensed IEGM signal in the LV sensing electrode (such as, but not limited to the electrode 6A of FIG. 1) in a plurality of RV paced cardiac beats. The recorded IEGM signals sensed by the LV sensing electrode 6A may be then averaged and displayed or displayed individually on a display unit, such as but not limited to the display unit 32 of the system 60 of FIG. 5.

The detection threshold level may be displayed as a visually distinct line or cursor or the like on the display unit 32 and manually adjusted by the cardiologist, using one or more of the user interface devices 69, to yield satisfactory detection of LV sensed events without unduly increasing false detection of noise signals (false positives). The duration of the artifact window 102 may then be adjusted based on the parameters of the pacing artifact signal such as the signal's amplitude, shape duration or other suitable artifact signal parameters, and on the selected detection threshold level 116. Typically the duration of the artifact window 102 is selected such as to ensure satisfactory detection of the first threshold crossing of the pacing artifact signal, taking into account the observed degree of artifact signal temporal jitter. The cardiologist also determines and sets the duration and starting point of the alert window 104, based on the timing and temporal variability of the recorded and displayed signals representing the locally sensed activation of the LV, such as, for example, the signal 120 of FIG. 9, with the aim of optimizing the detection of LV activation signals without unduly increasing the probability of false positives due to electrical noise or other signals, as disclosed in detail hereinabove.

The cardiologist also determines and sets the desired proximity interval initiating event and the desired duration of the artifact proximity interval (API) 124, based, inter aeia, on the observed shape and on the number of threshold crossing events detected within the duration of the first artifact window 102 (if more than one threshold crossing event occurs within the duration of the first artifact window 102, due to amplifier ringing or a multi-peaked artifact signal shape or other reasons). The duration of the API 124 set by the cardiologist represents the minimum allowable separation between the proximity interval initiating event and the valid detected event representing the detection of electrical activation of the LV. The setting of the API duration by the cardiologist takes into account the actual separation which is observed by the cardiologist in the recorded cardiac beats obtained in the test session.

It is noted that, in some cases, the API 124 and the alert window 104 may partially overlap as illustrated in FIGS. 9 and 10A and 10B. This may occur when the LV sensed signal 120 representing the locally sensed LV activation occurs temporally close to the pacing artifact signal 118, due to a fast conduction path or to any other reason. However, typically, the API 124 does not necessarily overlap the alert window 104. It is noted that for paced beats the duration of the API 124 is a preset value and does not change from one paced beat to another paced beat. Therefore the extent of overlap of the API 124 with the alert window 104, if such overlap occurs at all, is variable and depends on the time of occurrence of the proximity interval initiating event within the first artifact window 102 (such as but not limited to the time of crossing of the threshold 116 by the artifact signal 118 of FIGS. 9A–9B, or the time of crossing of the threshold 116 by the signal peak 138 of the artifact signal 119 of FIG. 10C)

It is noted that, while typically the artifact window 102 and the alert window 104 do not overlap, it is possible that in certain patients and electrode placements, the alert window 104 may begin immediately after the end of the artifact window 102.

It is further noted that the duration of the artifact window 102 may be adjusted ito a suitable size depending on the observed parameters of the pacing artifact signal 118 (FIGS. 9A–9B). For example, if due to favorable lead quality, lead placement and/or other physiological conditions, a pacing artifact is not observed or has a peak amplitude which is very small compared to the signal detection threshold 116 which was set, the duration of the artifact window 104 may be set to zero. This means that practically no artifact window will be used. In such cases the duration of the API will also be set to zero since no information is available on the timing of the pacing artifact.

It is further noted that the duration of the API 124 may be determined, inter alia, by the electrical characteristics of the sense circuitry (not shown) used for LV sensing. For example, if the sensing uses analog sensing circuits, the lowest duration for the API 124 may be dictated by the response characteristics of the sensing circuits such as the clipping caused by circuit saturation and the like as is known in the art. These given characteristics may therefore dictate a minimum duration selectable for the API 124. Nevertheless, the cardiologist may still select a duration for the API 124 which exceeds this minimal duration based on the observed pacing artifact parameters.

It is still further noted that, in cases in which the artifact signal is not temporally close to the locally sensed detected event due to LV activation, and the API 124 is therefore redundant, the cardiologist may set the value of the duration of the API 124 to zero, effectively canceling the API 124. The API 124 may also be set to zero or cancelled in cases in which the artifact signal is not detected by the detection method which is being used. For example, if the event detection method is based on a single threshold crossing criterion, the API 124 may be set to zero or cancelled if the artifact signal does not cross the detection threshold level. Similarly, if any other detection method is being used and the artifact signal is not detected by this detection method, the API 124 may be zeroed or cancelled.

The duration of the refractory period 128 (FIG. 9) is also set by the cardiologist based on the empirically observed parameters of the ETC signal induced electrical artifact (not shown). The duration of the refractory period 128 is set such that it is long enough to allow the decay of the ETC signal induced artifact to such a level that it will not be erroneously detected as a threshold crossing event. Therefore, the duration of the refractory period 128 may be also affected by the value of the threshold 116 which was selected by the cardiologist. Similar considerations apply for setting of the duration of the refractory period 128A of FIG. 9B. If all the ETC signals which are delivered to the LV have identical signal parameters, the duration of the refractory period 128 is adjusted according to the parameters of the observed ETC induced artifact signal. However, the device which is being used for delivering ETC signal therapy may also be capable of delivering variable ETC signals to the heart. The parameters of the ETC signals may therefore vary according to the therapy needed. In such a case, the test period should include samples of cardiac beat IEGM signals recorded for each of the different available ETC signals which may be delivered to the tissue in order to provide the cardiologist with enough samples of the different parameters of the artifacts induced by the application of the various different ETC signals.

Thus, the duration of the refractory period 128 should be set such as to prevent the erroneous detection of the ETC induced artifact for all the possible forms of deliverable ETC signals, including those ETC signal forms having the longest duration and the highest peak amplitude, taking into account the selected detection threshold level and the amplitude and duration of the various forms of ETC induced electrical artifacts.

Reference is now made to FIGS. 11, 12A, 12B, and 13, which are schematic diagrams useful for understanding the details of different types of ETC signal delivery inhibition in accordance with a preferred embodiment of the present invention.

Figure 11:
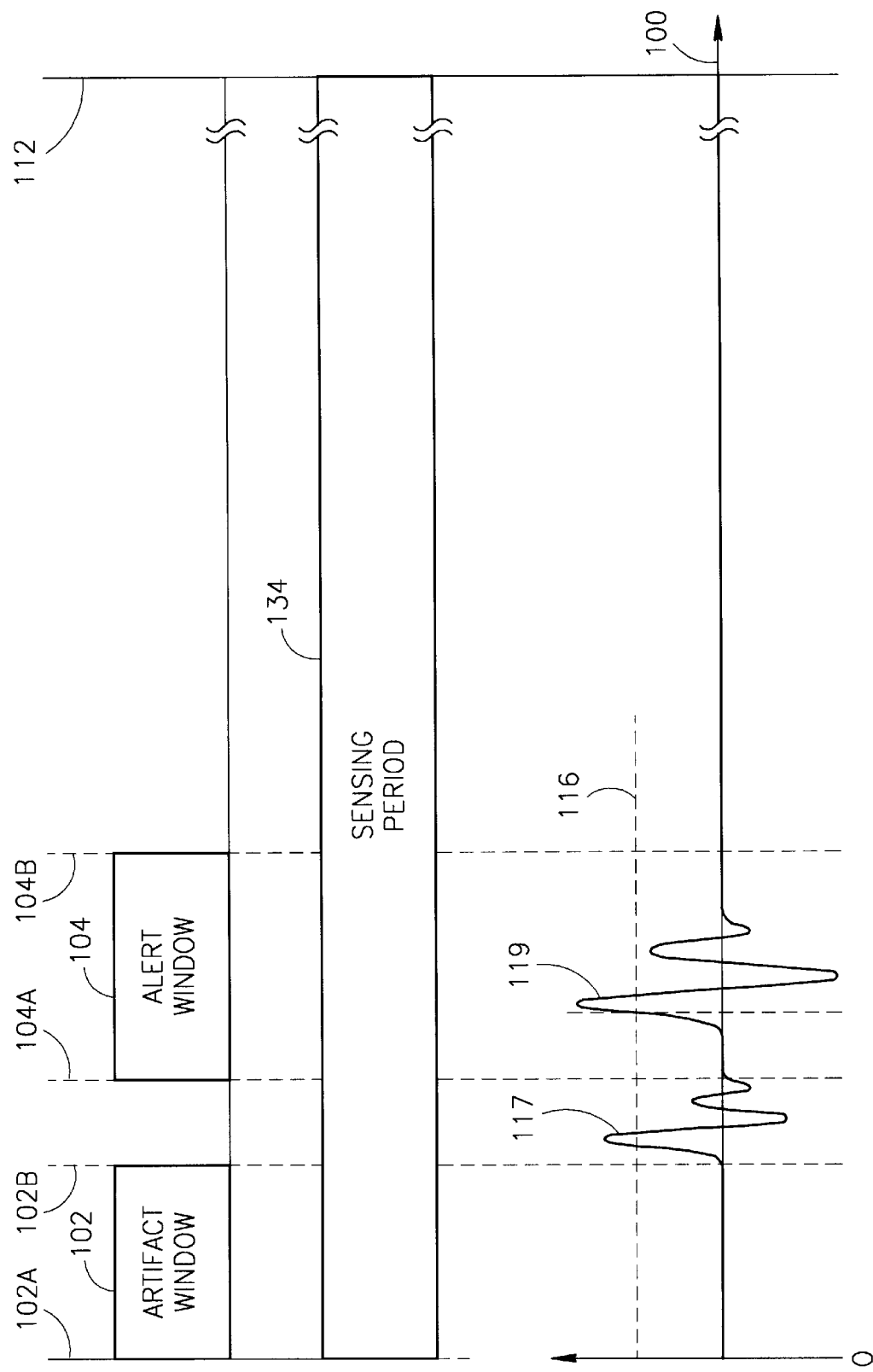
FIGS. 11, 12A, 12B, and 13 are schematic diagrams useful for understanding the details of different types of ETC signal delivery inhibition in accordance with a preferred embodiment of the present invention.

In FIG. 11 a situation is schematically illustrated in which no pacing has occurred in the RV. This may happen for example when a naturally occurring RV activation was sensed in the RV within the AV delay interval as is known in the art of pacemakers. The duration of the artifact window 102 and the alert window 104, and the value of the threshold level 116 are as disclosed in FIG. 9. Due to the lack of pacing, no pacing artifact signal is detected. However a threshold crossing signal 117 occurs in the time period defined between the end of the artifact window 102 and the beginning of the alert window 104. The signal 117 may be associated with an ectopic beat, or with an electrical noise which is not related to cardiac activity. The signal 117 is followed by a second threshold crossing signal 119 which is detected within the duration of the alert window 104. in such a case, the occurrence of the signal 117 inhibits the delivery of ETC signal to the heart within the current beat cycle even though the threshold crossing of the signal 119 occurred within the duration of the alert window 104. In such a case the use of a refractory period such as the refractory period 128 of FIG. 9 is obviated and the entire duration of the beat cycle constitutes an uninterrupted sensing period 134.

It is noted that if a threshold crossing signal (not shown) occurs within the current beat cycle at a time point after the end of the alert window 104, there is a definite probability that such a signal represents an ectopic beat and the delivery of an ETC signal in the next beat cycle which follows the current beat cycle is inhibited to prevent potentially arrhythmogenic ETC signal delivery.

Figure 12A:
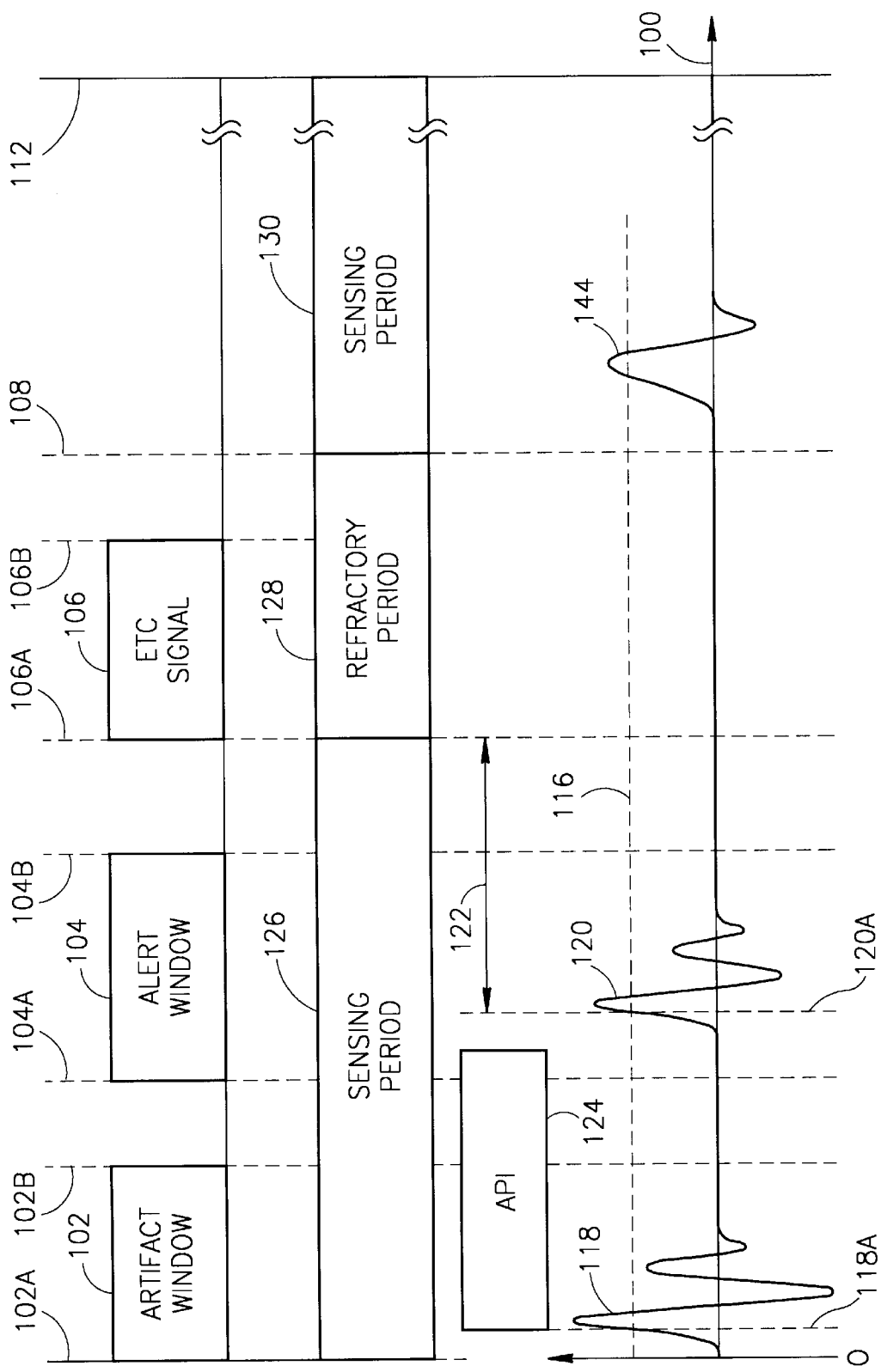

In FIG. 12A, the threshold crossing signals 118 and 120 are similar to those of FIG. 9, except that in FIG. 12A an additional signal 144 crosses the threshold level 116 within the duration of the sensing period 130. Since the signal 144 may represent an ectopic beat, the delivery of an ETC signal in the next beat cycle which follows the current beat cycle is inhibited. This next beat cycle starts at the trigger signal represented by the vertical line 112. Thus, even if a threshold crossing electrical signal occurs within the duration of the alert window (not shown) of the next beat cycle (only partially shown in FIG. 12A), the delivery of an ETC signal in the next beat cycle is inhibited (not enabled). This is an additional reason why the enabling of ETC signal delivery in a beat cycle by a threshold crossing detected signal occurring within the duration of the alert window was referred to as "conditional enabling" as disclosed hereinabove.

Figure 12B:
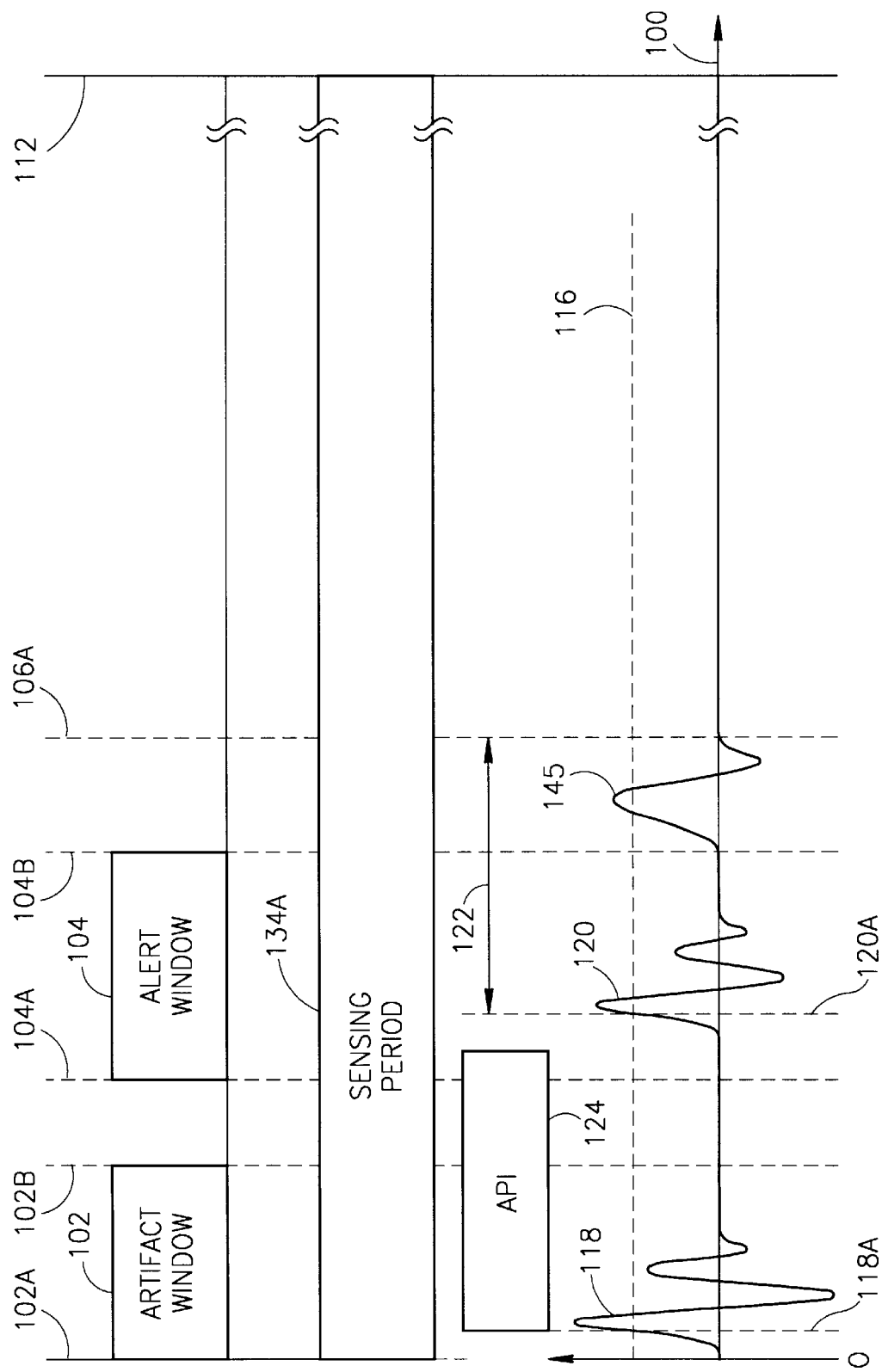

In FIG. 12B, the threshold crossing signals 118 and 120 are similar to those of FIG. 9, except that in FIG. 12B an additional signal 145 crosses the threshold level 116. The threshold crossing signal 145 occurs within the time period delimited between the end of the alert window 104 (schematically represented by the dashed vertical line 104B) and the vertical dashed line 106A. The detection of the threshold crossing signal 120 within the duration of the alert window 104 conditionally enables the delivery of an ETC signal (not shown) as disclosed hereinabove. The vertical dashed line 106A of FIG. 12B represents the computed starting time at which an ETC signal would have been started within the current beat cycle if the additional threshold crossing signal 145 would not have occurred.

The occurrence of any threshold crossing signal (such as for example the signal 145 of FIG. 12B) within the time period delimited between the end 104B of the alert window 104 and the computed starting time 106A of the conditionally enabled ETC signal, is defined as an inhibitory event within the current beat cycle and therefore inhibits the delivery of an ETC signal within the current beat cycle.

However, in contrast to the threshold crossing signal 144 of FIG. 12A which inhibits the delivery of an ETC signal in the beat cycle immediately following the current beat cycle (referred to as the next beat cycle), the occurrence of a threshold crossing signal such as for example the signal 145 within the time period delimited between the end 104B of the alert window 104 and the computed starting time 106A of the conditionally enabled ETC signal, does not inhibit the delivery of an ETC signal in the next beat cycle (of FIG. 12B).

In FIG. 12B, no refractory period is implemented due to the inhibition of ETC signal delivery within the current beat cycle. Therefore, the sensing period 134A of FIG. 12B is an uninterrupted sensing period lasting for the entire duration of the current beat cycle.

Figure 13:
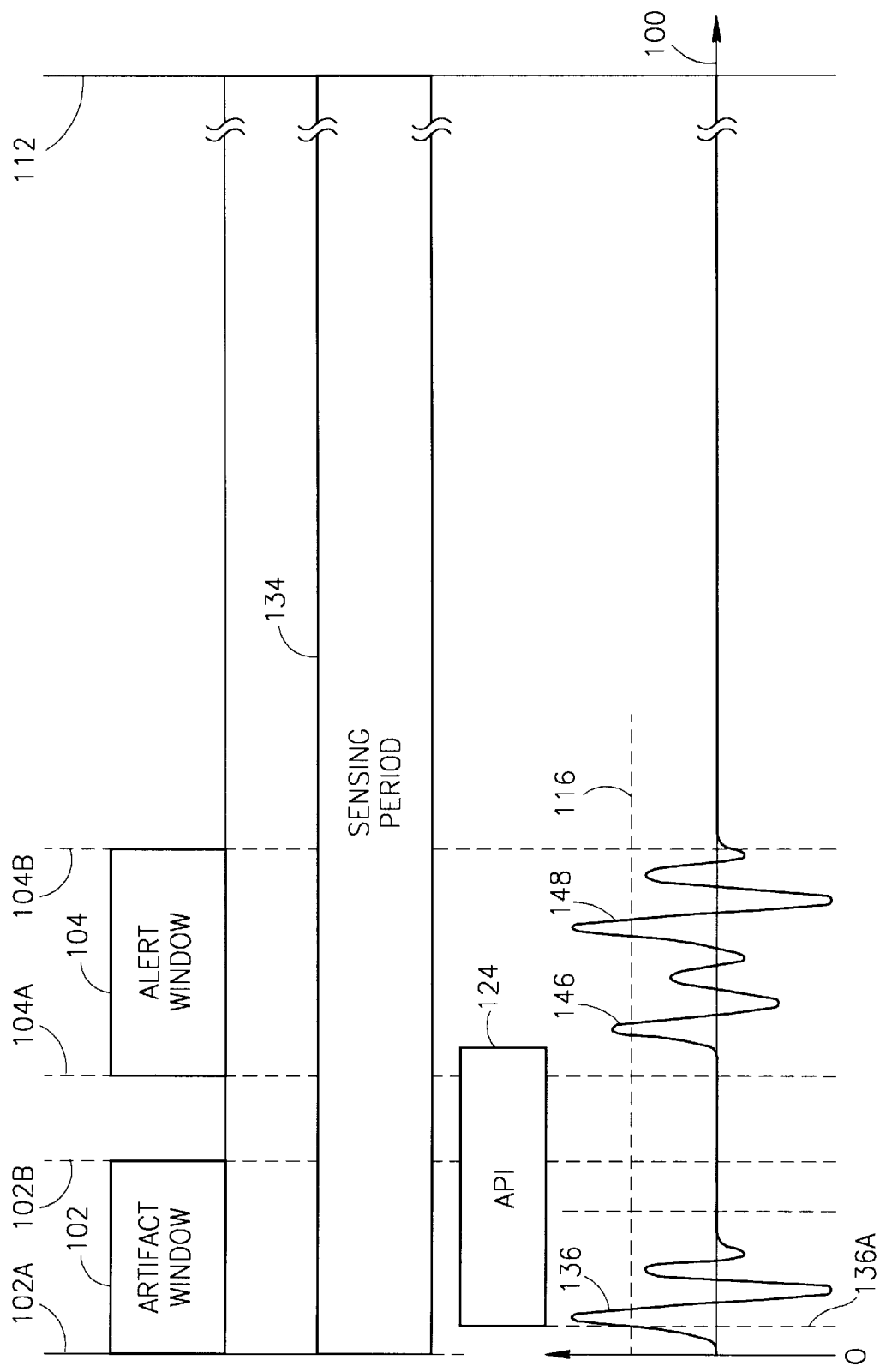

In FIG. 13 a situation is schematically illustrated in which pacing has occurred in the RV. The artifact window 102 and the alert window 104 are identical to the artifact window 102 and the alert window 104 of FIG. 9.

A pacing artifact signal 136 crosses the threshold 116 at the time represented by the point of intersection of the time axis 100 with the vertical dashed line 136A. The API 124 starts at the time of the first threshold crossing of the artifact signal 136. A second threshold crossing signal 146 occurs within the duration at the alert window 104. This signal is interpreted by the method as a valid detected signal resulting in a conditional enabling of ETC signal delivery. However, a third threshold crossing signal 148 occurs after the second threshold crossing signal 146. The third threshold crossing signal 148 may be an ectopic beat related signal, an external electrical noise associated signal or even a signal representing true LV activation (for example, the last possibility may occur in a case in which the second threshold crossing signal itself was really a noise signal or an ectopic beat which occurred within the duration of the alert window 104, while the third threshold crossing signal 148 was the true LV activation signal). However, since the method of the present invention cannot predict which of the signals occurring within the duration of the alert window 104 is the true LV activation, the ETC device such as, for example the ETC devices 1, of FIG. 1 inhibits the delivery of an ETC signal to the LV within the duration of the current beat cycle (which is represented by the time interval between the vertical lines 102A and 112. This inhibition of the conditionally enabled ETC signal delivery thus avoids the delivery of ETC signals with "wrong" timing which are potentially arrhythmogenic and thus increases the safety of ETC signal delivery.

Generally, the first threshold crossing signal (such as for example the signal 146 of FIG. 13) which is detected within the duration of the alert window 104 is always interpreted as a valid (or true) detected event and results in conditional enabling of ETC signal delivery, while any threshold crossing signal detected within the duration of the alert window 104 after the time of detection of the first detected signal always leads to inhibition of ETC signal delivery.

The method disclosed hereinabove is adapted for ETC devices having single chamber pacing capabilities. For example, the method may be used in ETC devices in which the RA is paced and sensed and the trigger signal for starting the timing of the LV sense is an RA sense event or an RA pace event detected in the RA sensing electrode or electrodes. Similarly, such a method may be used in ETC devices in which the RV is paced and sensed and the trigger signal for starting the timing of the LV sense is an RV sense event or an RV pace event detected in the RV sensing electrode or electrodes. However, if the ETC device includes dual chamber sensing capabilities with or without dual chamber pacing capabilities, the method may be adapted for use in a dual-chamber sensing/pacing situation. The method may be adapted to make use of the information available from sensing in the RA and the RV or the information available in the system or the device about the pacing of the RA or the RV or the RA and the RV. This available information may be used to overcome the problem of undesired inhibition of ETC signal delivery by the detection of threshold crossing far field sensed electrical artifacts or pacing associated electrical artifacts in the locally sensed LV electrogram associated.

For example, In the case that the RA sensed activation is used as the trigger signal, the electrogram signal sensed in the LV may include a first threshold crossing artifact signal associated with the RA pacing signal, but may also include a second threshold crossing artifact signal associated with an RV pacing signal which was delivered to the right ventricle after atrial pacing. This second pacing artifact may be erroneously detected as a valid detected LV activation and such a detection may result in wrong timing of the ETC signal.

Even in cases where no pacing occurs within a beat cycle, the locally sensed LV electrogram signal may include threshold crossing far field sensed artifacts associated with RA activation, RV activation or with both RA and RV activation.

Furthermore, under certain recording conditions, two threshold crossing far field artifacts associated with RA activation and RV activation may be sensed in the LV sensing electrode within a single beat cycle. For example, when the RV sense event or the RV pace event are used as the trigger signal for the local LV sensing such as is illustrated in the schematic diagram of FIG. 12A, the signal 144 may represent a threshold crossing far field sensed artifact associated with right atrial activation. In such a case, the inhibition of ETC delivery in the next beat cycle which results could have been avoided, since the signal 144 was a far field artifact due to atrial activation and not to an ectopic beat. Information about the possible duration of such far field sensed artifacts may be obtained in the test session performed by the cardiologist as disclosed hereinabove. Thus, it is possible to define a time window which is associated with the parameters of the far field sensed artifact associated with RA activation and to use this time window and the timing of detection of RA activation in the RA sensing electrode to prevent the inhibition of ETC signal delivery in the next beat cycle.

Thus, in ETC devices having single or dual chamber sensing and pacing capabilities, it may be desired to avoid the erroneous identification of detected far field sensed artifacts or pacing artifacts as ectopic beats and the subsequent inhibition of ETC signal delivery in the current beat cycle or in the next beat cycle which may result from such an erroneous detection.

It is noted that, while in the method disclosed hereinabove and illustrated in FIGS. 9–13 the trigger event which serves to start the timing of the left ventricular sensing is sensed in the right ventricle (RV), other preferred embodiments of the method may be implemented in which the trigger event is sensed in the right atrium (RA) as is disclosed in detail hereinabove. For example, the lead 2 of FIG. 1 may include a pacing electrode (not shown) for pacing the RA and a sensing electrode (not shown) for sensing the trigger signal which is either a pacing artifact if the RA was paced or a sensed natural activation of the RA due to the natural atrial rhythm. In this case, the method is similar to the above disclosed method except that the artifact window 102 is started at the time of threshold crossing of the signal sensed at the RA sensing electrode. When atrial sensing is used for providing the atrial trigger event, the artifact window 102, the alert window 104, the ETC delay 122 and artifact proximity interval 124 may be different than the corresponding values used in the embodiment having RA sensed trigger event due, inter alia, to the different distances between the RA and LV electrodes, the different cardiac activation propagation paths and the different amplitude and time coarse of the LV sensed atrial pacing associated artifacts. The artifact window 102, the alert window 104, the ETC delay 122 and artifact proximity interval 124 will have to be determined manually in a test session as disclosed in detail hereinabove.

Figure 14:
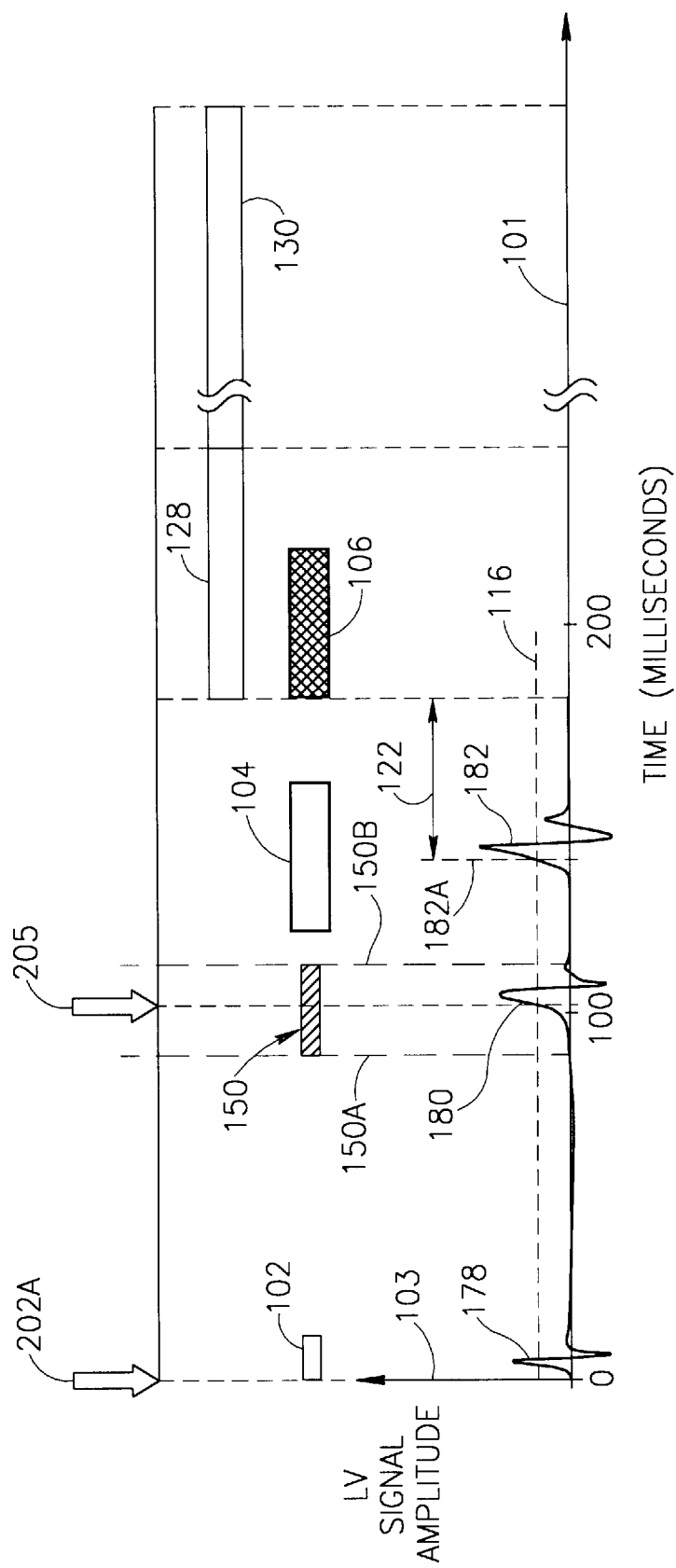
FIGS. 14–16 are schematic diagrams useful for understanding the details of the method of controlling ETC signal delivery to the heart adapted for use in patients with dual chamber sensing, in accordance with another preferred embodiment of the present invention.
Figure 15:
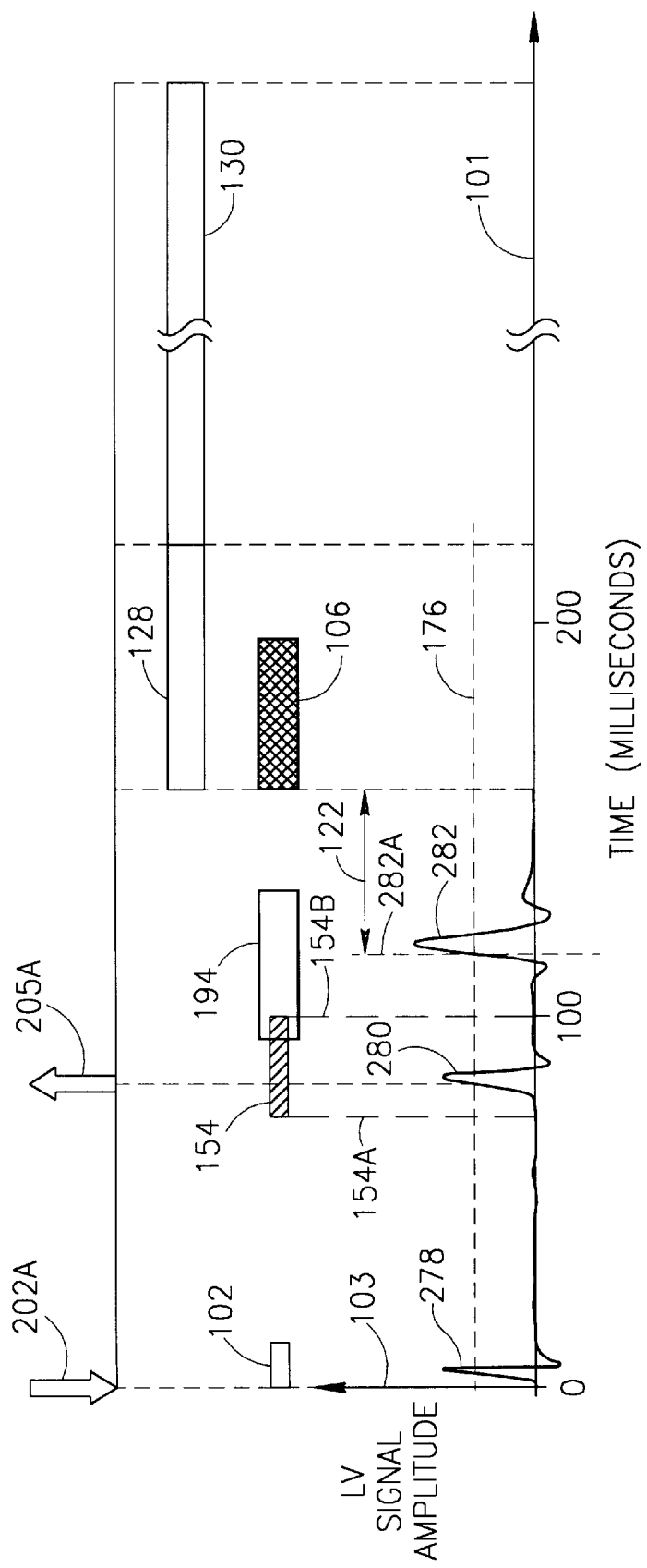
Figure 16:
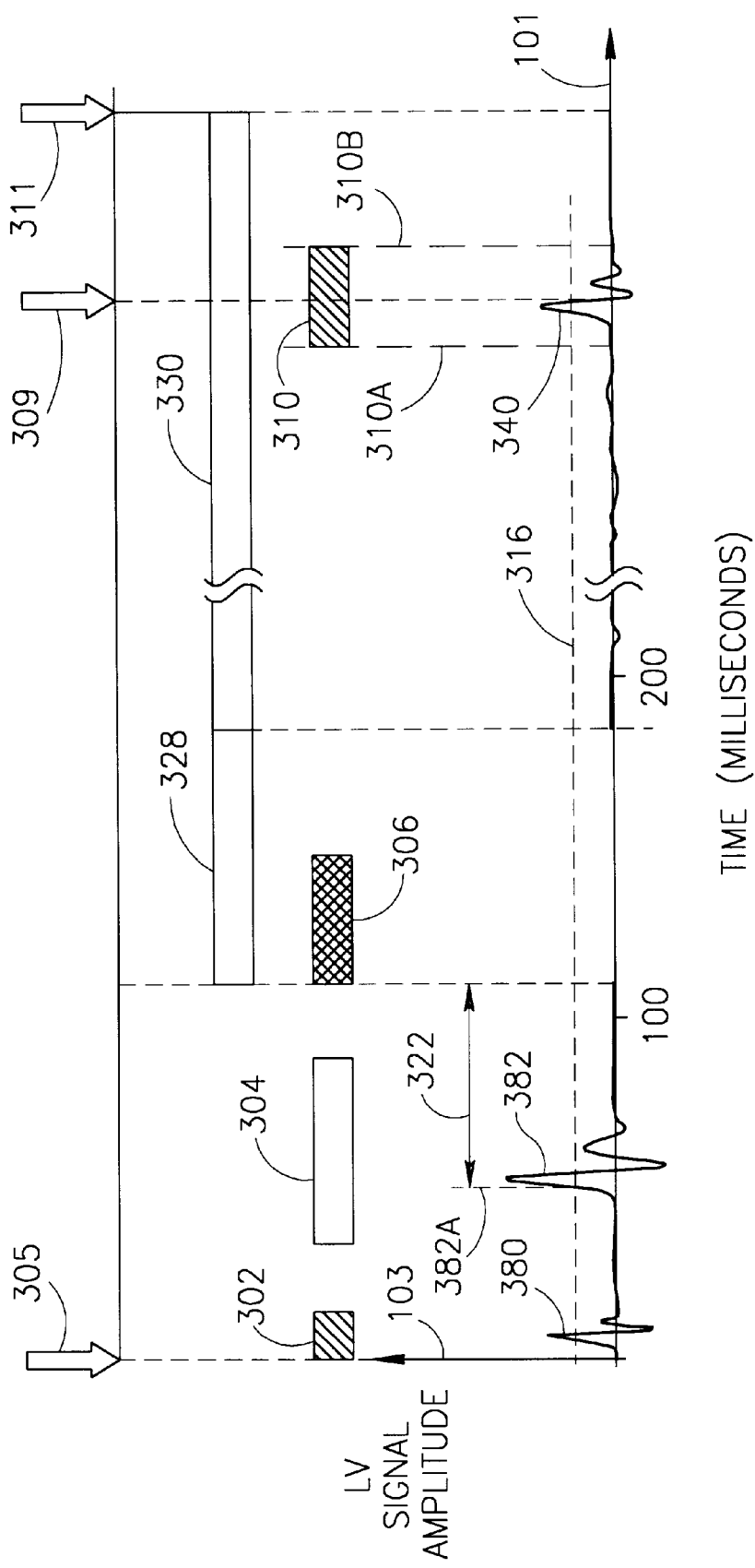

Reference is now made to FIGS. 14–16, which are schematic diagrams useful for understanding the details of the method of controlling ETC signal delivery to the heart adapted for use in patients with dual chamber sensing, in accordance with another preferred embodiment of the present invention.

In FIGS. 14–16, the horizontal axes 101 represent time in milliseconds and the vertical axes 103 represent the locally sensed LV electrogram signal amplitude in arbitrary units.

FIGS. 14 and 15 illustrate cases in which the trigger event 202A is an RA trigger event such as a detected RA sense or a signal associated with pacing of the RA such as a logical RA pacing command signal or an RA sensed pacing signal, while FIG. 16 illustrates a case in which the trigger event 305 is an RV trigger event such as a detected RV sense or a signal associated with pacing of the RV such as a logical RV pacing command signal or an RV sensed pacing signal.

In FIG. 14 an artifact window 102 (represented by the horizontal bar labeled 102) starts at the time of occurrence of the trigger event 202A. The signal 178 schematically represents a threshold crossing locally sensed LV electrical artifact signal associated with the right atrial pacing (for a case in which the RA was paced) or with the natural non-paced right atrial activation (for a case in which natural right atrial activation occurred. The signal 178 crosses the detection threshold 116 and is therefore detected as an event. The artifact signal 180 represents a threshold crossing locally sensed LV artifact signal associated with the right ventricular pacing artifact or with the natural non-paced right ventricular activation. A timing event 205 is schematically represented by the arrow labeled 205.

The horizontal hatched bar labeled 150 of FIG. 14, schematically represents a second artifact window 150. The second artifact window time period 150 represents a time interval during which the detection of the artifact signal 180 is expected. The parameters of the second artifact window 150 are calculated using the time of occurrence of the timing event 205. The duration of the second artifact window 150 is based on data recorded in the patient in a test period or test session as disclosed in detail hereinafter.

The timing event 205 generally represents an event which is used for the computation of the parameters of the second artifact window period 150. Different types of timing events are used for paced and sensed beats as is disclosed in detail hereinafter. The computation of the beginning time 150A and ending time 150B of the second artifact window 150 is based on the time of occurrence of the timing event 205 and on the values of a set of selected reconstruction parameters which are stored in the memory of the device or the system which is used to implement the method of timing of the present invention. Different sets of stored reconstruction parameters may be selected and used for computing the beginning time 150A and ending time 150B of the second artifact window 150, depending on the type of the timing event 205 as disclosed in detail hereinafter. The type of the timing event 205 may vary from beat cycle to beat cycle depending on whether the cardiac chamber with which the timing event is associated was paced or was activated without pacing.

For example, in a cardiac beat cycle in which the timing event 205 represents the time of generation of the right ventricular pacing command or any other suitable signal which is associated therewith, the artifact signal 180 represents the threshold crossing locally sensed LV artifact signal associated with the right ventricular pacing artifact. In a specific non-limiting example, if the device 21 of FIG. 3 is used for implementing the method, the timing event 205 may represent the time of generation of the logical command signal which is sent from the controller unit 40 (FIG. 3) to the pacing core 34 (FIG.3) to initiate pacing of the right ventricle by the pacing core 34. However, the timing event 205 may also represent the time of occurrence of other signals including but not limited to logical signals or any other suitable signals which are temporally linked to or synchronic with the delivery of a pacing pulse to the RV by any of the above disclosed implantable or non-implantable ETC devices. In another non-limiting example, the timing event 205 may represent the time of generating of a logical pulse by the processing unit 61 (FIG. 5) for initiating a right ventricular pacing pulse by the pacing unit 68 (FIG. 5).

In another beat cycle of the same heart, the timing event 205 is the time of detection of a right ventricular event by the right ventricular sensing electrode (such as, but not limited to, one of the electrodes 4A of the lead 4 of FIG. 1) and the artifact signal 180 represents the threshold crossing locally sensed LV far field artifact signal associated with the natural non-paced right atrial activation. Thus, If right ventricular event detection is performed using a single threshold crossing criterion, the timing event 205 represents the time at which the sensed right ventricular electrogram signal (not shown) crossed a right ventricular detection threshold level (not shown). However, if other different detection criteria are used to detect right ventricular activation, the timing event 205 represents the time of detection of a right ventricular activation, in accordance with the specific detection criterion or detection criteria used, as is disclosed in detail hereinafter.

Any detection of a threshold crossing signal which happens within the duration of the second artifact window 150 is ignored. Thus, the information available beforehand about the time period within which the artifact signal 180 is likely to be detected is used to identify the signal 180 as an expected artifact and to avoid the inhibition of ETC signal delivery within the current beat cycle.

If the timing event 205 which is detected by the system (such as but not limited to the system 60 of FIG. 5), or by the device (such as, but not limited to, the device 21 of FIG. 3) is a right ventricular sensed event, the system or the device selects an appropriate set of reconstruction parameters from the reconstruction parameter sets stored in the memory. This reconstruction parameter set was determined and stored in the memory of the device or the system based on the results from a recorded plurality of cardiac beats in which the right ventricle was sensed (This may happen, for example, when the RV was not paced and the electrical activation of the RV is due to the spread of a depolarization wave propagating from the right atrium following intrinsic natural activation of the right atrium or pacing of the right atrium). The device or system uses the selected set of reconstruction parameters and the time of occurrence of the timing event 205 to compute the beginning time 150A and ending time 150B of the second artifact window period 150. The beginning time 150A and ending time 150B are the time points between which the signal 180 is expected to occur in the current (sensed) cardiac beat.

Similarly, if the timing event 205 which is detected by the system (such as but not limited to the system 60 of FIG. 5), or by the device (such as, but not limited to, the device 21 of FIG. 3) is a right ventricular pacing associated event such as but not limited to a right ventricular pacing command or another event which is time linked to pacing of the right ventricle, the system or the device selects an appropriate set of reconstruction parameters from the reconstruction parameter sets stored in the memory. This reconstruction parameter set was determined and stored in the memory of the device or the system based on the results from a recorded plurality of cardiac beats in which the right ventricle was paced. The device or system uses the selected set of reconstruction parameters and the time of occurrence of the pacing related timing event 205 to compute the beginning time 150A and ending time 150B of the second artifact window period 150. The beginning time 150A and ending time 150B are the time points between which the signal 180 (representing the right ventricular pacing artifact signal) is expected to occur in the current (paced) cardiac beat.

This utilization of the information available on the natural activation or the pacing of the RV to avoid the inhibiting of the ETC signal delivery within the current beat cycle is advantageous since it may increase the overall efficacy of ETC signal delivery, without significantly increasing the risk of potentially arrhythmogenic ETC timing errors, in patients with dual chamber pacing. This increase in overall ETC therapy efficacy occurs because the unnecessary inhibition of ETC signal delivery due to the detection of the expected artifact signal 180 is avoided, which effectively increases the number of ETC signals which can be safely delivered to the LV.

The second artifact window period 150 is a dynamically computed time period. The computation of the beginning time point 150A and the ending time point 150B of the second artifact window 150 is performed on the fly by the processor or controller (not shown) of the ETC device in which the method is implemented. The need for dynamically computing the time points 150A and 150B arises from the fact that while the duration of the second artifact window 150 is a value which may be determined in a test session as is disclosed in detail hereinafter, and may be stored in the ETC device of the present invention, the exact timing of detection of the RV activation (RV sense) or of the logical or command pulse associated with the pacing of the RV (RV pace) is not known in advance and varies from beat to beat. Therefore, one cannot predict the exact time of occurrence of the timing event 205 within the cardiac beat cycle. The variability in the time of occurrence of the timing event 205 is due to, inter alia, natural or patho-physiological variability in cardiac tissue excitability, cardiac conduction velocity, changes in sympathetic or parasympathetic cardiac influences, changes in the heart rate, or the like.

In accordance with one preferred embodiment of the present invention, when the test session is performed in the patient, the cardiologist or physician may store and display the LV locally sensed electrogram signals using the timing event 205 as a synchronizing signal. For example, in accordance with one preferred embodiment of the present invention, portions of the recorded LV locally sensed electrogram signals may be displayed, individually (one by one) or simultaneously (in groups) or superimposed on one another or in any other suitable form on a display device, such that the time point of the synchronizing signal (i.e. the timing event 205) is positioned approximately at the center of the display to enable the cardiologist to observe the position of the artifact signal of each of the displayed portions (such as but not limited to the artifact signal 180 of the beat illustrated in FIG. 14). It is noted that when such a display method is used, the artifact signal of each of the recorded portions of the electrogram signals may occur to the left of or to the right of or superimposed on the time point representing the timing signal 205 for each portion, depending on, inter alia, electrode and lead structure and positioning, the cardiac conditions of the particular patient tested, and on the type and implementation of the timing event 205. The cardiologist may then use movable cursors displayed on the display device to determine and set the duration of the second artifact window 150 which is acceptable.

It will be appreciated by those skilled in the art that the particular type of the implementation disclosed hereinabove for displaying the results of the test session and for selecting and setting of the duration of the second artifact window 150 is given by way of example only, and that many other ways of displaying the results of the test session and of determining the duration of the second artifact window 150 are possible as is known in the art. Any such suitable method known in the art may be used in the present invention.

Such a form of display enables the determination of the duration of the artifact signal 180. The cardiologist may thus determine the duration of the second artifact window 150 by manually moving one or more cursors on the display (such as, for example, the display unit 32 of FIGS. 5–6) to determine and/or set the time points 150A and 150B. The time points 150A and 150B are set such that most or all the artifact signals (such as the artifact signal 180 of FIG. 14) recorded in the test session cross the threshold level 116 within the duration of the second artifact window 150. Care must be taken to avoid selection and setting of an unnecessarily long duration of the second artifact window 150, since this will result in unnecessarily increasing the probability of the occurrence of an ectopic beat within the duration of the second artifact window 150. It is noted that if an ectopic beat does occur within the duration of the second artifact window 150, it will be ignored by the system or the device and will therefore not result in the inhibition of the delivery of the ETC signal to the heart which may increase the risk of inducing an arrhythmia.

Thus, the setting of the duration of the second artifact window 150, involves a compromise between setting a duration the second artifact window 150 which is long enough such that a substantial percentage of the threshold crossings by the artifact signals 180 happen within the duration of the second artifact window 150, and setting a duration the second artifact window 150 which is short enough such as not to unduly increase the probability of occurrence of an ectopic beat therewithin. If patient safety considerations require so, the duration of the second artifact window 150 may be shortened by the cardiologist at the expense of reducing the ETC therapy efficacy. Thus, the duration of the second artifact window 150 is manually and empirically set by the cardiologist.

After the cardiologist sets the desired beginning time point 150A and ending time point 150B of the second artifact window 150 by suitable positioning of the cursors representing them or by any other suitable method known in the art, the system 60 of FIG. 5 or any other system suitable for implementing the method disclosed hereinabove computes the value of a first reconstruction parameter representing the position of the beginning point 150A relative to the position of the timing event 205 on the time axis 101, and of a second reconstruction parameter representing the position of the ending point 150B relative to the position of the timing event 205 on the time axis 101. The computed first and second reconstruction parameters are stored or programmed into the system 60 (FIG. 5) or the implantable device 21 (FIG. 3), or into any suitable ETC device adapted for implementing the method of the present invention, for use in "on the fly" computation of the position of the second artifact window 150 based on the time value of the timing event 205 of the current beat.

In accordance with one non-limiting example, the value of the first reconstruction parameter is computed by subtracting the time value of the timing event 205 from the time value of the beginning time point 150A, and the value of the second reconstruction parameter is computed by subtracting the time value of the ending time point 150B from the time value of the timing event 205. Preferably, the computation of the reconstruction parameters is performed in a way which is "transparent" to the cardiologist, meaning that the cardiologist just moves one or more cursors on the display to the positions delimiting the desired boundaries of the second artifact window 150, such as for example by positioning two cursors such that a sufficient portion of the artifact signal 180 is disposed between the two cursors for all of the displayed electrogram portions, and the values of the reconstruction parameters will be automatically computed by the system or the device and may also be downloaded or otherwise communicated (telemetrically or non-telemetrically) for storage in the device 21 or the system 60, or the like. It is noted that the procedure disclosed hereinabove for graphically determining the values of the first and second reconstruction parameters may be performed on a single artifact signal, on an averaged signal obtained by averaging a plurality of artifact signals recorded in different cardiac beats, on a plurality of simultaneously displayed artifact signals recorded in different cardiac beats, on a cumulative time histogram displaying times of threshold crossings obtained from a plurality of different artifact signals recorded in different cardiac beats, or by using any other suitable graphical display method for displaying artifact signal parameters which is known in the art.

It is noted that the particular method of computing the values of the first and second reconstruction parameters disclosed hereinabove is given by way of example only and that any other computation methods known in the art may be used.

After the first and second reconstruction parameters are computed and stored in the ETC device or system, the beginning time point 150A and the ending time point 150B may be computed on the fly for each individual cardiac beat by adding the value of first reconstruction parameter and of the second reconstruction parameter, respectively, to the time value of the timing event 205 received or sensed in the current beat cycle.

It is noted that the values of the first and second reconstruction parameters may vary for paced beats and sensed beats. This may happen because the activation wave propagates differently through the heart in paced and sensed cardiac beats. Typically, the activation spreads slower in paced beats than in sensed beats. Additionally, the duration and waveform of the artifact signal recorded in a paced beat may vary considerably from those of the far field artifact signal recorded in a sensed beat. It may therefore be necessary for the cardiologist to determine two different sets of reconstruction parameters for computing the beginning time point 150A and the ending time point 150B of the second artifact window 150 on the fly.

For example, in a patient in which RV pacing occurs which is accompanied by a threshold crossing pacing artifact sensed by the LV local sensing electrode (not shown), and in which the positioning of the various cardiac electrodes is such that the LV local sensing electrode also records a threshold crossing far field sensed artifact due to RV natural activation, the cardiologist has to determine the parameters of the second artifact window 150 for two different recorded sets of patient data including one data set recorded for beats in which the RV was paced (paced beats) and another data set recorded for beats in which the RV was not paced (sensed beats). The cardiologist then sets or stores two different sets of computed reconstruction parameters in the system or the device. A first reconstruction parameter set is used for paced beats and a second reconstruction parameter set is used for sensed beats.

When the ETC device or system is operative, the controller unit 40 of the device 21 (FIG. 3) or the processing unit 61 of the system 60 (FIG. 5) uses the appropriate set of reconstruction parameters based on the available information whether the beat is a paced or sensed beat. If a pacing command was issued by the controller unit 40 or by the processor unit 61, the controller unit 40 or the processor unit 61 will use the first set of reconstruction parameters for computing the beginning and ending time points 150A and 150B. If a pacing command was not issued by the controller unit 40 or by the processor unit 61 the controller unit 40 or the processor unit 61 will use the second set of reconstruction parameters for computing the beginning and ending time points 150A and 150B.

Returning to FIG. 14, the temporal sequence of events in the current beat cycle schematically illustrated in FIG. 14 develops in the following order. Upon occurrence of the trigger event 202A in the RA, the ETC signal delivery is initially disabled. The artifact signal 178 (which may represent a right atrial pacing electrical artifact in a paced beat or a threshold crossing RA activation associated far field sensed event in a sensed beat) occurs within the duration of the artifact window 102 and is therefore ignored by the system or the device, and does not cause inhibiting of ETC signal delivery. After the timing event 205 occurs, the controller unit 40 of the device 21 or the processing unit 61 of the system 60 selects the appropriate set of reconstruction parameters, based on whether the RV was paced or sensed, as disclosed hereinabove, and uses the selected set of reconstruction parameters to compute on the fly the values of beginning time point 150A and the ending time point 150B. This computation may require some time. The controller unit 40 of the device 21 or the processing unit 61 of the system 60 then checks whether the threshold crossing of the threshold 116 by the artifact signal 180 occurred within the duration of the second artifact window 150. If the threshold crossing of the threshold 116 by the artifact signal 180 occurred within the duration of the second artifact window 150 as is illustrated in FIG. 14, the system ignores this threshold crossing, since it is interpreted as being due to an expected artifact signal and not due to an ectopic beat.

If the threshold crossing of the threshold 116 by the artifact signal 180 did not occur within the duration of the second artifact window 150 (not shown), the system inhibits the delivery of an ETC signal within the current beat cycle, since the artifact signal 180 is interpreted as being due to an unexpected "noise" which may possibly be due to an ectopic beat.

Thus, in the case illustrated in FIG. 14, the system ignores the threshold crossing by the artifact signal 180. The local sensing in the LV continues to check whether a threshold crossing occurred within the duration of the alert window as disclosed hereinabove. The crossing of the threshold 116 by the an LV sensed event 182 happens within the duration of the alert window 104. The controller unit 40 of the device 21 or the processing unit 61 of the system 60 therefore enable the delivery of an ETC signal 106 after a delay period 122 as disclosed in detail hereinabove. The refractory period 128 and the sensing period 130 are implemented as disclosed in detail hereinabove and illustrated in FIG. 9.

It is noted that, generally, if a threshold crossing event (not shown in FIG. 14) is detected at any time within the cardiac beat cycle other than within the duration of the first artifact window 102, the second artifact window 150 and the alert window 104, the first instance of possible delivery of ETC signal is inhibited, whether it occurs within the current cardiac beat cycle or within the next cardiac beat cycle. For example, in FIG. 14, if in addition to the signals 178, 180, and 182, a threshold crossing signal (not shown) would have occurred between the end of the alert window 104 and the beginning time of the conditionally enabled ETC signal 106, the delivery of the conditionally enabled ETC signal 106 of the current beat cycle is inhibited, but the delivery of an ETC signal (not shown) within the next cycle is not unconditionally inhibited. This means that the delivery of an ETC signal in the next beat cycle may or may not be inhibited according to those signals as disclosed in detail hereinabove.

In another example, if in FIG. 14 the threshold crossing signal 182 would not have occurred within the duration of the alert window 104 and a threshold crossing signal (not shown) would have occurred after the end of the alert window 104, the delivery of an ETC signal in the next beat cycle would be inhibited irrespective of the signals which will be detected within the duration of the next beat cycle.

The term inhibited is used here to indicate that such an inhibition overrides any conditional enabling of the delivery of ETC signal (due to an event detected within the duration of the alert window 104) which occurred before or after the inhibition occurred.

It is further noted that, in the case illustrated in FIG. 14, no artifact proximity interval (API) is being used since the artifact signal 178 is temporally well separated from the alert window 104. However, in accordance with another preferred embodiment of the invention, an API may also be used together with the method of computation of the second artifact interval 150 on the fly, as disclosed in detail hereinabove and illustrated in FIGS. 10A, 10B, 12A, 12B, and 13. In the case of the use of an API (not shown) in combination with the method illustrated in FIG. 14, the occurrence of a detected event within the part of the API which does not overlap the first artifact window 102, is also defined as an inhibitory event (in addition to the other inhibitory events disclosed hereinabove) which inhibits the delivery of an ETC signal to the heart (even if the event detected within the part of the API which does not overlap the first artifact window 102 occurs within the duration of the alert window 104).

It is still further noted that, the decisions (by the controller unit 40 of the device 21 or the processing unit 61 of the system 60) of enabling or of inhibiting the delivery of an ETC signal within the current or the next beat cycle as disclosed in detail hereinabove need not be made immediately upon the detection of a threshold crossing event. Rather, the computation of the temporal parameters of the second artifact window and the alert window may be performed and the various time values of detected threshold crossing events may be stored in memory such as but not limited to the memory units 44 (FIG. 3) and memory unit 66 (FIG. 5). The checking whether a threshold crossing event occurred within the duration of the second artifact window 150 is performed after the computation of the time points 150A and 150B. The exact timing of the decision may depend, inter alia, on the speed of computation of the controller unit 40 of the device 21 or of the processing unit 61 of the system 60 or of any other microprocessor or processing unit used in implementing the device of the present invention.

In FIG. 15, in which the cardiac beat cycle is a cycle in which the trigger event 202A represents the pacing of the RA and in which the RV was sensed to activate without need for RV pacing. The artifact signal 278 is a far field sensed RA pacing artifact which falls within the duration of the first artifact window 102. However, while in the cardiac beat cycle illustrated in FIG. 14, the RV was paced, in the cardiac beat cycle illustrated in FIG. 15, the RV is activated by the normal atrio-ventricular conduction path and the RV sensing electrode (such as but not limited to the electrode 4A of FIG. 1) senses the RV activation. Therefore, a timing event 205A (schematically indicated by the arrow labeled 205A) represents the time of detection of the RV sensed event. The sensed RV event electrogram signal itself is not shown in FIG. 15.

The signal 280 represents the far field sensed electrical artifact due to right ventricular activation as recorded in the locally sensed LV electrogram. The hatched horizontal bar labeled 154 represents a second artifact window 154. The beginning time point 154A and the ending time point 154B of the second artifact window 154 are computed using the value of the timing event 205A and the values of the two reconstruction parameters of the second set of reconstruction parameters, similar to the computation disclosed hereinabove of the values of the beginning and ending time points 150A and 150B, respectively, of the second artifact window 150 of FIG. 14.

Since the signal 280 crossed the threshold 176 within the duration of the second artifact window 154 it is interpreted as an expected artifact and is ignored. The signal 282 represents a threshold crossing locally sensed LV activation event which occurs within the duration of the alert window 194. The detection of the signal 282 conditionally enables the delivery of an ETC signal to the heart, as disclosed in detail hereinabove. The controller unit 40 of the device 21 or the processing unit 61 of the system 60 therefore enable the delivery of an ETC signal 106 after a delay period 122 as disclosed in detail hereinabove. The refractory period 128 and the sensing period 130 are implemented as disclosed in detail hereinabove and illustrated in FIGS. 9 and 14.

It is noted that, as explained hereinabove, although the cardiac beat cycles schematically illustrated in FIGS. 14 and 15 may represent beat cycles recorded in the same heart with the same electrode placements, the duration and temporal positioning within the beat cycle duration of the second artifact window 150 of FIG. 14 are not identical to the duration and temporal positioning within the beat cycle duration of the second artifact window 154 of FIG. 15. For example, the second artifact window 154 partially overlaps the alert window 194 of FIG. 15, while the second artifact window 150 does not overlap the alert window 104 of FIG. 14.

It will be appreciated by those skilled in the art that the values of the positions and the duration of the second alert windows 150 and 154 are schematically shown by way of example only, may vary from those illustrated in FIGS. 14 and 15, respectively, and may depend, inter alia, on the type of the electrodes and leads used and on their disposition in or about the heart, on various electrical parameters of the myocardium and on the patient's heart rate.

It is noted, that in cases in which RV activation related signals are used as trigger event for controlling the delivery of ETC signals to the heart as disclosed hereinabove, if the right atrium is paced, it is possible that electrical artifact signals associated with right atrial pacing will be locally sensed by the LV sensing electrode. These artifacts may occur at a time after the delivery of the ETC signal to the heart. Additionally, under some electrogram recording conditions and electrode placements it is possible that electrical artifact signals associated with far field sensed right atrial electrical activation will be locally sensed by the LV sensing electrode. If these artifact signals are detected as events by crossing the set detection threshold or according to any other detection method known in the art which is implemented for detecting LV locally sensed events, they may cause an undesirable inhibiting of the ETC signal delivery in the next beat cycle, as disclosed in detail hereinabove (see FIG. 12A). Such an inhibition is undesirable since it may reduce the efficacy of cardiac ETC therapy by reducing the number of ETC signals which are delivered to the heart. However, such unnecessary inhibition may be avoided by properly defining a third artifact window which is computed in relation to a second timing event FIG. 16 illustrates another preferred embodiment of the method of the present invention in which the events associated with RV activation are used as the trigger event. In this preferred embodiment, one of the electrodes 4A of the lead 4 (FIG.1) may be used for sensing and pacing the RV, or alternatively, one of the electrodes 4A may be used for RV sensing and another one of the electrodes 4A may be used for RV pacing. One of the electrodes 6A is used for locally sensing the LV electrogram signal. The ETC signal may be delivered by one or more of the electrodes 6A of the lead 6 (FIG.1). One of the electrodes 2A of the lead 2 (FIG.1) may be used for sensing and pacing the RA, or alternatively, one of the electrodes 2A may be used for sensing the RA and another one of the electrodes 2A may be used for pacing the RA.

The arrow labeled 305 of FIG. 16 schematically represents the time of occurrence of a trigger event 305. The trigger event itself (not shown for the sake of clarity of illustration) may be any suitable signal which is indicative of RV activation, either by pacing or due to the intrinsic cardiac rhythm. The trigger event 305 may be implemented in different ways. For example, the trigger event 305 may be a logical pulse or any other suitable type of electrical signal indicative of a detected right ventricular activation event (RV sense) or a right ventricular pacing event (RV pace). Such a logical pulse may be provided by any suitable detecting circuitry or sensing/detecting unit such as, but not limited to the sensing units 38 of FIG. 3. The trigger event 305 may also be a logical signal or any other suitable type of signal provided by a microprocessor or a controller unit which controls the ETC device, such as but not limited to the controller unit 40 of FIG. 3 and the processing unit 61 of FIG. 5, as disclosed in detail hereinabove.

Turning back to FIG. 16, the first artifact window 302 is similar to the artifact window 102 of FIG. 9. The artifact signal 380 represents a detected LV locally sensed RV pacing associated artifact signal (when RV pacing occurred) as disclosed in detail hereinabove. The artifact signal 380 may also represent a detected LV locally sensed non-paced RV activation associated artifact signal (when RV activation was due to activation wave spreading from the right atrium), as disclosed in detail hereinabove. The artifact 380 crosses the threshold 316 and is therefore detected as an event.

Since the detected artifact signal 380 of FIG. 16 occurs within the duration of the first artifact window 302, the artifact signal 380 is interpreted as an expected event and is ignored by the system and does not cause ETC signal delivery inhibition. A detected event 382 crosses the threshold 316 at a time represented by the vertical dashed line 382A which is within the duration of the alert window 304. The detection of the event 382 results in the conditional enabling of the delivery of an ETC signal as disclosed hereinabove. The horizontal cross-hatched bar 306 represents the duration of the ETC signal delivered to the heart (the actual ETC signal is not shown in FIG. 16, for the sake of clarity of illustration) after a delay represented schematically by the double headed arrow labeled 322. The horizontal bar 328 represents a refractory period for preventing the detection of the ETC signal induced artifact, as disclosed hereinabove for the refractory period 128 of FIG. 9.

A sensing period 330 (schematically represented by the horizontal bar labeled 330) begins after the ending of the refractory period 328. The signal 340 represents a detected LV locally sensed electrical artifact signal which crosses the threshold 316. The time of occurrence of a timing event 309 is schematically represented by the arrow labeled 309. In the particular beat cycle illustrated in FIG. 16 the timing event 309 is the logical RA pacing command (the actual logical pulse is not shown in FIG. 16). However, other signals associated with the pacing of the RA may also be used as the timing event. For example, in cases in which the RA is not currently paced but in which a potentially threshold crossing far field sensed artifact signal associated with natural electrical activation of the RA is locally sensed in the LV, the time of occurrence of a detected RA event (such as but not limited to a threshold crossing sensed RA electrogram signal) may be used as the timing event 309. For example, in the device 21 of FIG. 1, one of the electrodes 2A of the right atrial lead 2 is used for detecting threshold crossing events in the right atrium to detect atrial activation, and the timing event 309 represents the time of detection of a right atrial activation event such as but not limited to the crossing of a preset threshold. However, the detection of the right atrial activation event may be performed using any suitable detection method known in the art. The hatched horizontal bar labeled 310 represents a third artifact window 310.

When the cardiologist performs the test session for collecting patient data as disclosed in detail hereinabove, the cardiologist may also collect data for computing the temporal parameters of the third artifact window 310. In accordance with a preferred embodiment of the present invention, when the test session is performed in the patient, the cardiologist or physician may store and display the LV locally sensed electrogram signals using the timing event 309 as a synchronizing signal using a method similar to that disclosed hereinabove for the second artifact window 150 and the timing event 205 of FIG. 14. Such a form of display enables the determination of the duration of the artifact signal 340 of FIG. 16. Similar to the method disclosed hereinabove, if the locally sensed LV electrogram recordings include both RA pacing associated artifacts and RA activation associated far field sensed artifacts, two different data sets may be collected from the patient, one data set includes recorded cardiac beats in which the RA is paced (RA paced beats), and another data set including recorded data sets in which the RA is naturally activated without pacing (RA sensed beats). Thus, two different sets of reconstruction parameters may be computed as disclosed in detail hereinabove from these different data sets and stored in the memory of the device or the system (not shown).

When the system or device are operative in the patient, the position of the beginning time 310A and the ending time 310B of the third artifact window 310 are computed on the fly, using a selected one of the two sets of reconstruction parameters in a manner similar to the method of the computing disclosed hereinabove for computing the beginning and ending time points 150A and 150B, respectively of the second artifact interval 150 of FIG. 14.

If the timing event 309 is an RA pacing command as disclosed hereinabove, the set of reconstruction parameters which was computed from the data set of RA paced beats is selected and used to compute the values of the beginning time 310A and the ending time 310B of the third artifact window 310.

If the timing event 309 is the detection of a right atrial activation, as disclosed hereinabove, the second set of reconstruction parameters computed from RA sensed beats is selected and used to compute the values of the beginning time 310A and the ending time 310B of the third artifact window 310. In the case of RA sensed beats, the timing event 309 which represents the time of detection of a right atrial event may occur before, after, or simultaneously with the time of detection of the LV locally sensed artifact signal 340. The relative timing of the timing event 309 and the time of detection of the LV locally sensed artifact signal 340 may depend, inter alia, on the particular detection algorithms or methods used for detecting events in the RA sense electrogram signal and in the LV locally sensed electrogram signal. However, the computation of the beginning time 310A and the ending time 310B of the third artifact window 310 need not necessarily be computed prior to the detection of the detected artifact signal 340 and the decision whether a detected event such as for example the artifact signal 340 has occurred within the duration of the artifact window 310 may be performed after the computation of the beginning time 310A and the ending time 310B of the third artifact window 310 has been completed.

It is noted that in the case of RA paced beats disclosed hereinabove, the timing event 309 which represents the time of occurrence of the RA pacing command may also occur before, after, or simultaneously with the time of detection of the LV locally sensed pacing associated artifact signal 340. This may happen since the generation of the pacing command may be performed by a unit which is separated from the controller or the processor which is used to compute the parameters of the third artifact window 310. The communication of the information about the initiation of the RA pacing command may thus require a definite time period and may therefore result in the timing event 309 being detected later than the time of detection of the artifact signal 340. For example, when the device 21 of FIG. 3 is used to implement the method of the present invention, the pacing core 34 may be directly connected (connection not shown in FIG. 3) to the sensing units 38 and may initiate pacing commands independently from the controller unit 40. While the pacing core 34 may communicate a signal indicative of the initiating of the pacing command to the controller unit 40, which signal may be used by the controller as the timing event 309, there may be a definite delay between the actual pacing of the heart such as RA pacing and the time of occurrence of detection of the timing event 309 by the controller unit 40. Therefore, it may be possible (though not necessary) that the time of detection of the artifact signal 340 will precede the time of detection of the timing event 309 by the controller or the processing unit used for computing the parameters of the third artifact window 310.

Thus, if a threshold crossing event such as the artifact signal 340 occurs within the duration of the computed third artifact window 310 it is interpreted as an expected event and is ignored by the device or the system. However, any detected event (not shown) which occurs within the duration of the sensing period 330 and is not within the duration of the artifact window 310 is interpreted as an unexpected event and the device or the system inhibits the delivery of an ETC signal in the next cardiac beat cycle (not shown in FIG. 16) which starts at the next RV associated trigger event 311.

The advantage of using the artifact window 310 is that the efficacy of ETC therapy may be increased by using the available information about the timing of expected artifact signals to avoid unnecessary inhibition of ETC signal delivery. Thus, using the preferred embodiment of the method disclosed hereinabove and illustrated in FIG. 16 more ETC signals may be delivered to the heart when required without significantly increasing the probability of delivering a wrongly timed ETC signal following an ectopic beat.

It is noted that, the beat cycle of FIG. 16 illustrates a case in which an ETC signal 306 was delivered within the current beat cycle. However, one may also encounter beat cycles recorded under similar conditions (with the same third artifact window 310) but in which an ETC signal has not been delivered to the heart within the current beat cycle. For example, if an event is detected in the time between the end of the artifact window 302 and the beginning of the alert window 304 of FIG. 16, no ETC signal is delivered within the current beat cycle. Other exemplary cases in which no ETC signal is delivered within the current beat cycle, may be a case (not shown in FIG. 16) in which two (or more) events are detected within the duration of the alert window 304, and a case in which an event is detected between the end of the alert window 304 and the beginning of the conditionally enabled ETC signal 306 of FIG. 16. Furthermore, other events disclosed hereinabove in detail with respect to the occurrence of a detected event within the duration of an API (such as the API 124) may also result in inhibiting the delivery of an ETC signal to the heart within the current beat cycle. In another, exemplary case, if no event is detected within the duration of the alert window 304, no ETC signal will be delivered within the current beat cycle. In any of these situations in which no ETC signal is delivered to the heart within the current beat cycle, it is still desirable to monitor detected events for the purpose of inhibiting the delivery of ETC signal in the next beat cycle (not shown) if a suspected event is detected. This is preferably implemented by programming the device or the system to inhibit the delivery of an ETC signal within the next beat cycle upon detecting an event (not shown) within a sensing period (not shown) which starts immediately after the end of the alert window 304 (FIG. 16) and ends at the next trigger event 311 (FIG. 16). However, if a threshold crossing signal such as for example the signal 382 occurs within the duration of the alert window 304 and another threshold crossing signal is detected after the end of the alert window 304 and before the time at which the conditionally enabled ETC signal 306 would have been delivered (thus, leading to inhibition of the delivery of ETC signal 306 of the current beat cycle), or if the detected event (not shown) occurs within the duration of the third artifact window 310 (FIG. 16), ETC delivery within the next beat cycle will not be inhibited. Thus, in accordance with a preferred embodiment of the present invention, in cardiac beats in which an ETC signal is not delivered to the heart within the current beat cycle because of any type of inhibition or other reason as disclosed hereinabove, any event detected within a sensing period starting at the end of the alert window 304 and ending at the next trigger event 311 inhibits the delivery of an ETC signal to the heart in the next beat cycle, except when this event is detected within the duration of the third artifact window 310.

It is noted that, while in the particular examples illustrated in FIGS. 14-15, the refractory period 128 of FIGS. 14 and 15 are shown to begin simultaneously with the delivered ETC signal 106, other preferred embodiments are possible in which the refractory period 128 of FIGS. 14–15 begin prior to the beginning of the ETC signal 106, as is disclosed in detail for the refractory period 128A of FIG. 9B hereinabove. Similarly, the refractory period 328 of FIG. 16 may also be adapted to begin prior to the beginning of the ETC signal 306, as disclosed hereinabove.

Figure 17A:
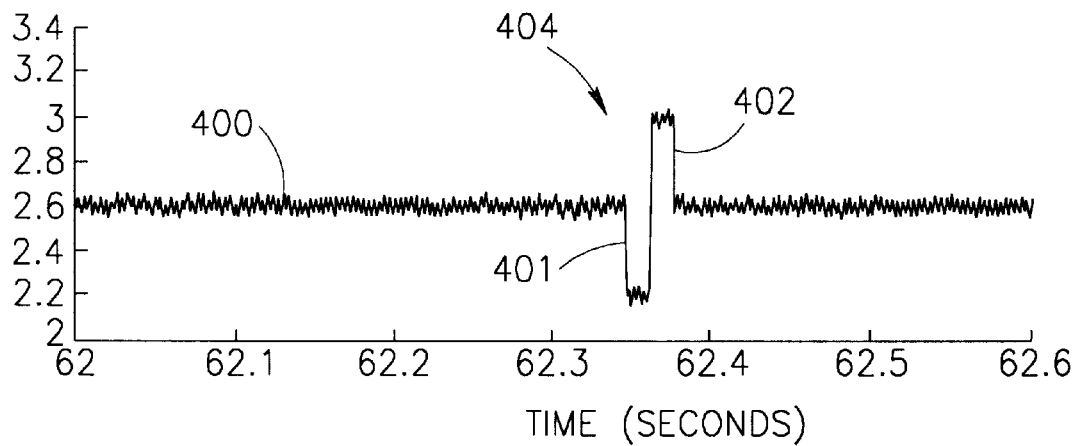
FIGS. 17A and 17B are graphs of experimental data illustrating electrical artifact signals in the sensed cardiac electrogram recorded about the left ventricle of the porcine heart during the delivery of an ETC signal.
Figure 17B:
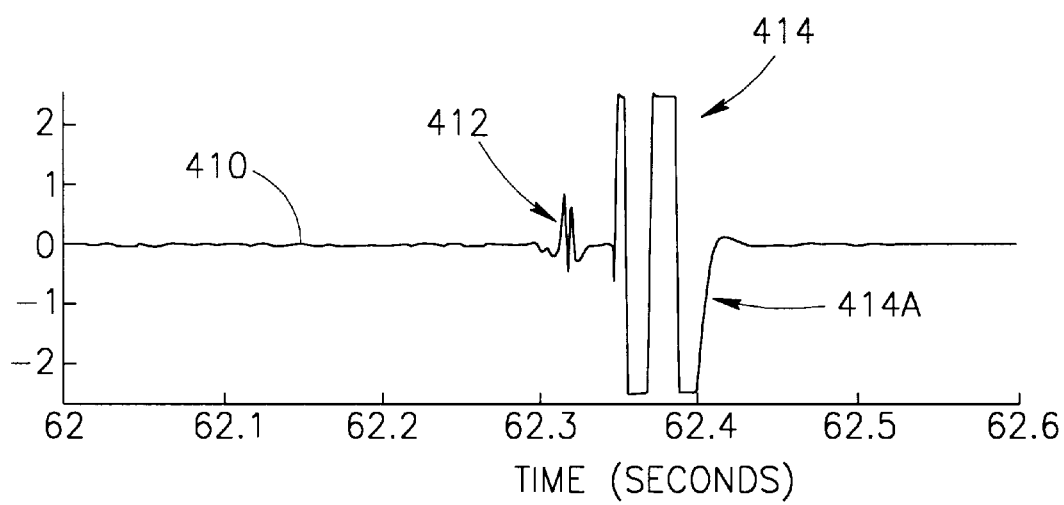

Reference is now made to FIGS. 17A and 17B which are graphs of experimental data illustrating electrical artifact signals in the sensed cardiac electrogram recorded about the left ventricle of the porcine heart during the delivery of an ETC signal.

The experimental results illustrated in FIGS. 17A and 17B include data recorded in vivo in a heart of an anaesthetized pig to which ETC signals were delivered. A lead (not shown) was inserted through the Vena Cava into a lateral branch of the great cardiac vein. The structure of the ETC lead (not shown) used for LV sensing and for delivering the ETC signals to the pig's heart is not the subject matter of the present invention and is therefore not described in detail hereinafter. Briefly, the ETC lead included a pair of sensing electrodes each extending approximately 1 millimeter along the longitudinal axis of the ETC lead and separated from each other along the longitudinal axis of the ETC lead by a distance of approximately 2 millimeters. A first coil-like ETC electrode is disposed on the ETC lead at a distance of approximately 2 millimeters from one of the sensing electrodes and a second coil-like ETC electrode was disposed on the ETC lead at a distance of approximately 2 millimeters from the remaining sensing electrode. Thus, the ETC electrodes symmetrically flanked the sensing electrodes. The sensing of the LV electrogram and the delivery of the ETC signals to the LV were thus performed through the wall of the lateral branch of the GCV. The sensing of the LV electrogram was performed by recording the voltage difference between the two sensing electrodes (differential recording).

The pair of ETC electrodes were used for delivering a biphasic ETC signal to the LV of the porcine heart. The horizontal axes of FIGS. 17A and 17B represent time in seconds.

The curve 400 of FIG. 17A is a logical signal representing the time course and amplitude of the ETC signal delivered to the porcine heart through the pair of ETC electrodes. The vertical axis of FIG. 17A represents the amplitude of the delivered of the ETC signal in arbitrary units. The ETC signal 404 is a biphasic square signal having a first square pulse component 401 and a second square pulse component 402 having a polarity which is opposite to the polarity of the first square pulse 401. The total duration of the biphasic ETC signal is approximately 30 milliseconds.

In FIG. 17B, the curve labeled 410 represents the differentially recorded LV locally sensed electrogram. The vertical axis of FIG. 17B represents the amplitude of the differentially recorded LV electrogram signal in arbitrary units. The polyphasic signal 412 of the electrogram curve 410 is the locally sensed signal associated with the sensed activation of the left ventricle. The artifact signal 414 represents the recorded electrical artifact signal induced by the ETC signal 404 of FIG. 17A. A potion of the artifact signal 414 is clipped due to amplifier saturation. The portion 414A of the artifact signal 414 is due to electrode polarization which persists longer than the duration of the ETC signal 404. The total duration of the ETC induced artifact signal 414 is approximately 90 milliseconds. The ETC induced artifact signal 414 is a relatively large artifact due to the high current intensity which is used and due to the proximity of the sensing electrodes (not shown) to the ETC electrodes (not shown).

From the results illustrated in FIGS. 17A and 17B it can be seen that a refractory period is needed to avoid detection of one or more portions of the ETC induced artifact signal 414 as a true event. The duration of the refractory period (not shown) depends, inter alia, on the detection method, on the particular type of electrodes and leads used, and the particular detection criterion or criteria which are used. In accordance with one non limiting example, a refractory period of approximately 100 milliseconds duration, starting a few milliseconds prior to the delivery of the ETC signal 404 may be useful for preventing erroneous detection of portions of the ETC induced artifact signal 414 as true events.

It will be appreciated by those skilled in the art that the data of FIGS. 17A and 17B is valid only for the porcine heart and for the particular ETC signal type, on the particular type of electrodes and leads used, and on the event detection method which is used and is given by way of a demonstrative example. However, results obtained in clinical studies in humans indicate that similar or different duration values may also be used for the refractory period in humans depending, inter alia, on the ETC signal intensity, duration and shape, the particular event detection method used, and on the type, construction and positioning of the sensing electrodes and the ETC electrodes.

Reference is now made to FIGS. 18A–18C and 19 which are graphs illustrating the shape and temporal sequence of cardiac electrical events including pacing artifacts and far field sensed artifacts recorded from the heart of a human patient with congestive heart failure (CHF).

Figure 18A:
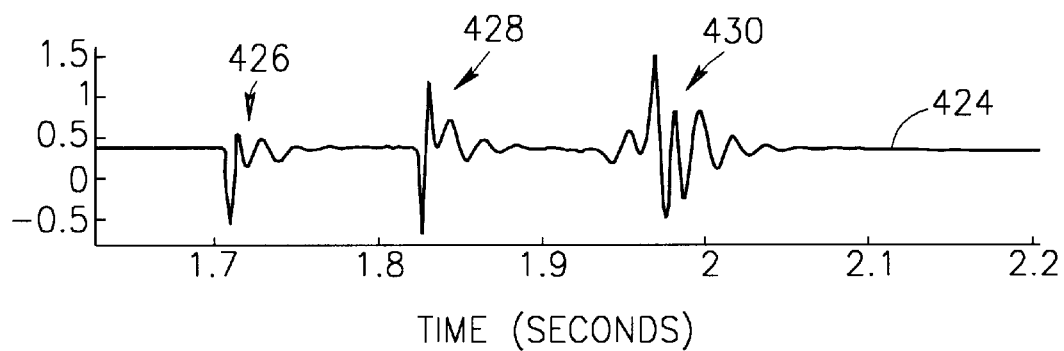
FIGS. 18A–18C, and 19 are graphs illustrating the shape and temporal sequence of cardiac electrical events including pacing artifacts and far field sensed artifacts recorded from the heart of a human patient with congestive heart failure (CHF)
Figure 18B:
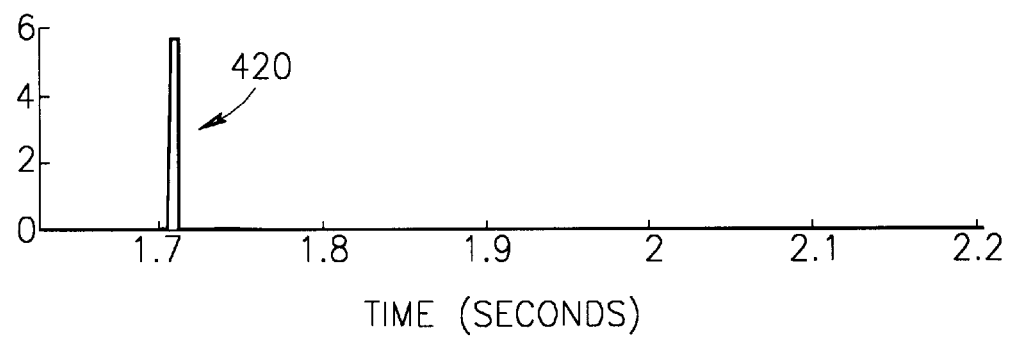
Figure 18C:
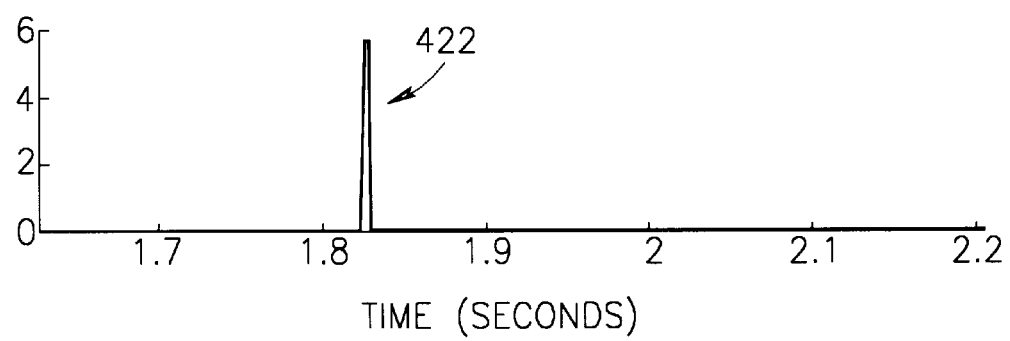
Figure 19:
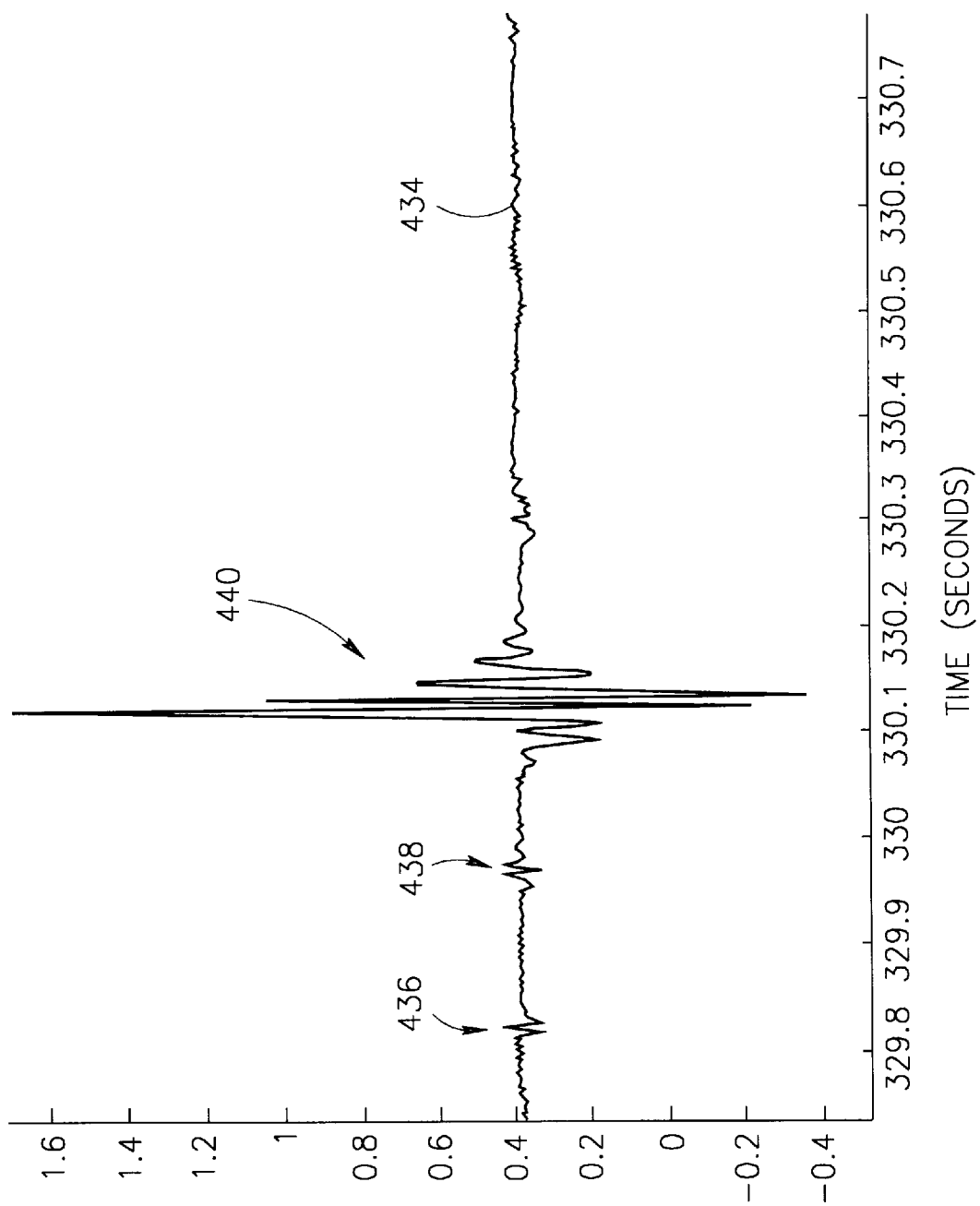

In FIGS. 18A–18C the horizontal axis represents the time in seconds. The vertical axis of FIG. 18A represents the amplitude in arbitrary units of the locally sensed left ventricular electrogram. The vertical axis of FIG. 18B represents the amplitude (in arbitrary units) of logical signals representing the timing of delivery of a pacing pulse to the right atrium of the patient, and the vertical axis of FIG. 18C represents the amplitude (in arbitrary units) of logical signals representing the timing of delivery of a pacing pulse to the right ventricle of the patient. In FIG. 19, the horizontal axis represents time in seconds. It is noted that the scale of the horizontal axis of FIG. 19 is different than the scale used for the horizontal axes of FIGS. 18A–18C. The vertical axis of FIG. 19 represents the amplitude in arbitrary units of the locally sensed left ventricular electrogram. It is noted that the scale of the vertical axis of FIG. 19 is different than the scale used for the vertical axis of FIG. 18A.

The square signal 420 of FIG. 18B represents the timing of a pacing pulse delivered to the RA of the patient using an atrial pacing lead as is known in the art. The square signal 422 of FIG. 18C represents the timing of a pacing pulse delivered to the RV of the patient using a right ventricular pacing lead. It is noted that the signals 420 and 422 do not represent the true amplitude of the pacing pulses and are indicative only of the timing of the pacing pulses delivered to the RA and the RV, respectively.

In addition to the RA pacing lead (not shown) and the RV pacing lead (not shown), the patient had a microcatheter having sensing electrodes and ETC electrodes disposed within a lateral branch of the GCV as is disclosed hereinabove. The ETC lead was inserted through the sub-clavian vein, passing through the SVC, the right atrium, the coronary sinus (CS) and the GCV and reaching a lateral vein of the GCV.

The structure of the microcatheter used for LV sensing and for delivering the ETC signals to the patient's heart is not the subject matter of the present invention and is therefore not described in detail hereinafter. Briefly, The ETC therapy was transvenously applied to the patient. A CARDIMA™ REVELATION™ microcatheter, product No. 01-082007, commercially available from CARDIMA Inc., CA, U.S.A., (not shown) was introduced through the coronary sinus (CS) of the patient into the great cardiac vein (GCV) and positioned in a branch of the GCV. The microcatheter includes 8 coil electrodes which are equally spaced along the microcatheter and one distal tip electrode that was not used. The ETC signals (also referred to as CCM signals) were transvenously delivered to the LV through a pair of electrodes selected from the six electrodes closest to the tip of the microcatheter. The sensing of the LV electrogram was performed by recording the voltage difference between the two sensing electrodes (differential recording).

The patient's heart was paced using overdrive DDD pacing with a short AV delay as is known in the art.

Turning to FIG. 18A, the curve 424 represents the left ventricular electrogram recorded within a cardiac beat cycle in the patient. The polyphasic signal 426 represents the artifact signal associated with the pacing of the RA as locally sensed by the sensing electrodes of the ETC lead. The polyphasic signal 428 represents the artifact signal associated with the pacing of the RV as locally sensed by the sensing electrodes of the ETC lead. The polyphasic signal 430 represents the sensed signal associated with LV activation as locally sensed by the sensing electrodes of the ETC lead. It is noted that in the particular beat cycle illustrated in FIG. 18A no ETC signal was delivered to the patient's heart and the signal 430 therefore represents the locally sensed LV activation only and does not include an ETC associated artifact component.

It is noted that the signals 426, 428 and 430 all exhibit ringing due to the particular type of the sense amplifiers used and due to signal filtering. The substantial amplitude of the artifact signals 426 and 428 associated with RA and RV pacing, respectively, relative to the amplitude of the signal 430 associated the LV activation, demonstrates the need for using the artifact window(s) as disclosed in detail hereinabove. It is clear that for certain event detection methods, such as for example a single threshold crossing detection method, one or more of the signals 426 and 428 may be erroneously detected as a valid event, depending, inter alia, on the particular detection threshold used, and may therefore unnecessarily cause undesired inhibition of ETC signal delivery. The use of artifact window may therefore be advantageously implemented in this case.

FIG. 19 illustrates the locally sensed left ventricular electrogram recorded in the same CHF patient is a second recording session different from the recording session part of which is illustrated in FIGS. 18A–18C. In this second session the dual chamber pacing and the delivery of ETC signals was discontinued and the patient's heart was allowed to beat at the intrinsic cardiac rhythm.

The curve 434 represents the left ventricular electrogram recorded within a non-paced cardiac beat cycle in the patient. The polyphasic signal 436 represents the far field sensed electrical artifact signal associated with the activation of the RA as locally sensed by the LV sensing electrodes of the ETC lead. The polyphasic signal 438 represents the electrical artifact signal associated with the activation of the RV as locally sensed by the LV sensing electrodes of the ETC lead. The polyphasic signal 440 represents the sensed signal associated with LV activation as locally sensed by the sensing electrodes of the ETC lead. It is noted that in the beat cycle illustrated in FIG. 19 no ETC signal was delivered to the patient's heart and the signal 440 therefore represents the locally sensed LV activation only and does not include an ETC associated artifact component.

It is noted that the amplitude of the signals 436 and 438 is relatively small compared to the amplitude of the signal 440. The particular electrode placement and the lead structure used in obtaining the recordings illustrated in FIGS. 18A and 19, resulted in relatively small far field sensed artifacts. In such a case, the detection criteria used may be easily adapted such that only the LV activation event will be detected. In accordance with one, non-limiting example this may be achieved by using a single threshold detection criterion and adjusting the threshold value level (not shown in FIG. 19) such that the signals 436 and 438 will not be detected. When this is done, the duration of the appropriate artifact windows may be set to zero during the data collection session as disclosed in detail hereinabove. For example, in the case CHF patient in which the data illustrated in FIGS. 18A–18C and 19 was recorded, if RV activation is used as the trigger event and the RV is not paced (such as schematically illustrated in FIG. 16), the duration of the third artifact window 310 may be set to zero (or effectively canceled), since the far field sensed artifact associated with RA activation will not be detected as a valid event due to suitable threshold selection and due to it's small amplitude compared to the amplitude of the LV locally sensed activation signal.

However, in patients in which one or more of the LV locally sensed far field sensed artifacts has characteristics which cause the detection of the artifact or artifacts as detected events by the detection criteria used for detecting the locally sensed LV activation, the use of the various artifact windows as disclosed in detail hereinabove may be advantageous for increasing the efficacy of ETC therapy.

In experiments in the porcine heart in which transvenous sensing and ETC signal delivery are performed in the porcine LV using an ETC lead as disclosed hereinabove with respect to the results illustrated in FIGS. 17A–17B, and in which single or dual chamber is performed as is known in the art, the artifact window 102 is in the range of approximately 0–10 milliseconds, the alert window 104 is in the range of approximately 20–50 milliseconds, the ETC delay 122 is in the range of approximately 20–100 milliseconds and the artifact proximity interval 124 is in the range of approximately 0–20 milliseconds. Typical values of the duration of the artifact windows 150, 154 and 310 are in the range of approximately 10–30 milliseconds. It will be appreciated by those skilled in the art, that while these value ranges were obtained in the porcine heart, similar (but not necessarily identical) value ranges may be suitable for use in human patients.

It is further noted that the above disclosed value ranges are given by way of example only and that other values and/or value ranges of the duration of the artifact window 102, the alert window 104, the ETC delay 122, the artifact proximity interval 124 and the artifact windows 150, 154 and 310 may also be used depending, inter alia, on the specific electrical characteristics of the electrodes and leads implanted in the heart, the specific locations of the various pacing and sensing electrodes and on cardiac tissue conditions. Thus these values may vary from patient to patient.

It will be appreciated by those skilled in the art that, while in all of the examples and embodiments of the present invention disclosed hereinabove and illustrated in the drawings, the event detection criterion used for detecting events in the locally sensed LV electrogram signal is a single threshold crossing method similar to the single threshold crossing criterion which is used in pacemakers as is known in the art, it is also possible to implement the method and the devices and systems of the present invention by using other different single or combined detection methods and algorithms which are known in the art for detecting cardiac events. Such use of other different detection criteria and their various combinations are included within the scope and spirit of the present invention.

The methods and the devices and systems of the present invention may be adapted for use with many different event detection methods which are known in the art. For example, one may use a double threshold detection criterion, which is known in the art in which the detection of a valid event involves the crossing of two different threshold values in a specific sequence (each of the thresholds may be positive or negative, depending, inter alia, on the shape and waveform of the signals which need to be detected).

In another non-limiting example, the detection criterion may be a combination of a single threshold value and a slope criterion. In this method, the slope of the signal determined within a specified time interval relative to the time of threshold crossing must be in a certain range of slope values for the signal to be detected as an event.

In another, non-limiting example, the signal detection method may be based on the use of various morphological signal parameters, as is known in the art. Such as, but not limited to, the detection methods listed by A. D. Mercando et al. in chapter 100, pp. 943–948, entitled "AUTOMATED DETECTION OF TACHICARDIAS BY ANTITACHICARDIA DEVICES" of the book "CARDIAC ELECTROPHYSIOLOGY FROM CELL TO BEDSIDE" Eds. Douglas P. Zipes and Jose Jalife, published by W. B. Saunders Company (1990).

Other detection methods based on signal morphology which may be used in the method of the present invention, include but are not limited to, the method disclosed by Jonathan J. Langberg et al. in the article entitled "IDENTIFICATION OF VENTRICULAR TACHICARDIA WITH USE OF THE MORPHOLOGY OF THE ENDOCARDIAL ELECTROGRAM", published in Circulation, Vol. 77, No. 6, pp. 1363–1369, 1988, and the method disclosed by Paul V. E. et al., in the article entitled "AUTOMATIC RECOGNITION OF VENTRICULAR ARRYTHMIAS USING TEMPORAL ELECTROGRAM ANALYSIS", published in Pace, Vol. 14., pp. 1265–1273 (1991).

It is noted that when using such detection methods other than the single threshold crossing method disclosed hereinabove, the method may possibly (but not necessarily) need to be adapted to accommodate for possible differences in the speed of detection. Such detection speed differences may arise from the need for performing additional computational procedures and the speed of event detection may depend, inter alia, on the specific algorithms used for implementing the event detection, and on the computational speed of the particular processor or controller (not shown) on which the detection program is operative. However, the method of the present invention as disclosed hereinabove allows the performing of some or all of the decisions regarding the enabling or the inhibiting of the delivery of ETC signals after the time of detection of the relevant events as long as the time required for performing the computations is not excessively long, and is therefore suitable for using detection methods which may require more time for detection of an event.

It is further noted that while, the method and devices and systems of the invention, disclose the use of a single threshold crossing method in implementing the sensing and pacing algorithms performed in the RA and or in the RV for performing single or dual chamber pacing as is well known in the art, it is also possible to perform the single or dual chamber pacing of the present invention by using other methods of event detection (in the RA, in the RV or in both the RA and the RV) by using any other suitable event detection method known in the art.

Figure 20A:
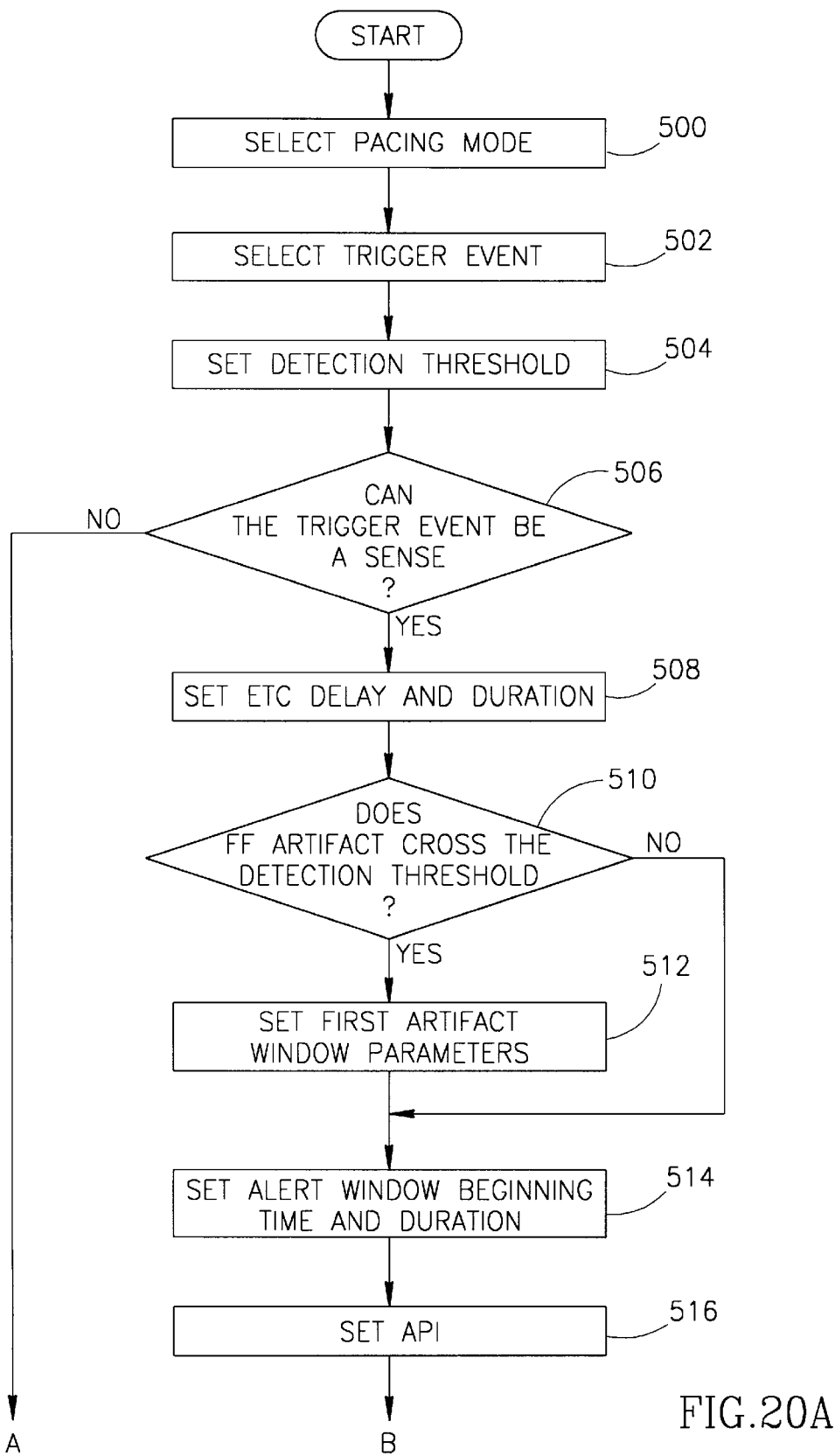
FIGS. 20A–20C are schematic flow diagrams illustrating the steps of a method for determining and setting the parameters required for setting and/or calculating of various time windows and intervals useful in the preferred embodiments of the method of the present invention.
Figure 20B:
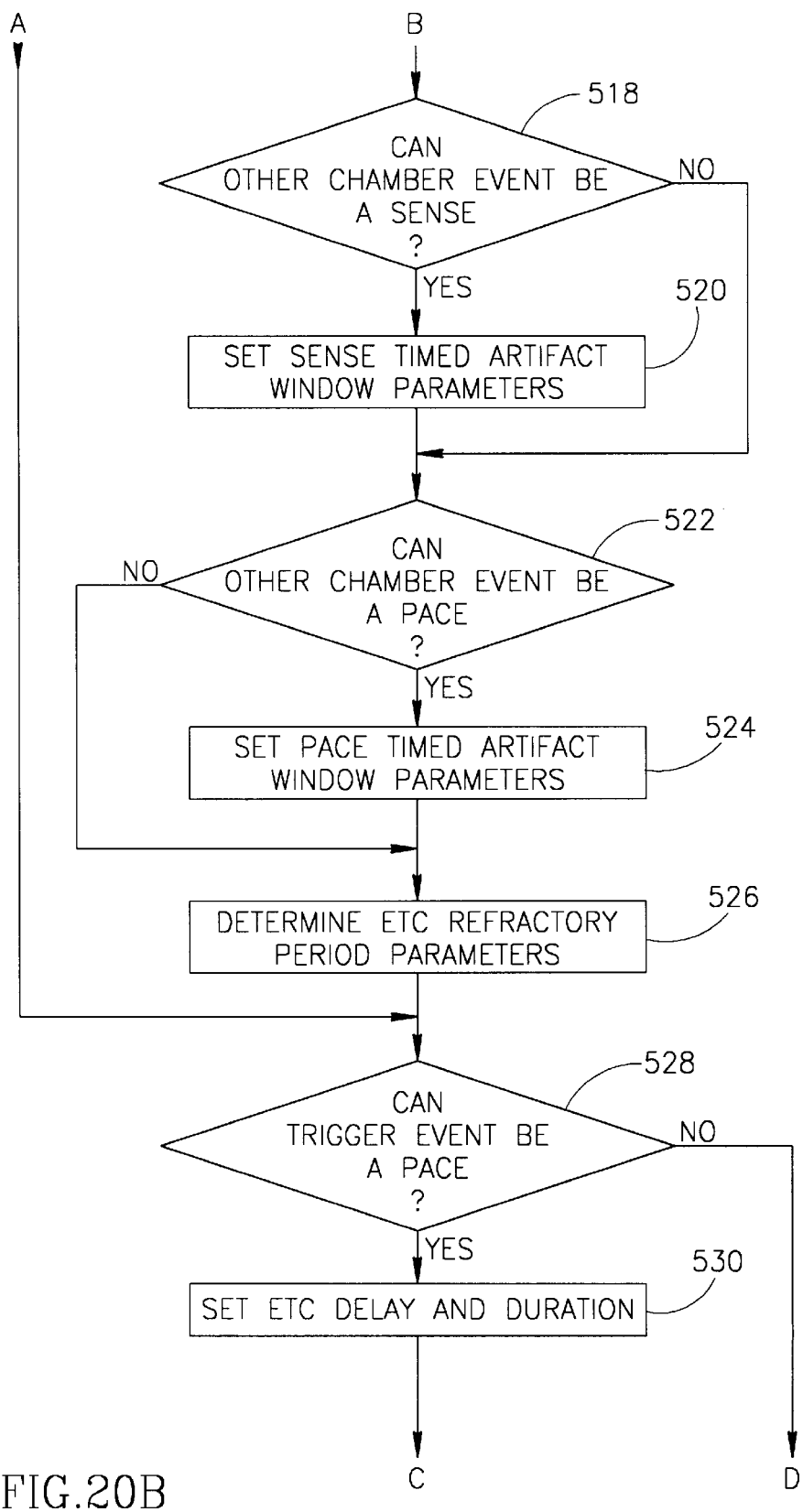
Figure 20C:
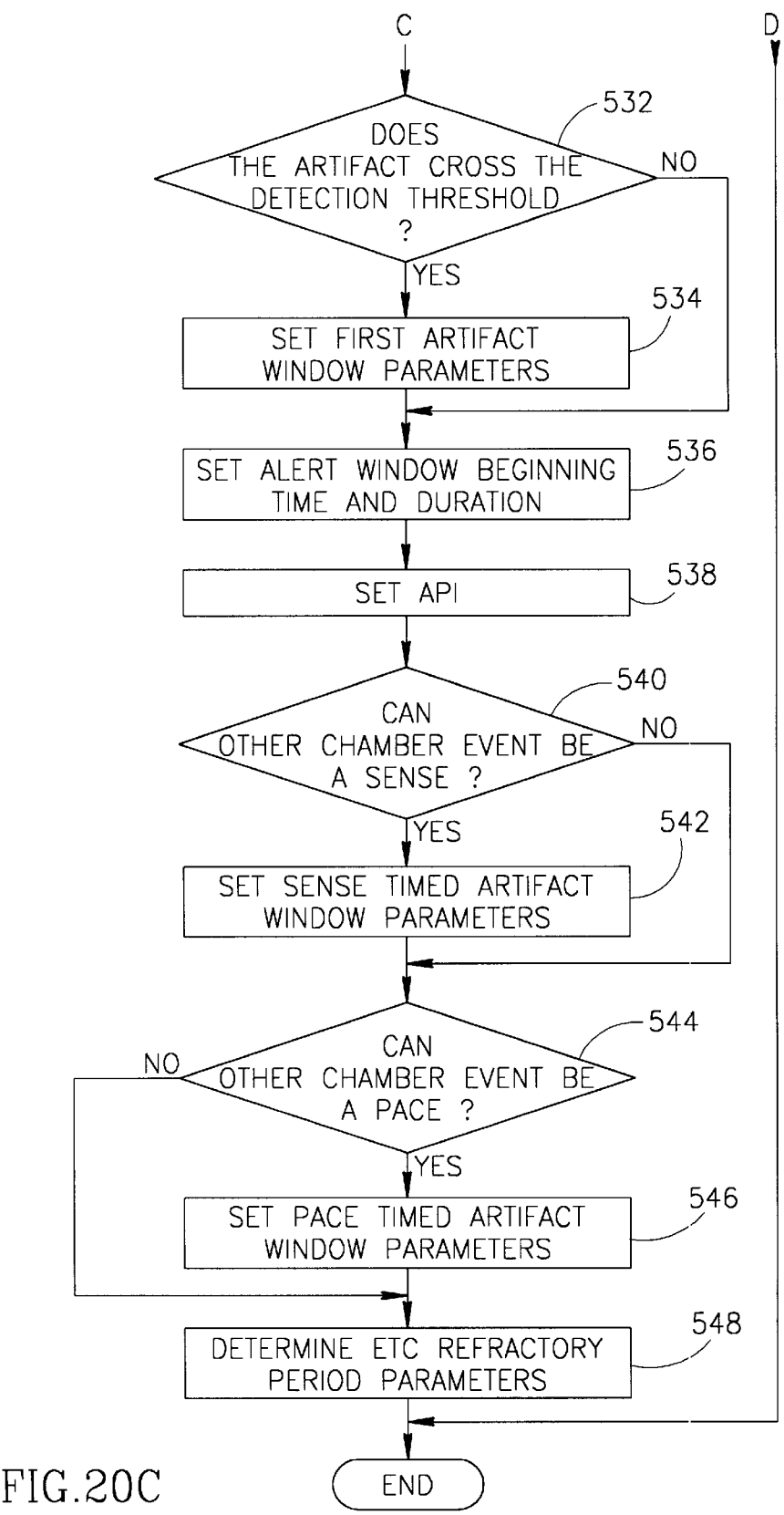

Reference is now made to FIGS. 20A–20C which are schematic flow diagrams illustrating the steps of the method for determining and setting the parameters of the various windows useful in the method of the present invention.

The method illustrated in FIGS. 20A–20C is a generalized method adapted for use in patients in which single or dual chamber pacing may be performed in addition to the delivery of ETC therapy to the heart.

The cardiologist or physician starts by selecting the pacing mode suitable for use in the patient (step 500). Any suitable pacing mode known in the art may be selected, depending, inter alia, on the pacing modes available in the device or the system which is being used. In a non-limiting example, a DDD pacing mode may be selected as is known in the art. The cardiologist then selects the trigger event (step 502). The selected trigger event may be a right atrial associated event (such as a right atrial sense or a right atrial pace), or a right ventricular associated event (such as a right ventricular sense or a right ventricular pace) as disclosed in detail hereinabove. After selecting the type of the trigger event, the cardiologist determines and sets the detection threshold which is to be used in detection of events in the LV locally sensed electrogram signal (step 504).

The cardiologist then checks whether the trigger may be a sense (step 506). The checking in step 506 determines whether the particular trigger event selected may possibly be a sense. This check is performed by the cardiologist based, inter alia, on the particular pacing mode selected, and on the particular pacing parameters as set by the cardiologist. For example, if the pacing mode selected is DDD mode and the trigger event is a right ventricle associated trigger event, the results of the check performed in step 506 may vary depending on the particular set of pacing parameters selected by the cardiologist. Under some pacing conditions such as, for example, pacing with a short A-V delay, the right ventricle will always be paced. In this case, the right ventricular trigger event can only be a pace event. However, when other different pacing parameters are used, it is possible that in some (or all) beat cycles, the trigger event will be a sense event since at least in some beat cycles the RV will not be paced. It is noted that, the above disclosed case is given by way of example only and other different examples are possible depending on the particular pacing mode and pacing parameters which were used for the patient and are determined by the cardiologist. However, the cardiologist makes the decision whether the trigger event may be a sense event, based on his or her knowledge of the pacing mode and the particular pacing parameters which the cardiologist selected for the patient.

If the cardiologist determines that based on the selected pacing mode and on the particular pacing parameters selected for use, the trigger event cannot be a sensed trigger, the cardiologist proceeds directly to perform step 528 as disclosed hereinbelow.

If the trigger event may be a sensed trigger event, the cardiologist determines and sets the ETC delay and the ETC duration (step 508). The determination of the ETC delay and ETC duration is based on the data collected in the test session from a plurality of cardiac beats in which the trigger event was a sensed trigger event. Thus, these values of the ETC delay and the ETC duration are based on the particular activation conduction velocity for sensed beats, and are stored for use only in cardiac beats in which the trigger events are sensed trigger events. The cardiologist then checks in the stored data of beats in which the trigger event was a sensed trigger event which were obtained in the test session whether one or more of the LV locally sensed far field artifact signals (FF artifact) crosses the detection threshold (step 510). If none of the LV locally sensed far field artifact signals crosses the detection threshold, the cardiologist proceeds to step 514.

If one or more of the LV locally sensed far field artifact signals (FF artifact) crosses the detection threshold, the cardiologist determines and sets the first artifact window parameters (step 512), sets the beginning time and the duration of the alert window (step 514), and sets the parameters of the artifact proximity interval (step 516) as disclosed hereinabove. Step 516 includes the selection and setting of an appropriate proximity interval initiating event as disclosed in detail hereinabove and the determination and setting of the duration of the API which is performed manually by the cardiologist based on the data collected from the patient in the test session for beats in which the trigger event was a sensed trigger event.

It is noted that the setting of the parameters of the artifact window performed in step 512 refers to the setting of the parameters of the artifact window 102 of FIGS. 9, 10A, 10B, 11, 12A, 12B, 13, 14 or of the artifact window 302 of FIG. 16. These parameters may include the beginning time and the duration of the first artifact windows 102 and 302. It is noted that, while preferably, the first artifact window 102 of FIG. 9 and the first artifact window 302 of FIG. 16 begin at the time of detection of the trigger event 102A and the trigger event 305, respectively, the artifact windows 102 and 302 may also be implemented as starting after the time of detection of the trigger events 102A and 305, respectively.

The cardiologist then checks whether the "other chamber" event may possibly be a sense (step 518). The term "other chamber" is used hereinafter to refer to a cardiac chamber other than the cardiac chamber with which the trigger event is associated.

For example, if the selected trigger event is a right atrial trigger event (such as an RA detected event or a pacing command or pacing signal for initiating pacing of the RA), the other chamber is the right ventricle. If the selected trigger event is a right ventricular trigger event (such as an RV detected event or a pacing command or pacing signal for initiating pacing of the RV), the other chamber is the right atrium.

The cardiologist determines whether the other chamber event may be a sense (i.e a sensed event) based on the pacing mode and the particular pacing parameters which the cardiologist has previously selected for the patient, as disclosed hereinabove. From the knowledge of the selected pacing mode and the selected pacing parameters the cardiologist may know whether it is possible that a sensed event will be recorded in the other chamber. If it is possible that a sensed event will occur in the other chamber, the cardiologist determines and sets the parameters of the second or third (sense timed) artifact window (step 520), and proceeds to step 522. The second or third artifact window may be the second artifact window 150 of FIG. 14 or the second artifact window 154 of FIG. 15 or the third artifact window 310 of FIG. 16. The setting of the second or third artifact window are based on data collected in the test session of cardiac beats in which the timing events, such as the timing events 205, 205A and 309, of FIGS. 14, 15 and 16, respectively, were sensed events. The cardiologist then proceeds to step 522.

If it is not possible that a sensed event will occur in the other chamber, the cardiologist checks whether the other chamber event may be a pace (step 522). The cardiologist determines whether the other chamber event may be a pace (i.e a paced event) based on the pacing mode and the particular pacing parameters which the cardiologist has previously selected for the patient, as disclosed hereinabove. From the knowledge of the selected pacing mode and the selected pacing parameters the cardiologist may know whether it is possible that a paced event will be recorded in the other chamber. If it is possible that a paced event will occur in the other chamber, the cardiologist determines and sets the parameters of the pace timed second or third artifact window (step 524), and proceeds to step 526. The second or third artifact window may be the second artifact window 150 of FIG. 14 or the second artifact window 154 of FIG. 15 or the third artifact window 310 of FIG. 16. The setting of the second or third artifact window are based on data collected in the test session of cardiac beats in which the timing events, such as the timing events 205, 205A and 309, of FIGS. 14, 15 and 16, respectively, were paced events or pace associated events such as a logical pacing command or the like, as disclosed in detail hereinabove.

If it is not possible that a paced event will occur in the other chamber, the cardiologist proceeds directly to step 526.

In step 526, the cardiologist determines the parameters of the refractory period, such as the refractory period 128 of FIGS. 9, 12A, 14 and 15, based, inter alia, on the particular parameters of the ETC induced artifact signal, the selected value of the threshold for event detection or the particular detection method which is used for event detection as disclosed in detail hereinabove. It is noted that, preferably, the beginning time and the duration of the refractory period determined in step 526 are parameters which are to be used only for cardiac beat cycles for which the trigger event was a sense (due to the possible difference in the timing parameters of the ETC signal of paced and sensed cardiac beats). However, it is noted that in certain patients, it is possible that the duration of the refractory period 128 may be identical in value for beats with sensed and paced trigger events.

In step 528 the cardiologist checks whether the trigger event may be a pace (i.e whether the trigger event may be a paced event or an event associated with pacing such as, but not limited to a logical pacing command, as disclosed hereinabove).

If the cardiologist determines that the trigger event may be a pace or a pace associated event, the cardiologist determines and sets the ETC delay and duration (step 530). The determination of the ETC delay and ETC duration is based on the data collected in the test session from a plurality of cardiac beats in which the trigger event was a paced trigger event. Thus, these values of the ETC delay and the ETC duration are based on the particular activation conduction velocity for paced beats, and are stored for use only in cardiac beats in which the trigger events are paced trigger events.

The cardiologist then checks in the stored data of beats in which the trigger event was a paced trigger event which were obtained in the test session whether one or more of the LV locally sensed far field artifact signals (FF artifact) crosses the detection threshold (step 532). If none of the LV locally sensed far field artifact signals crosses the detection threshold, the cardiologist proceeds to step 536.

If one or more of the LV locally sensed far field artifact signals (FF artifact) crosses the detection threshold, the cardiologist determines and sets the first artifact window parameters including the beginning time and the duration of the first artifact window (step 534), sets the beginning time and the duration of the alert window (step 536), and sets the parameters of the artifact proximity interval (step 538) as disclosed hereinabove. Step 538 includes the selection and setting of an appropriate proximity interval initiating event as disclosed in detail hereinabove and the determination and setting of the duration of the API which is performed manually by the cardiologist based on the data collected from the patient in the test session for beats in which the trigger event was a paced trigger event.

It is noted that the setting of the duration of the artifact window performed in step 512 refers to the setting of the duration of the artifact window 102 of FIGS. 9, 10A, 10B, 11, 12A, 12B, 13, 14 or of the artifact window 302 of FIG. 16.

The cardiologist then checks whether the "other chamber" event may possibly be a sense (step 540). The term "other chamber" is used hereinafter to refer to a cardiac chamber other than the cardiac chamber with which the trigger event is associated (as is disclosed hereinabove in step 518).

The cardiologist determines whether the other chamber event may be a sense (i.e a sensed event) based on the pacing mode and the particular pacing parameters which the cardiologist has previously selected for the patient, as disclosed hereinabove. From the knowledge of the selected pacing mode and the selected pacing parameters the cardiologist may know whether it is possible that a sensed event will be recorded in the other chamber. If it is possible that a sensed event will occur in the other chamber, the cardiologist determines and sets the parameters of the sense timed second or third artifact window (step 542). The second or third artifact window may be the second artifact window 150 of FIG. 14 or the second artifact window 154 of FIG. 15 or the third artifact window 310 of FIG. 16. The setting of the second or third artifact window are based on data collected in the test session of cardiac beats in which the timing events, such as the timing events 205, 205A and 309, of FIGS. 14, 15 and 16, respectively, were sensed events. The cardiologist then proceeds to step 522.

If it is not possible that a sensed event will occur in the other chamber, the cardiologist checks whether the other chamber event may be a pace (step 544). The cardiologist determines whether the other chamber event may be a pace (i.e. a paced event) based on the pacing mode and the particular pacing parameters which the cardiologist has previously selected for the patient, as disclosed hereinabove. From the knowledge of the selected pacing mode and the selected pacing parameters the cardiologist may know whether it is possible that a paced event will be recorded in the other chamber. If it is possible that a paced event will occur in the other chamber, the cardiologist determines and sets the parameters of the pace timed second or third artifact window (step 546) and proceeds to step 548. The second or third artifact window may be the second artifact window 150 of FIG. 14 or the second artifact window 154 of FIG. 15 or the third artifact window 310 of FIG. 16. The setting of the second or third artifact window are based on data collected in the test session of cardiac beats in which the timing events, such as the timing events 205, 205A and 309, of FIGS. 14, 15 and 16, respectively, were paced events or pace associated events such as a logical pacing command or the like, as disclosed in detail hereinabove.

If it is not possible that a paced event will occur in the other chamber, the cardiologist proceeds directly to step 548.

In step 548, the cardiologist determines the parameters of the refractory period, such as the refractory period 128 of FIGS. 9, 12A, 14 and 15, based, inter alia, on the particular parameters of the ETC induced artifact signal, the selected value of the threshold for event detection or the particular detection method which is used for event detection as disclosed in detail hereinabove. It is noted that preferably, the parameters of the refractory period including the delay between the detection of the first valid event within the alert window and the beginning time of the refractory period (which may be also and the duration of the refractory period which are determined in step 548 are parameters which are to be used only for cardiac beat cycles for which the trigger event was a pace (due to the possible difference in the timing parameters of the ETC signal of paced and sensed cardiac beats). However, it is noted that in certain patients, it is possible that the duration of the refractory period 128 may be identical in value for beats with sensed and paced trigger events.

If the cardiologist determines (in step 528) that the trigger event may not be a paced trigger event, the cardiologist ends the procedure.

It is noted that the above disclosed method for determining the various parameters of the various time windows such as the artifact windows, refractory period, and ETC signal parameters is intended to provide one non-limiting example of the various steps performed by the cardiologist based on the results of the records collected during the test session. However, different modifications of the order of the steps and of the exact way the various parameters are determined, set and/or computed are possible in ways which are included within the scope of the present invention. For example, steps 522 and 524 may be performed prior to steps 518 and 520 (FIG. 18B). Similarly steps 544 and 546 may be performed prior to steps 540 and 542 (FIG. 18B).

While not specifically included in the above steps of the method, any of the steps in which a parameter is determined and/or set may also include other computational steps. For example, in according with on preferred embodiment of the present invention in steps 520 and 524 of FIG. 20B, the setting of the sense timed and pace timed artifact window parameters, respectively may also include the steps of computing the corresponding sets of reconstruction parameters as is disclosed in detail hereinabove. Similarly, in steps 542 and 546 of FIG. 20C, the setting of the sense timed and pace timed artifact window parameters, respectively may also include the steps of computing the corresponding sets of reconstruction parameters as is disclosed in detail hereinabove.

Additionally, the step or steps of setting of any of the above parameters determined by the cardiologist may include the steps of communicating the determined values or the computed values (such as the various computed reconstruction parameter sets for the paced and sensed of beats) to the device or the system which is used to time the delivery of ETC signals to the heart as disclosed hereinabove, such as but not limited to the device 21 of FIG. 3 and the system 60 of FIG. 5. The communicating of the various parameters needed for performing the ETC timing in accordance with the present invention may be performed telemetrically or non-telemetrically depending on the type of the system or the device used in the patient, by using any suitable method of data communication which is known in the art.

After the determination and setting of the various parameters as disclosed hereinabove, and the downloading the various parameters which were determined and set into the device or the system of the present invention, the device (such as but not limited to the device 21 of FIG. 3) or the system (such as but not limited to the system 60 of FIG. 5) may be operated to control the delivery of ETC signals to the heart as disclosed in detail hereinabove and illustrated in FIGS. 9–16.

At the end of the procedure disclosed hereinabove and illustrated in FIGS. 20A–20C, the parameter sets stored in the device or the system may include two different ETC parameter sets including a first ETC parameter set comprising the ETC delay 122 and the duration of the ETC signal 106 as set by the cardiologist in step 508 of FIG. 20A for beats in which the trigger event is a sense, and a second ETC parameter set comprising the ETC delay 122 and the duration of the ETC signal 106 as set by the cardiologist in step 530 of FIG. 20B for beats in which the trigger event is a pace or a pacing related event. However, if due to the pacing mode and the pacing parameters selected by the cardiologist, only one type of beats may occur in the patient (either paced or sensed beats), only the relevant single set of ETC parameters which was determined during the procedure illustrated in FIGS. 20A–20C is stored in the device or the system.

Similarly, at the end of the procedure disclosed hereinabove and illustrated in FIGS. 20A–20C, the parameter sets stored in the device or the system may include two different parameter sets for the first artifact window 102 (or for the first artifact window 302) including a first parameter set comprising the beginning time and the duration of the first artifact window as set by the cardiologist in step 512 of FIG. 20A for beats in which the trigger event is a sense, and a second parameter set comprising the beginning time and the duration of the first artifact window as set by the cardiologist in step 534 of FIG. 20C for beats in which the trigger event is a pace or a pacing related event. However, if due to the pacing mode and the pacing parameters selected by the cardiologist, only one type of beats may occur in the patient (either paced or sensed beats), only the relevant single set of parameters of the first artifact window which was determined during the procedure illustrated in FIGS. 20A–20C is stored in the device or the system.

Furthermore, at the end of the procedure disclosed hereinabove and illustrated in FIGS. 20A–20C, the parameter sets stored in the device or the system may include two different parameter sets for the alert window 104 (or for the alert window 194 or 304 if relevant) including a first parameter set comprising the beginning time and the duration of the alert window as set by the cardiologist in step 514 of FIG. 20A for beats in which the trigger event is a sense, and a second parameter set comprising the beginning time and the duration of the alert window as set by the cardiologist in step 536 of FIG. 20C for beats in which the trigger event is a pace or a pacing related event. However, if due to the pacing mode and the pacing parameters selected by the cardiologist, only one type of beats may occur in the patient (either paced or sensed beats), only the relevant single set of parameters of the alert window which was determined during the procedure illustrated in FIGS. 20A–20C is stored in the device or the system.

Furthermore, at the end of the procedure disclosed hereinabove and illustrated in FIGS. 20A–20C, the parameter sets stored in the device or the system may include two different values for the duration of the API 124 including a first value comprising the duration of the API 124 as set by the cardiologist in step 516 of FIG. 20A for beats in which the trigger event is a sense, and a second value of the duration of the API 124 as set by the cardiologist in step 538 of FIG. 20C for beats in which the trigger event is a pace or a pacing related event. However, if due to the pacing mode and the pacing parameters selected by the cardiologist, only one type of beats may occur in the patient (either paced or sensed beats), only the relevant single value of the duration of the API 124 which was determined during the procedure illustrated in FIGS. 20A–20C is stored in the device or the system.

Further yet, at the end of the procedure disclosed hereinabove and illustrated in FIGS. 20A–20C, the parameter sets stored in the device or the system may include two different parameter sets for the refractory period 128 (or for the refractory period 328 if relevant) including a first parameter set comprising the duration of the second delay period disclosed hereinabove (not shown) and the duration of the refractory period 128 (or 328 if relevant) as set by the cardiologist in step 526 of FIG. 20B for beats in which the trigger event is a sense, and a second parameter set comprising the duration of the second delay period disclosed hereinabove (not shown) and the duration of the refractory period 128 (or 328 if relevant) as set by the cardiologist in step 548 of FIG. 20C for beats in which the trigger event is a pace or a pacing related event. However, if due to the pacing mode and the pacing parameters selected by the cardiologist, only one type of beats may occur in the patient (either paced or sensed beats), only the relevant single set of parameters of the refractory period 128 (or 328 if relevant) which was determined during the procedure illustrated in FIGS. 20A–20C is stored in the device or the system. It will therefore be appreciated by those skilled in the art that, if due to the pacing mode and the pacing parameters selected by the cardiologist, only one type of beats may occur in the patient (either paced or sensed beats), only the relevant single set of parameters of the refractory period 128 (or 328 if relevant) which was determined during the procedure illustrated in FIGS. 20A–20C is stored in the device or the system.

Similarly, at the end of the procedure disclosed hereinabove and illustrated in FIGS. 20A–20C, the parameter sets stored in the device or the system may include up to four different parameters sets for computing on the fly the beginning and ending time of the second artifact window 150 (or of the second artifact window 154 if relevant). For example, each set of parameters may include the two reconstruction parameters disclosed hereinabove for computing the beginning and the ending time of the second artifact window 150 or 154 based on the timing event 205 of FIG. 14 (or on the timing event 205A of FIG. 15, if relevant). The stored different parameter sets are as possibly set by the cardiologist in steps 520, 524 of FIG. 20B and in steps 542 and 546 of FIG. 20C. The exact number of the stored parameter sets for a particular patient depends, inter alia, on the configuration of the sensing and pacing electrodes in the different cardiac chambers, on the pacing mode being used and the particular pacing parameters which are set by the cardiologist, and on the type of trigger event selected by the cardiologist.

In a patient in which dual chamber pacing may be performed and in which the trigger event is a right ventricular associated trigger event, the parameter sets stored in the device or the system may include up to four different parameter sets for computing on the fly the beginning and ending time of the third artifact window 310 (see FIG. 16). For example, each set of parameters may include the two reconstruction parameters disclosed hereinabove for computing the beginning and the ending time of the third artifact window 310 based on the timing event 309 of FIG. 16. In accordance with one specific non-limiting example, the stored different parameter sets for determining the timing of the third artifact window 310 are as possibly set by the cardiologist in steps 520, 524 of FIG. 20B and in steps 542 and 546 of FIG. 20C. The exact number of the stored parameter sets for a particular patient depends, inter alia, on the pacing mode being used and the particular pacing parameters which are set by the cardiologist.

Thus, for example, in a patient in which the LV is locally sensed and in which dual chamber pacing is used with pacing parameters set such that the right atrium and the right ventricle are always paced, and in which the trigger event is the right atrial pacing command and an API is being used (API not shown), the parameter sets stored in the device or the system further include one set of ETC signal parameters (including ETC delay and ETC duration) which was determined and set in step 530 of FIG. 20B, one set of parameters for the alert window 304 which are determined and set in step 534 of FIG. 20C, one value of the duration of the artifact proximity interval (API) which was determined and set in step 538 of FIG. 20C, one set of parameters for the third (pace timed) artifact window 310 which was determined in step 544 of FIG. 20C and one set of parameters for the refractory period 328 which was determined and stored in the device or the system in step 548 of FIG. 20C.

The type and number of the parameter sets stored in the system or the device of the present invention, thus varies from patient to patient depending on, inter alia, the specific electrode configuration used in the patient, the type of pacing mode used, and the exact setting of the pacing parameters selected by the cardiologist.

In operation, the device or the system is operative to perform the sensing and pacing of the selected cardiac chambers as is known in the art, in accordance with the specific pacing mode and pacing parameters as selected by the cardiologist. When ETC therapy is required, the controlling of the delivery of ETC signals is performed as disclosed in detail hereinabove. The device or system uses the trigger event selected by the cardiologist. The detection of events in the LV locally sensed electrogram signal is performed using the particular event detection method which is implemented on the device or the system, such as but not limited to a single threshold detection method, a morphological detection method or the like. The device or system stores the time of detection of detected events within the beat cycle.

During the operation of the ETC device or the ETC system, the device or the system selects the appropriate sets of parameters for computing or determining the timing parameters of the various time periods disclosed hereinabove, from the plurality of parameter sets which were set by the cardiologist using the method illustrated in FIGS. 20A–20C and stored in the memory of the device or the system (such as, but not limited to the memory unit 44. of FIGS. 3 and 4 or the memory unit 66 of FIGS. 5 and 6). The selecting of the parameter sets is base upon the data available to the device or the system about the type (paced or sensed) of the current beat. For example, if the two parameter sets for determining the ETC signal parameters which are stored in the device include a first parameter set determined for paced beats and a second parameter set determined for sensed beats, the selection of the appropriate parameter set is based on the beat type information available to the device within the current beat cycle. In accordance with one specific non-limiting example, if the selected trigger event is a right atrial trigger event and if the device or the system detects a right atrial pacing command (initiated by the controller unit 40 or by the pacing core 34 of FIG. 3 or by the processor unit 61 or the pacing unit 68 of FIG. 5), the device or the system automatically selects the first parameter set determined for paced beats for computing therefrom the parameters of the ETC signal. If the device or the system detects a right atrial sensed event (RA sense), the device or the system selects the second parameter set determined for sensed beats for computing therefrom the parameters of the ETC signal.

Similarly, in accordance with another specific non-limiting example, if the selected trigger event is a right atrial trigger event, four parameter sets for determining the parameters of the second artifact window may be stored in the device or the system. The four parameter sets include a first parameter set determined for beats in which the RA was sensed and the RV was sensed, a second parameter set determined for beats in which the RA was sensed and the RV was paced, a third parameter set determined for beats in which the RA was paced and the RV was sensed and a fourth parameter set determined for beats in which the RA was paced and the RV was paced. In this case the selection of the appropriate parameter set out of the four stored parameter sets is based on the beat type information available to the device within the current beat cycle. In accordance with the specific non-limiting example above, if the device or the system detects an RA sense followed by an RV sense, the device or the system automatically selects the first parameter set for implementing the second artifact window. If the device or the system detects a right atrial sensed event (RA sense) followed by a RV pace (such as but not limited to an RV pacing command initiated by the controller unit 40 or by the pacing core 34 of FIG. 3 or by the processor unit 61 or the pacing unit 68 of FIG. 5), the device or the system automatically selects the second parameter set for implementing the second artifact window. If the device or the system detects a right atrial pace (such as but not limited to an RA pacing command initiated by the controller unit 40 or by the pacing core 34 of FIG. 3 or by the processor unit 61 or the pacing unit 68 of FIG. 5) followed by a RV sense, the device or the system automatically selects the third parameter set for implementing the second artifact window. Finally, if the device or the system detects a right atrial pace (such as but not limited to an RA pacing command initiated by the controller unit 40 or by the pacing core 34 of FIG. 3 or by the processor unit 61 or the pacing unit 68 of FIG. 5) followed by a RV pace (such as but not limited to an RV pacing command initiated by the controller unit 40 or by the pacing core 34 of FIG. 3 or by the processor unit 61 or the pacing unit 68 of FIG. 5), the device or the system automatically selects the third parameter set for implementing the second artifact window.

Thus, the selection of the appropriate parameter sets from the plurality of parameter sets which are stored in the device or the system, is automatically performed on-line for each beat cycle and is based upon on-line determination of the type of the beat based on the information available to the device or the system, indicating whether the RA was paced or sensed and whether the RV was sensed or paced within each individual beat cycle.

The device or the system computes the beginning time and the ending time of the alert window relative to the trigger event from the automatically selected alert window parameter set as disclosed hereinabove.

The device or the system computes on the fly the parameters of the various time periods such as the starting and the ending time of the API 124 (if relevant). Depending on the automatically selected artifact window parameter sets, the device or the system also computes on the fly the parameters of the relevant artifact windows based on the time of occurrence of the corresponding timing event and on the particular values of the reconstruction parameters included in the automatically selected parameter sets. This computation is performed only after the time of occurrence of the timing event. For example, the beginning time and ending time of the second artifact window 150 are computed on the fly after the time of occurrence of the timing event 205. In another example, the beginning time and ending time of the second artifact window 154 are computed on the fly after the time of occurrence of the timing event 205A. In another example, the beginning time 310A and ending time 310B of the second artifact window 310 are computed on the fly after the time of occurrence of the timing event 309.

If an API is used, the system automatically selects the appropriate API duration value from the stored values of the duration of the API based on the pacing and/or sensing information available for the beat as disclosed hereinabove The device or the system detect the events which occur within the duration of the first artifact window (such as but not limited to the first artifact window 102 of FIG. 9A) as disclosed hereinabove and illustrated in FIGS. 9A–9B, and 10A–10C. If no API is used the device or the system ignores all the events which are detected within the duration of the first artifact window. If an API such as, but not limited to the API 124 is being used as disclosed hereinabove the device or the system determines the beginning time of the API in accordance with the type of proximity interval initiating event which was defined and set by the cardiologist. For example, if the cardiologist has set the proximity interval initiating event as the first event detected within the first artifact window, the device or the system starts the API at the time of detection of the first event occurring within the duration of the first artifact. In accordance with another non-limiting example, if the cardiologist has set the proximity interval initiating event as the last event detected within the first artifact window, the device or the system starts the API at the time of detection of the last event occurring within the duration of the first artifact. However, the other types of definitions of the proximity interval initiating event which are disclosed hereinabove may also be used by the system or the device.

Any event which is detected within a part of the API which does not overlap the first artifact window 102 is defined as an "inhibiting event". Furthermore, any event which is detected within the duration of the time interval beginning after the end of the first artifact window 102 and ending at the beginning of the alert window 104 of FIGS. 9A–9B and 10A–10C, is also defined by the device or the system as an inhibiting event (irrespective of whether the same event also occurs within the duration of the API 124 or not) and causes the system or the device to inhibit the delivery of an ETC signal within the current beat cycle (even if an event is detected within the duration of the alert window).

In cases in which a second artifact window is implemented, any event which is detected within the duration of the second artifact window, is ignored by the device or the system as an expected artifact signal and does not cause inhibiting of ETC signal delivery. Preferably, the second artifact window 150 of FIG. 14 is a relatively short time interval having a duration of approximately 5 milliseconds. However, other larger or smaller duration values of the second artifact window 140 (FIG. 14) may be implemented, depending, inter alia, on the duration of the electrical artifact signal 182 which may be a pacing artifact or a far field sensed artifact as disclosed in detail hereinabove. Thus, all the events which are detected within the duration of the second artifact window 150 are ignored by the device or the system.

If a single event is detected within the duration of the alert window and if this event does not occur within the duration of the computed API, the device or the system conditionally enables the delivery of an ETC signal to the heart, and computes and stores the time and duration for delivering the ETC signal to the heart and the appropriate refractory period which is to be used, as disclosed in detail hereinabove. However, if two or more events are detected within the duration of the alert window, the device or the system inhibits the delivery of ETC signal to the heart.

Any additional event detected within the duration of the alert window after the time of detection of the first event which is detected within the duration of the same alert window, is also referred to as an "inhibiting event" and inhibits the delivery of the ETC signal, except in the case (see FIG. 15) that an event is detected within the time interval of overlap between the second artifact window 154 and the alert window 194 of FIG. 15. In this case the event happening in the time interval of overlap is ignored since it is assumed that it is an expected artifact and the method does not inhibit the delivery of an ETC signal within the current beat cycle which may be enabled by a second event detected within the duration of the alert window 106 in the portion thereof which does not overlap with the second artifact window 154 (FIG. 15). This second event may have the exemplary timing illustrated by the event 282 of FIG. 15, but may happen at any other time within the portion of the alert window which does not overlap with the second artifact window 154.

Another possible type of an inhibiting event which will inhibit the delivery of an ETC signal to the heart is an event which is detected within the time interval starting after the end of the alert window and ending at the computed time of the beginning of the refractory period. The detection of such an event will result in inhibiting the delivery of the ETC signal within the current beat cycle.

If only one event was detected within the duration of the alert window and none of the above described inhibiting events has occurred, the device or the system initiates the refractory period according to the parameter set automatically selected from the refractory period parameter sets stored in the device or the system as disclosed hereinabove and delivers the scheduled ETC signal to the heart at the end of the ETC delay period (such as the delay period 122 of FIGS. 9A, 9B, 10C, 12A, 14 and 15 or the delay period 322 of FIG. 16).

After the refractory period 128 of FIGS. 9, 12A, 14 and 15 or the refractory 128A of FIG. 10C is ended, the device or the system continues the sensing and detecting of events within the sensing period 130 (FIGS. 9, 12A, 14 and 15) or within the sensing period 130A of FIG. 10C, respectively. If an event is detected within the sensing period 130 (FIGS. 9, 12A, 14 and 15), or within the sensing period 130A of FIG. 10C, respectively, the delivery of an ETC signal within the next cardiac beat cycle following the current beat cycle is inhibited as disclosed in detail hereinabove.

Additionally, as disclosed in detail hereinabove and illustrated in FIG. 16, if one or more events are detected within the duration of the third artifact window 310 (FIG. 16), all the events which are detected within the duration of the third artifact window 310 are ignored since they are assumed to occur due to an expected artifact signal (such as, for example the artifact signal 340 of FIG. 16), and the ETC delivery in the next beat cycle is therefore not inhibited by the system or the device. However, if any event is detected within the duration of the portions of the sensing period 330 which do not overlap the third artifact window 310, the system or the device inhibit the delivery of an ETC signal in the next cardiac beat cycle.

The exact details of storing the plurality of parameter sets and values in the device or the system and of selecting the appropriate values and parameter sets from the stored plurality of parameter sets and values are well known in the art, are not the subject matter of the present invention and are therefore only briefly described. For example, the parameter sets and the values may be stored in a suitable array or look up table (LUT) in the memory unit 66 or 44. Each set of parameters or each value such as the values of the duration of the API, may be associated with a specific identifying set of cardiac conditions. This association may be performed by using specific array or LUT storage positions or by any other suitable method known in the art such as but not limited to associating each parameter set with a unique identifier stored in the array or LUT. Generally, any suitable method known in the art for storing the above disclosed parameter sets and the above disclosed values and for retrieving selected sets of parameters based on the beat type information available within the current beat cycle, may be used to implement the method of the present invention.

It will be appreciated by those skilled in the art that the method of controlling the delivery of cardiac contractility modulating signals of the present invention disclosed hereinabove may be implemented in many different ways as a control software program operative on the controller unit 40 of FIGS. 34 or on the processing unit 61 of FIGS. 5–6. Such a software control program may implemented in many different implementations known in the art which are included within the scope and spirit of the present invention. The software program is operative to compute the various time intervals within the current beat cycle as disclosed in detail hereinabove, to determine the time of detection of events within the current beat cycle and to classify certain events as inhibitory events in accordance with the criteria disclosed in detail hereinabove. It is noted that the computation of some of the parameters of some of the time intervals by the program may depend on the availability of certain data to the program. For example, the beginning and the ending time of the API 124 within the current beat cycle may be computed only after the detection of the event defined and set by the cardiologist as the proximity interval initiating event as disclosed hereinabove. In another example, the beginning and ending times of the second artifact window 150 may be computed only after the timing event 205 was detected by the program. However, this does not create a problem, since the program need not necessarily determine whether a detected event is an inhibitory event or not immediately upon the detection of the event. Rather, the program may detect and store the times of detection of events within the current beat cycle and defer the step of checking whether any of the detected events is an inhibiting event till a time at which all the necessary parameters of the relevant intervals and windows have been computed. Similarly, the program may defer the decision of whether a certain event detected after the end of the refractory period 128 (or 128A) is or is not an event which will inhibit the delivery of an ETC signal to the heart in the next beat cycle till a time at which the beginning and ending time of the third artifact window 310 has been computed.

It is noted that, while preferably most of the steps of the above method for controlling the delivery of ETC signals are performed digitally by a program or programs operative on the controller unit 44 or the processing unit 61, some of the steps may be implemented by using analog circuits. For example, the detection of the events within the locally sensed LV electrogram signal may be digitally performed on the digitized electrogram signal but may also be implemented by an analog detector unit (not shown). Such use of analog circuits for implementing steps of the method disclosed hereinabove are considered to be within the scope of the present invention.

It is further noted that the ETC or CCM devices disclosed hereinabove may also be modified to include the appropriate electrical circuitry for delivering electrical defibrillating signals to the heart. For example the implantable devices 1, 21 and 24 disclosed hereinabove may also include integrated defibrillator units (not shown) and the programs embedded within the controller unit 40 may be adapted to control the delivery of cardioverting and/or defibrillating signals to the heart as is known in the art. For example, U.S. Pat. No. 4,830,006 to Haluska titled "IMPLANTABLE CARDIAC STIMULATOR FOR DETECTION AND TREATMENT OF ARRYTHMIAS" discloses a device for performing pacing-type therapies and cardioversion and defibrillation shock-type therapies. The implantable devices 1, 21 and 24 may be adapted for performing such pacing-type therapies and cardioversion and defibrillation shock-type therapies.

It will be appreciated by those skilled in the art that, while the examples of the invention disclosed and illustrated hereinabove are adapted for delivering the ETC signal to the LV based on local sensing in the LV and on using a trigger signal associated with the RA or with the RV, other configurations of the methods and devices may be used which are within the scope of the present invention. For example, since the activation of the left atrium (LA) normally occurs close to the time of activation of the RA, the invention may also be adapted such that the trigger event is an event associated with activation of the left atrium. For example, the trigger event may be the sensing of left atrial activation by a suitable sensing electrode disposed at or about the LA (not shown). Alternatively, the trigger event may be an LA pacing related event, such as but not limited to a LA pacing command or the like. Additionally, the method may be adapted for timing the delivery of an ETC signal to any other chamber of the heart besides the left ventricle, such as the right ventricle, the right atrium and the left atrium. In such cases, with or without pacing of one or more cardiac chambers, the use and/or the positions of the various artifact windows within the cardiac beat cycle may have to be modified in accordance with, inter alia, the types of windows used and the source of the trigger event and the timing events which are being used. Such modifications may be made by the person skilled in the art based on the details and general principles of the method disclosed hereinabove and illustrated in the drawing figures, and are therefore included within the scope and spirit of the present invention.

It is further noted that, in all the embodiments of the devices disclosed hereinabove and illustrated in the drawings, the electrical power sources of the devices are not shown for the sake of clarity of illustration. Such power sources, for example, batteries and/or line operated power supplies or the like, may be internal power sources included in the implantable devices 21, 24 or external power sources of the devices 64 and 74. Such power sources used to provide power to the electronic circuitry of these devices, are not the subject matter of the present invention, are well known in the art and are therefore not disclosed in detail herein.

While the invention has been described with respect to a limited number of embodiments, it will be appreciated by those skilled in the art that many variations, modifications and other applications of the invention may be made.

What is claimed is:

1. A method for controlling the delivery of a non-excitatory cardiac contractility modulating signals to a heart within a cardiac beat cycle, the method comprising the steps of:

sensing electrical activity in or about a first cardiac chamber to provide a first electrogram signal;

detecting electrical events in said first electrogram signal;

providing a first artifact window within the current beat cycle, said first artifact window starts at or after a trigger event representing the beginning of said current cardiac beat cycle, said first artifact window has a first artifact window duration, and detecting events occurring in said first electrogram signal within the duration of said first artifact window;

providing an alert window period within said current beat cycle, said alert window period has a first duration and is delayed from said trigger event;

enabling the delivery of a cardiac contractility modulating signal to said first chamber of said heart within said current beat cycle in response to a first event detected in said first electrogram signal within the duration of said alert window period, said delivery of said cardiac contractility modulating signal is delayed from the time of detecting of said first event occurring within the duration of said alert window period by a first delay period, said cardiac contractility modulating signal has a cardiac contractility modulating signal duration;

providing a refractory period within said current beat cycle, in response to said first event of said step of enabling, said refractory period has a refractory period duration, a beginning time and an ending time, said beginning time is delayed from said first event of said step of enabling by a second delay period, said ending time occurs at or after the termination of said cardiac contractility modulating signal, for preventing the detection of electrical events within the duration of said refractory period;

applying said cardiac contractility modulating signal to said heart within said current beat cycle; and inhibiting the performing of said step of providing a refractory period and of said step of applying said cardiac contractility modulating signal, in response to detecting at least one inhibiting event within said first electrogram signal.

2. The method according to claim 1 wherein said first cardiac chamber is the left ventricle of said heart.

3. The method according to claim 1 wherein said first cardiac chamber is the right ventricle of said heart.

4. The method according to claim 1 wherein said trigger event is an event associated with electrical activation of the right ventricle of said heart.

5. The method according to claim 4 wherein said trigger event is a right ventricular event detected by a sensing electrode electrically coupled to the right ventricle of said heart.

6. The method according to claim 4 wherein said trigger event is a right ventricular pacing command or an event synchronized therewith.

7. The method according to claim 1 wherein said trigger event is an event associated with electrical activation of the right atrium of said heart.

8. The method according to claim 7 wherein said trigger event is a right atrial event detected by a sensing electrode electrically coupled to the right atrium of said heart.

9. The method according to claim 7 wherein said trigger event is a right atrial pacing command or an event synchronized therewith.

10. The method according to claim 1 wherein said preventing of said step of providing a refractory period comprises the step of stopping the sensing of said first electrogram signal within the duration of said refractory period.

11. The method according to claim 1 wherein said preventing of said step of providing a refractory period comprises the step of stopping the detecting of said electrical events in said first electrogram signal within the duration of said refractory period.

12. The method according to claim 1 wherein said step of detecting comprises detecting electrical events based on a single threshold crossing criterion of said first electrogram signal.

13. The method according to claim 1 wherein said step of detecting comprises detecting electrical events using a detection method based on one or more detection criteria selected from, the crossing of at least one threshold by said first electrogram signal, a slope criterion, a criterion based on one or more morphological parameters of said first electrogram signal and any combination thereof.

14. The method according to claim 1 wherein said alert window period starts immediately after the first artifact window ends.

15. The method according to claim 1 wherein said first delay period is equal to said second delay period.

16. The method according to claim 1 wherein said first delay period is larger than said second delay period.

17. The method according to claim 1 wherein said at least one inhibitory event comprises a single event or any combination of events selected from the group of events consisting of, an event detected in said first electrogram signal within the time interval between the ending time of said first artifact window and the starting time of said alert window period, an event detected in said first electrogram signal within the duration of said alert window period after the time of detection of said first event of said step of enabling, and an event detected within the time interval starting after the end of said alert window and ending at said beginning time of said refractory period.

18. The method according to claim 1 further including the step of inhibiting the delivery of a cardiac contractility modulating signal to said heart within the next beat cycle following said current beat cycle, in response to detecting in said first electrogram signal an event within the duration of a sensing time period starting after the end of said refractory period and ending at the end of said current beat cycle.

19. The method according to claim 1, wherein the delivery of a cardiac contractility modulating signal to the heart within said current beat cycle was inhibited in said step of inhibiting due to an event detected in said first electrogram signal within the time interval between the ending time of said first artifact window and the starting time of said alert window period, or due to an event detected in said first electrogram signal within the duration of said alert window period after the time of detection of said first event of said step of enabling, wherein the method further includes the step of inhibiting the delivery of an cardiac contractility modulating signal to said heart within the next beat cycle following said current beat cycle, in response to detecting in said first electrogram signal an event within the duration of a time period starting after the end of said alert window and ending at the end of said first delay period.

20. The method according to claim 1 wherein said step of providing a first artifact window comprises the steps of:
   if said trigger event is a sensed event associated with intrinsic activation of a second cardiac chamber, automatically selecting a first artifact window parameter set associated with said first artifact window;
   if said trigger event is an event associated with pacing of said second cardiac chamber, automatically selecting a second parameter set associated with said first artifact window; and
   determining the beginning time and the ending time of said first artifact window relative to said trigger event from the automatically selected parameter set.

21. The method according to claim 20 wherein said second cardiac chamber is the right atrium of said heart, said first parameter set is determined based on data obtained from cardiac beats of said heart in which said trigger event is a right atrial sensed event associated with intrinsic activation of said right atrium, said second parameter set is determined based on data obtained from cardiac beats of said heart in which said trigger event is an event associated with pacing of said right atrium, and each of said first parameter set and said second parameter set includes a first parameter representing the delay between said trigger event and said beginning time of said first artifact window and a second parameter representing the duration of said first artifact window.

22. The method according to claim 20 wherein said second cardiac chamber is the right ventricle of said heart, and wherein said first parameter set is determined based on data obtained from cardiac beats of said heart in which said trigger event is a sensed event associated with intrinsic activation of said right ventricle, and wherein said second parameter set is determined based on data obtained from cardiac beats of said heart in which said trigger event is an event associated with pacing of said right ventricle.

23. The method according to claim 20 wherein said first parameter set of said first artifact window is identical to said second parameter set of said first artifact window.

24. The method according to claim 20 wherein said first parameter set of said first artifact window is different than said second parameter set of said first artifact window.

25. The method according to claim 1 wherein said first artifact window starts at the time of detecting of said trigger event, and wherein said step of providing a first artifact window further comprises the step of determining the duration of said first artifact window within said current beat cycle by automatically selecting a first duration value for said first artifact window if said trigger event is a sensed event associated with intrinsic activation of a second cardiac chamber, and automatically selecting a second duration value for said first artifact window if said trigger event is an event associated with pacing of said second cardiac chamber.

26. The method according to claim 25 wherein said second cardiac chamber is the right atrium of said heart, wherein said first duration value of said first artifact window is predetermined based on data obtained from cardiac beats of said heart in which said trigger event is a right atrial sensed event associated with intrinsic activation of said right atrium, and wherein said second duration value of said first artifact window is predetermined based on data obtained from cardiac beats of said heart in which said trigger event is an event associated with pacing of said right atrium.

27. The method according to claim 25 wherein said second cardiac chamber is the right ventricle of said heart, wherein said first duration value of said first artifact window is predetermined based on data obtained from cardiac beats of said heart in which said trigger event is a sensed event associated with intrinsic activation of said right ventricle, and wherein said second duration value of said first artifact window is predetermined based on data obtained from cardiac beats of said heart in which said trigger event is an event associated with pacing of said right ventricle.

28. The method according to claim 25 wherein said first duration value of said first artifact window is identical to said second duration value of said first artifact window.

29. The method according to claim 25 wherein said first duration value of said first artifact window is different than said second duration value of said first artifact window.

30. The method according to claim 1 wherein said step of providing an alert window period comprises the step of determining the beginning time and the ending time of said alert window within said current beat cycle by automatically selecting a first alert window parameter set associated with said alert window period if said trigger event is a sensed event associated with intrinsic activation of a second cardiac chamber, automatically selecting a second parameter set associated with said alert window period if said trigger event is an event associated with pacing of said second cardiac chamber, and by computing said beginning time and said duration of said first artifact window from the selected parameter set.

31. The method according to claim 30 wherein said first cardiac chamber is the left ventricle of said heart, said second cardiac chamber is the right atrium of said heart, said first parameter set is determined based on data obtained from cardiac beats of said heart in which said trigger event is a sensed event associated with intrinsic activation of said right atrium, and said second parameter set is determined based on data obtained from cardiac beats of said heart in which said trigger event is an event associated with pacing of said right atrium.

32. The method according to claim 31 wherein said first cardiac chamber is the left ventricle of said heart, said second cardiac chamber is the right ventricle of said heart, said first parameter set is determined based on data obtained from cardiac beats of said heart in which said trigger event is a sensed event associated with intrinsic activation of said right ventricle, and said second parameter set is determined based on data obtained from cardiac beats of said heart in which said trigger event is an event associated with pacing of said right ventricle.

33. The method according to claim 1 further including the steps of:
   initiating an artifact proximity interval, said artifact proximity interval starts at the time of detection of a proximity interval initiating event detected within the duration of said first artifact window and has an artifact proximity interval duration; and
   inhibiting the performing of said step of providing a refractory period and of said step of applying, in response to detecting in said first electrogram signal an event occurring within the duration of a part of said artifact proximity interval, said part does not overlap said first artifact window.

34. The method according to claim 33 wherein said proximity artifact interval partially overlaps said alert window period.

35. The method according to claim 34 wherein said second step of inhibiting is performed when said event detected within the duration of said part of said artifact proximity interval, occurs within a portion of said alert window period, said portion overlaps said artifact proximity interval.

36. The method according to claim 33 wherein said step of initiating an artifact proximity interval further comprises the step of determining the duration of said artifact proximity interval by automatically selecting a first duration value for said artifact proximity interval if said trigger event is a sensed event associated with intrinsic activation of a second cardiac chamber, and automatically selecting a second duration value for said artifact proximity interval if said trigger event is an event associated with pacing of said second cardiac chamber.

37. The method according to claim 36 wherein said first cardiac chamber is the left ventricle of said heart, said second cardiac chamber is the right ventricle of said heart, said first duration of said artifact proximity interval is determined based on data obtained from cardiac beats of said heart in which said trigger event is a right ventricular sensed event associated with intrinsic activation of said right ventricle, and said second duration of said first artifact window is determined based on data obtained from cardiac beats of said heart in which said trigger event is an event associated with pacing of said right ventricle.

38. The method according to claim 33 wherein said proximity interval initiating event is the first event detected within the duration of said first artifact window.

39. The method according to claim 33 wherein more than one event is detected within the duration of said first artifact window and wherein said proximity interval initiating event is the last event detected within the duration of said first artifact window.

40. The method according to claim 33 wherein a plurality of events is detected within the duration of said first artifact window and wherein said proximity interval initiating event is a single event selected from said plurality of events.

41. The method according to claim 33 wherein said proximity interval initiating event is an event detected within the duration of said first artifact window using a detection method based on an analysis of morphological parameters of said first electrogram signal.

42. The method according to claim 1 further including the step of providing a second artifact window period within said current beat cycle in response to a first timing event and ignoring all events detected in said first electrogram signal within the duration of said second artifact window period to avoid inhibiting the delivery of said cardiac contractility modulating signal within said current beat cycle by the detection of an expected electrical artifact signal within the duration of said second artifact window period.

43. The method according to claim 42 wherein said first cardiac chamber is the left ventricle of said heart, said trigger event is an event associated with electrical activation of the right atrium of said heart and said first timing event is an event associated with electrical activation of the right ventricle of said heart.

44. The method according to claim 43 wherein said trigger event is a right atrial event detected by a sensing electrode electrically coupled to the right atrium of said heart, and wherein said first timing event is a right ventricular event detected by a sensing electrode electrically coupled to the right ventricle of said heart.

45. The method according to claim 43 wherein said trigger event is a right atrial event detected by a sensing electrode electrically coupled to the right atrium of said heart, and wherein said first timing event is a right ventricular pacing command or an event synchronized therewith.

46. The method according to claim 43 wherein said trigger event is a right atrial pacing command or an event synchronized therewith, and wherein said first timing event is a right ventricular event detected by a sensing electrode electrically coupled to the right ventricle of said heart.

47. The method according to claim 43 wherein said trigger event is a right atrial pacing command or an event synchronized therewith, and wherein said first timing event is a right ventricular pacing command or an event synchronized therewith.

48. The method according to claim 42 wherein said step of providing a second artifact window comprises the step of computing, within the duration of said current beat cycle, the beginning time and the ending time of said second artifact window period based on the time of occurrence of said first timing event and on the value of a pair of predetermined reconstruction parameters.

49. The method according to claim 48 wherein said beginning time of said second artifact window computed in said step of computing precedes said first timing event within said current beat cycle.

50. The method according to claim 48 wherein said beginning time of said second artifact window and said first timing event are identical within said current beat cycle.

51. The method according to claim 48 wherein said first timing event precedes said ending time of said second artifact window within said current beat cycle.

52. The method according to claim 48 wherein said ending time of said second artifact window and said first timing event are identical within said current beat cycle.

53. The method according to claim 42 wherein said first chamber is the left ventricle of said heart and wherein said step of providing a second artifact window comprises the steps of:
 if said first timing event is a sensed event associated with intrinsic activation of the right ventricle of said heart, automatically selecting a first parameter set associated with said second artifact window;
 if said first timing event is an event associated with pacing of said right ventricle of said heart, automatically selecting a second parameter set associated with said second artifact window; and
 determining the beginning time and the ending time of said second artifact window within said current beat cycle from the time of occurrence of said first timing event and from the automatically selected parameter set.

54. The method according to claim 53 wherein said first parameter set is determined based on data obtained from cardiac beats of said heart in which said first timing event is a right ventricular sensed event associated with intrinsic activation of said right ventricle, and said second parameter set is determined based on data obtained from cardiac beats of said heart in which said first timing event is an event associated with pacing of said right ventricle.

55. The method according to claim 53 wherein said first parameter set of said second artifact window is identical to said second parameter set of said second artifact window.

56. The method according to claim 53 wherein said first parameter set of said second artifact window is different than said second parameter set of said second artifact window.

57. The method according to claim 1 further including the step of providing a third artifact window period within said current beat cycle in response to a second timing event and ignoring all events detected in said first electrogram signal within the duration of said third artifact window period to avoid inhibiting the delivery of a cardiac contractility modulating signal within the next beat cycle following said current beat cycle by the detection of an expected electrical artifact signal within the duration of said third artifact window period of said current beat cycle.

58. The method according to claim 57 wherein said first cardiac chamber is the left ventricle of said heart, said trigger event is an event associated with electrical activation of the right ventricle of said heart and said second timing event is an event associated with electrical activation of the right atrium of said heart.

59. The method according to claim 58 wherein said trigger event is a right ventricular event detected by a sensing electrode electrically coupled to the right ventricle of said heart, and wherein said second timing event is a right atrial event detected by a sensing electrode electrically coupled to the right atrium of said heart.

60. The method according to claim 58 wherein said trigger event is a right ventricular event detected by a sensing electrode electrically coupled to the right ventricle of said heart, and wherein said second timing event is a right atrial pacing command or an event synchronized therewith.

61. The method according to claim 58 wherein said trigger event is a right ventricular pacing command or an event synchronized therewith, and wherein said second timing event is a right atrial event detected by a sensing electrode electrically coupled to the right atrium of said heart.

62. The method according to claim 58 wherein said trigger event is a right ventricular pacing command or an event synchronized therewith, and wherein said second timing event is a right atrial pacing command or an event synchronized therewith.

63. The method according to claim 57 wherein said step of providing a third artifact window comprises the step of computing, within the duration of said current beat cycle, the beginning time and the ending time of said third artifact window period based on the time of occurrence of said second timing event and on the value of a pair of predetermined reconstruction parameters.

64. The method according to claim 63 wherein said beginning time of said third artifact window computed in said step of computing precedes said second timing event within said current beat cycle.

65. The method according to claim 63 wherein said beginning time of said third artifact window and said second timing event are identical within said current beat cycle.

66. The method according to claim 63 wherein said second timing event precedes said ending time of said third artifact window within said current beat cycle.

67. The method according to claim 63 wherein said ending time of said third artifact window and said second timing event are identical within said current beat cycle.

68. The method according to claim 57 wherein said first chamber is the left ventricle of said heart, and said trigger event is a trigger event associated with the right ventricle of said heart and wherein said step of providing a third artifact window comprises the steps of:
  if said second timing event is a sensed event associated with intrinsic activation of the right atrium of said heart, automatically selecting a first artifact window parameter set associated with said third artifact window;
  if said second timing event is an event associated with pacing of said right atrium of said heart, automatically selecting a second parameter set associated with said third artifact window; and
  determining the beginning time and the ending time of said third artifact window within said current beat cycle from the time of occurrence of said second timing event and from the automatically selected parameter set.

69. The method according to claim 68 wherein said first parameter set is determined based on data obtained from cardiac beats of said heart in which said second timing event is a right atrial sensed event associated with intrinsic activation of said right atrium, and said second parameter set is determined based on data obtained from cardiac beats of said heart in which said second timing event is an event associated with pacing of said right atrium.

70. The method according to claim 68 wherein said first parameter set associated with said third artifact window is identical to said second parameter set associated with said third artifact window.

71. The method according to claim 68 wherein said first parameter set associated with said third artifact window is different than said second parameter set associated with said third artifact window.

72. The method according to claim 1 wherein said step of applying said cardiac contractility modulating signal comprises the steps of:
  if said trigger event is a sensed event associated with intrinsic activation of a second cardiac chamber, automatically selecting a first parameter set associated with said cardiac contractility modulating signal;
  if said trigger event is an event associated with pacing of said second cardiac chamber, automatically selecting a second parameter set associated with said cardiac contractility modulating signal;
  computing the beginning time and the ending time of said cardiac contractility modulating signal within said current beat cycle from the automatically selected parameter set and from the time of detecting of said first event in said step of enabling; and
  applying within said current beat cycle a cardiac contractility modulating signal having said beginning time and said ending time to said heart.

73. The method according to claim 72 wherein each of said first parameter set and said second parameter set includes a value of said first delay period and a value of said cardiac contractility modulating signal duration.

74. The method according to claim 72 wherein said first cardiac chamber is the left ventricle of said heart.

75. The method according to claim 74 wherein said second cardiac chamber is the right ventricle of said heart.

76. The method according to claim 75 wherein said first parameter set is determined based on data obtained from cardiac beats of said heart in which said trigger event is a right ventricular sensed event associated with intrinsic activation of said right ventricle, and said second parameter set is determined based on data obtained from cardiac beats of said heart in which said trigger event is an event associated with pacing of said right ventricle.

77. The method according to claim 74 wherein said second cardiac chamber is the right atrium of said heart.

78. The method according to claim 77 wherein said first parameter set is determined based on data obtained from cardiac beats of said heart in which said trigger event is a right atrial sensed event associated with intrinsic activation of said right atrium, and said second parameter set is determined based on data obtained from cardiac beats of said heart in which said trigger event is an event associated with pacing of said right atrium.

79. The method according to claim 1 wherein said step of providing a refractory period comprises the steps of:
  if said trigger event is a sensed event associated with intrinsic activation of a second cardiac chamber, automatically selecting a first parameter set associated with said refractory period;

if said trigger event is an event associated with pacing of said second cardiac chamber, automatically selecting a second parameter set associated with said refractory period; and computing said beginning time and said ending time of said refractory period within said current beat cycle from the automatically selected parameter set and from the time of detecting of said first event in said step of enabling.

80. The method according to claim 79 wherein each of said first parameter set and said second parameter set includes a value of said second delay period and a value of said refractory period duration.

81. The method according to claim 79 wherein said first cardiac chamber is the left ventricle of said heart.

82. The method according to claim 81 wherein said second cardiac chamber is the right ventricle of said heart.

83. The method according to claim 82 wherein said first parameter set is determined based on data obtained from cardiac beats of said heart in which said trigger event is a right ventricular sensed event associated with intrinsic activation of said right ventricle, and said second parameter set is determined based on data obtained from cardiac beats of said heart in which said trigger event is an event associated with pacing of said right ventricle.

84. The method according to claim 81 wherein said second cardiac chamber is the right atrium of said heart.

85. The method according to claim 84 wherein said first parameter set is determined based on data obtained from cardiac beats of said heart in which said trigger event is a right atrial sensed event associated with intrinsic activation of said right atrium, and said second parameter set is determined based on data obtained from cardiac beats of said heart in which said trigger event is an event associated with pacing of said right atrium.

86. A device for controlling the delivery of a non-excitatory cardiac contractility modulating signals to a heart within a cardiac beat cycle, the device comprising:

sensing means for sensing electrical activity in or about a first cardiac chamber to provide a first electrogram signal, and for sensing electrical activity in or about at least a second cardiac chamber of said heart to provide at least a second electrogram signal;

detecting means for detecting electrical events in said first electrogram signal and said at least second electrogram signal;

means for providing a first artifact window within the current beat cycle, said first artifact window starts at or after a trigger event representing the beginning of said current cardiac beat cycle, said first artifact window has a first artifact window duration, and detecting events occurring in said first electrogram signal within the duration of said first artifact window;

means for providing an alert window period within said current beat cycle, said alert window period has a first duration and is delayed from said trigger event;

means for enabling the delivery of a cardiac contractility modulating signal to said heart within said current beat cycle in response to a first event detected in said first electrogram signal within the duration of said alert window period, said delivery of said cardiac contractility modulating signal is delayed from the time of detecting of said first event occurring within the duration of said alert window period by a first delay period;

means for providing a refractory period within said current beat cycle, in response to said first event, said refractory period has a beginning time and an ending time, said beginning time is delayed from said first event of said step of enabling by a second delay period, said ending time occurs at or after the termination of said cardiac contractility modulating signal, for preventing the detection of electrical events within the duration of said refractory period;

means for applying said cardiac contractility modulating signal to said heart within said current beat cycle; and means for inhibiting said providing of said refractory period and for inhibiting said applying of said cardiac contractility modulating signal to said heart, in response to detecting at least one inhibiting event within said first electrogram signal.

87. The device according to claim 86 further including pacing means for pacing at least one cardiac chamber of said heart.

88. The device according to claim 87 further including implantable electrode means operatively connected to said pacing means for applying pacing pulses to at least one chamber of said heart.

89. The device according to claim 86 further including storage means for storing data within said device.

90. The device according to claim 89 further including means for communicating data to and from said storage means.

91. The device according to claim 86 further including implantable electrode means operatively connected to said sensing means and to said means for applying to perform said sensing in said heart and to apply said cardiac contractility modulating signals to said heart.

92. The device according to claim 86 further including means for inhibiting the delivery of a cardiac contractility modulating signal to said heart within the next cardiac beat cycle following said current beat cycle, in response to detecting in said first electrogram signal an event within the duration of a sensing time period, said sensing time period starts after the end of said refractory period of a beat cycle in which a cardiac contractility modulating signal is delivered to the heart and ends at the end of said current beat cycle in which a cardiac contractility modulating signal is delivered to the heart.

93. The device according to claim 86 further including means for inhibiting the delivery of a cardiac contractility modulating signal to said heart within the next cardiac beat cycle following said current beat cycle, in response to detecting in said first electrogram signal an event within the duration of a sensing time period starting after the end of said alert window and ending at the end of said first delay period, wherein the delivery of a cardiac contractility modulating signal to the heart within said current beat cycle was inhibited in said current beat cycle.

94. The device according to claim 86 wherein said at least one inhibitory event comprises a single event or any combination of events selected from the group of events consisting of, an event detected in said first electrogram signal within the time interval between the ending time of said first artifact window and the starting time of said alert window period, an event detected in said first electrogram signal within the duration of said alert window period after the time of detection of said first event of said step of enabling, and an event detected within the time interval starting after the end of said alert window and ending at said beginning time of said refractory period.

95. The device according to claim 86 further comprising,
means for providing an artifact proximity interval, said artifact proximity interval starts at the time of detection of a proximity interval initiating event detected within said first artifact window and has an artifact proximity interval duration, and means for inhibiting the providing of said refractory period and for inhibiting the applying of said cardiac contractility modulating signal, in response to detecting in said first electrogram signal an event occurring within a part of said artifact proximity interval, said part does not overlap said first artifact window.

96. The device according to claim 95 wherein said proximity artifact interval partially overlaps said alert window period.

97. The device according to claim 95 wherein said proximity interval initiating event is the first event detected within the duration of said first artifact window.

98. The device according to claim 95 wherein more than one event is detected within the duration of said first artifact window and wherein said proximity interval initiating event is the last event detected within the duration of said first artifact window.

99. The device according to claim 95 wherein a plurality of events is detected within the duration of said first artifact window and wherein said proximity interval initiating event is a single event selected from said plurality of events.

100. The device according to claim 86 wherein said proximity interval initiating event is an event detected within the duration of said first artifact window using a detection method based on an analysis of morphological parameters of said first electrogram signal.

101. The device according to claim 86 further including storage means, for storing a plurality of parameter sets associated with at least one of said first artifact window, said alert window, said refractory period, and said cardiac contractility modulating signal.

102. The device according to claim 101 further including means for automatically selecting a parameter set associated with at least one of said first artifact window, said alert window, said refractory period, and said cardiac contractility modulating signal, said selecting is based on events selected from events associated with pacing of said at least second cardiac chamber, events associated with intrinsic activation of said at least second cardiac chamber, and any combination thereof.

103. A device for controlling the delivery of a non-excitatory cardiac contractility modulating signals to a heart within a cardiac beat cycle, the device comprising:

at least one sensing unit for sensing electrical activity in or about a first cardiac chamber to provide a first electrogram signal and for sensing electrical activity in at least a second cardiac chamber to provide at least a second electrogram signal;

at least one detecting unit adapted to detect electrical events in said first electrogram signal and in said at least second electrogram signal;

a cardiac contractility modulating unit for delivering cardiac contractility modulating signals to said heart; and at least one controller unit operatively connected to said at least one sensing unit, said at least one detecting unit, and to said cardiac contractility modulating unit, said at least one controller unit is adapted to provide a first artifact window within the current beat cycle, said first artifact window starts at or after a trigger event representing the beginning of said current cardiac beat cycle, said first artifact window has a first artifact window duration, and to detect events occurring in said first electrogram signal within the duration of said first artifact window, said at least one controller unit is adapted to provide an alert window period within said current beat cycle, said alert window period has a first duration and is delayed from said trigger event, for enabling the delivery of a cardiac contractility modulating signal to said heart by said cardiac contractility modulating unit within said current beat cycle in response to an enabling event detected in said first electrogram signal within the duration of said alert window period, said delivery of said cardiac contractility modulating signal is delayed from the time of detecting of said enabling event occurring within the duration of said alert window period by a first delay period, said at least one controller unit is adapted to provide a refractory period within said current beat cycle, in response to said enabling event, said refractory period has a beginning time and an ending time, said beginning time is delayed from said enabling event by a second delay period, said ending time occurs at or after the termination of said cardiac contractility modulating signal, to prevent the detection of electrical events within the duration of said refractory period, said at least one controller unit is adapted to control the applying by said cardiac contractility modulating unit of said cardiac contractility modulating signal to said heart within said current beat cycle, said at least one controller unit is adapted to inhibit the providing of said refractory period and the delivery of said cardiac contractility modulating signal within said current beat cycle, in response to detecting an inhibiting event within said first electrogram signal.

104. The device according to claim 103 further including a memory unit operatively connected to said at least one controller unit for storing data within said device.

105. The device according to claim 104 further including a communication unit operatively connected to said at least one controller unit for communicating data to and from said memory unit.

106. The device according to claim 103 further including an implantable electrode operatively connected to said at least one sensing unit for performing sensing in said first cardiac chamber, at least one electrode operatively connected to said at least one sensing unit for performing sensing in said at least second cardiac chamber, and at least one electrode operatively connected to said cardiac contractility modulating unit for applying said cardiac contractility modulating signals to said heart.

107. The device according to claim 103 further including a pacing unit operatively connected to said at least one controller unit, for pacing at least one cardiac chamber of said heart.

108. The device according to claim 107 further including at least one implantable electrode operatively connected to said pacing unit for pacing at least one cardiac chamber of said heart.

109. The device according to claim 103 wherein said detecting unit is included within said at least one controller unit.

110. The device according to claim 103 wherein said controller unit is adapted for inhibiting the delivery of a cardiac contractility modulating signal to said heart within the next cardiac beat cycle following said current beat cycle, in response to detecting in said first electrogram signal an event within the duration of a sensing time period starting after the end of said refractory period of a beat cycle in which a cardiac contractility modulating signal is delivered to said heart and ending at the end of said current beat cycle in which said cardiac contractility modulating signal is delivered to said heart.

111. The device according to claim 103 wherein said controller unit is adapted for inhibiting the delivery of a cardiac contractility modulating signal to said heart within the next cardiac beat cycle following said current beat cycle, in response to detecting by said at least one detecting unit in said first electrogram signal an event within the duration of a sensing time period starting after the end of said alert window and ending at the end of said first delay period, wherein the delivery of a cardiac contractility modulating signal to the heart within said current beat cycle was inhibited in said current beat cycle.

112. The device according to claim 103 wherein said at least one inhibitory event comprises a single event or any combination of events selected from the group of events consisting of,
- an event detected by said at least one detecting unit in said first electrogram signal within the time interval between the ending time of said first artifact window and the starting time of said alert window period,
- an event detected by said at least one detecting unit in said first electrogram signal within the duration of said alert window period after the time of detection of said first event of said step of enabling, and
- an event detected by said at least one detecting unit within the time interval starting after the end of said alert window period and ending at said beginning time of said refractory period.

113. The device according to claim 103 wherein said at least one controller unit is adapted for providing an artifact proximity interval, said artifact proximity interval starts at the time of detection of a proximity interval initiating event detected within said first artifact window and has an artifact proximity interval duration, and wherein said at least one controller unit is further adapted to inhibit the providing of said refractory period and to inhibit the applying of said cardiac contractility modulating signal, in response to the detecting, by said at least one detecting unit, in said first electrogram signal an event occurring within a part of said artifact proximity interval, said part does not overlap said first artifact window.

114. The device according to claim 113 wherein said proximity artifact interval partially overlaps said alert window period.

115. The device according to claim 112 wherein said proximity interval initiating event is the first event detected within the duration of said first artifact window.

116. The device according to claim 112 wherein more than one event is detected within the duration of said first artifact window and wherein said proximity interval initiating event is the last event detected within the duration of said first artifact window.

117. The device according to claim 112 wherein a plurality of events is detected within the duration of said first artifact window and wherein said proximity interval initiating event is a single event selected from said plurality of events.

118. The device according to claim 112 wherein said proximity interval initiating event is an event detected within the duration of said first artifact window using a detection method based on an analysis of morphological parameters of said first electrogram signal.

119. The device according to claim 103 wherein said at least one controller unit is adapted to provide a second artifact window period within said current beat cycle in response to a first timing event and to ignore all events detected in said first electrogram signal within the duration of said second artifact window period, to avoid inhibiting the delivery of said cardiac contractility modulating signal within said current beat cycle by the detection of an expected electrical artifact signal within the duration of said second artifact window period.

120. The device according to claim 119 wherein said first timing event is an event detected by said at least one detecting unit in said at least second electrogram signal, said first timing event is associated with electrical activation of said at least second cardiac chamber.

121. The device according to claim 119 wherein said first timing event is an event associated with pacing of said at least second cardiac chamber.

122. The device according to claim 121 wherein said first timing event is a pacing command signal associated with pacing of said at least second cardiac chamber.

123. The device according to claim 119 wherein said second artifact window period partially overlaps said alert window period.

124. The device according to claim 103 wherein said at least one controller unit is adapted to provide a third artifact window period within said current beat cycle in response to a second timing event, and to ignore all events detected in said first electrogram signal within the duration of said third artifact window period to avoid inhibiting the delivery of a cardiac contractility modulating signal within the next beat cycle following said current beat cycle by the detection of an expected electrical artifact signal within the duration of said second artifact window period.

125. The device according to claim 124 wherein said second timing event is an event detected by said at least one detecting unit in said at least second electrogram signal, said second timing event is associated with electrical activation of said at least second cardiac chamber.

126. The device according to claim 124 wherein said second timing event is an event associated with pacing of said at least second cardiac chamber.

127. The device according to claim 124 wherein said second timing event is a pacing command signal associated with pacing of said at least second cardiac chamber.

128. The device according to claim 103 further including a memory unit operatively connected to said at least one controller unit for storing a plurality of parameter sets associated with at least one of said first artifact window, said alert window, said refractory period, and said cardiac contractility modulating signal.

129. The device according to claim 128 wherein said at least one controller unit is adapted for automatically selecting from said plurality of parameter sets at least one parameter set associated with said at least one of said first artifact window, said alert window, said refractory period, and said cardiac contractility modulating signal, said selecting is based on at least one event selected from events associated with pacing of said at least second cardiac chamber, events associated with intrinsic activation of said at least second cardiac chamber, and any combination thereof.

* * * * *

UNITED STATES PATENT AND TRADEMARK OFFICE
CERTIFICATE OF CORRECTION

PATENT NO. : 6,370,430 B1
DATED : April 9, 2002
INVENTOR(S) : Yuval Mika et al.

It is certified that error appears in the above-identified patent and that said Letters Patent is hereby corrected as shown below:

Title page,
Item [73], Assignee, "Curecao" should be replaced with -- Curacao --

Column 78,
Line 35, the word "inhibitory" should be replaced with the word -- inhibiting --.

Column 89,
Line 20, the word "inhibitory" should be replaced with the word -- inhibiting --.

Signed and Sealed this

Twelfth Day of August, 2003

JAMES E. ROGAN
*Director of the United States Patent and Trademark Office*